(12) United States Patent
Thurston et al.

(10) Patent No.: US 7,265,105 B2
(45) Date of Patent: *Sep. 4, 2007

(54) PYRROLOBENZODIAZEPINES

(75) Inventors: David Edwin Thurston, Nottingham (GB); Philip Wilson Howard, Nottingham (GB)

(73) Assignee: Spirogen Limited, Isle of Wight (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/367,241

(22) Filed: Mar. 2, 2006

(65) Prior Publication Data

US 2006/0148788 A1 Jul. 6, 2006

Related U.S. Application Data

(63) Continuation of application No. 09/763,767, filed as application No. PCT/GB99/02838 on Aug. 27, 1999, now Pat. No. 7,049,311.

(30) Foreign Application Priority Data

Aug. 27, 1998 (GB) .................. 9818733.9
Jan. 28, 1999 (GB) .................. 9901929.1

(51) Int. Cl.
  A61P 35/00 (2006.01)
  A61K 31/55 (2006.01)
  C07D 487/00 (2006.01)
(52) U.S. Cl. ..................... 514/220; 540/496
(58) Field of Classification Search ............... 514/220; 540/496
  See application file for complete search history.

(56) References Cited

U.S. PATENT DOCUMENTS

| | | | |
|---|---|---|---|
| 3,523,941 A | 8/1970 | Leimgruber et al. | 260/239.3 |
| 3,524,849 A | 8/1970 | Batcho et al. | 260/239.3 |
| 4,185,016 A | 1/1980 | Takanabe et al. | 260/239.3 T |
| 4,239,683 A | 12/1980 | Takanabe et al. | 260/239.3 T |
| 4,309,437 A | 1/1982 | Ueda et al. | 424/274 |
| 5,143,854 A | 9/1992 | Pirrung et al. | 436/518 |
| 5,545,568 A | 8/1996 | Ellman et al. | 436/518 |
| 6,562,806 B1 | 5/2003 | Thurston et al. | 514/185 |
| 6,608,192 B1 | 8/2003 | Thurston et al. | 540/496 |
| 6,660,856 B2 | 12/2003 | Wang | 540/496 |
| 6,747,144 B1 | 6/2004 | Thurston et al. | 540/496 |
| 2003/0120069 A1 | 6/2003 | Thurston et al. | 540/561 |
| 2003/0195196 A1 | 10/2003 | Thurston et al. | 514/220 |
| 2004/0092736 A1 | 5/2004 | Thurston et al. | 540/569 |
| 2004/0198722 A1 | 10/2004 | Thurston et al. | 514/220 |

FOREIGN PATENT DOCUMENTS

| | | |
|---|---|---|
| EP | 0239400 A2 | 9/1987 |
| EP | 1193270 | 4/2002 |
| FR | 2027356 | 12/1969 |
| FR | 2586683 D | 3/1987 |
| GB | 1299198 D | 12/1972 |
| GB | 2053894 | 2/1981 |
| JP | 53-82792 | 7/1978 |
| JP | 57131791 | 8/1982 |
| JP | 58180487 | 10/1983 |
| WO | WO88/04659 | 6/1988 |
| WO | WO88/07378 | 10/1988 |
| WO | WO89/10140 | 11/1989 |
| WO | WO91/16324 | 10/1991 |
| WO | WO92/19620 D | 11/1992 |
| WO | WO93/08288 | 4/1993 |
| WO | WO93/18045 | 9/1993 |
| WO | WO96/23497 | 8/1996 |
| WO | WO97/01560 D | 1/1997 |
| WO | WO97/07097 | 2/1997 |
| WO | WO98/11101 | 3/1998 |
| WO | WO98/12197 | 3/1998 |
| WO | WO99/29642 | 6/1999 |
| WO | WO99/46244 | 9/1999 |

(Continued)

OTHER PUBLICATIONS

Adams et al., "Molecular modelling of a sequence-specific DNA-binding agent based on the pyrrolo[2,1-c][1,4]benzodiazepines," Pharm. Pharmacol. Commun. (1999) 5:555-560.

(Continued)

*Primary Examiner*—Brenda Coleman
(74) *Attorney, Agent, or Firm*—Michael Best & Friedrich LLP

(57) ABSTRACT

A compound of the formula II:

(II)

wherein:
  $R'_2$ is $CHR''_2$, where $R''_2$ is H.
  $R_6$ and $R_9$ are H and $R_7$ is OMe
  and the compound is a dimer with each monomer being the same and being of formula II, where the $R_8$ groups of the monomers form together a bridge having the formula $—O—(CH_2)_p—O—$, where p is 5, linking the monomers.

3 Claims, 11 Drawing Sheets

FOREIGN PATENT DOCUMENTS

| WO | WO 00/12506 | 3/2000 |
|---|---|---|
| WO | WO 00/12507 | 3/2000 |
| WO | WO 00/12508 | 3/2000 |
| WO | WO 00/12509 | 3/2000 |
| WO | WO 00/64864 | 11/2000 |
| WO | WO 2004/043963 | 5/2004 |
| WO | WO 2005/023814 | 3/2005 |
| WO | WO 2005/040170 | 5/2005 |
| WO | WO 2005/085251 | 9/2005 |

OTHER PUBLICATIONS

Albericio, F. et al., "NPE-Resin, A New Approach to the Solid-Phase Synthesis of Protected Peptides and Oligonucleotides II. Synthesis of Protected Peptides[1,2]," Tetrahedron Letters, 32:1515-1518 (1991).

Albericio, F. et al., "NPE-resin, a new approach to the solid-phase synthesis of protected peptides and oligonucleotides," Peptides 1990, Proc. 21.sub.st Eur. Pept. Symp., 134-136 (1990).

Althius, T. H. and Hess, H. J., "Synthesis and Identification of the Major Metabolites of Prazosin Formed in Dog and Rat," J. Medicinal Chem., 20(1), 146-148 (1977).

Arima et al., "Studies on Tomaymycin, a New Antibiotic. I. Isolation and Properties of Tomaymycin," J. Antibiotics, 25, 437-444 (1972).

Aristoff, J and Johnson, P., "Synthesis of CBI-PDE-I-Dimer, the Benzannelated Analogue of CC-1065," J. Org. Chem., 57, 6234-6239 (1992).

Bagshawe et al., "Antibody-Enzyme Conjugates Can Generate Cytotoxic Drugs from Inactive Precursors at Tumor Sites," Antibody, Immunoconjugates, and Radiopharmaceuticals, 4, 915-922 (1991).

Baraldi, P.G. et al., "Design, synthesis and biological activity of a pyrrolo[2,1-c][1,4]benzodiazepine (PBD)-distamycin hybrid," Bioorganic & Medicinal Chemistry Letters, vol. 8, No. 21, 3019-3024 (1998).

Baraldi, P.G. et al., "Synthesis, in Vitro Antiproliferative Activity, and DNA-Binding Properties of Hybrid Molecules Containing Pyrrolo[2,1-c][1,4]benzodiazepine and Minor-Groove-Binding Oligopyrrole Carriers," J. Med. Chem., 42, 5131-5141 (1999).

Baraldi, P.G. et al., "[2,1-c][1,4]benzodiazepine (PBD)-distamycin hybrid inhibits DNA binding to transcription factor Sp1," Nucleotides and Nucleic Acids (2000) 19(8):1219-1229.

Bayley, H. et al., "Photoactivatable drugs," TIPS, 8, 138-143 (1987).

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," Tetrahedron Letters, 41, 6171-6174 (2000).

Bi, Y. et al., "Building blocks for peptide and carbamate libraries", Bioorganic & Medicinal Chemistry Letters, vol. 6, No. 19, 2299-2300 (1996).

Bi, Y., et al., "Building blocks for peptide and carbamate libraries," Chemical Abstracts, vol. 125, No. 23, 1013 (1996).

Boger et al., "CC-1065 and the Duocarmycins: Synthetic Studies," Chem. Rev., 97, 787-828 (1997).

Borgatti, M. et al., "Inhibition of NF-kB/DNA interactions and HIV-1 LTR directed transcription by hybrid molecules containing pyrrolo [2,1-c][1,4] benzodiazepine (PBD) and oligopyrrole carriers," Drug Development Research (2003) 60(3):173-185.

Bose et al., "New Approaches to Pyrrolo[2,1-c][1,4]benzodiazepines: Synthesis, DNA-binding and cytotoxicity of DC-81," Tetrahedron, 48, 751-758 (1992).

Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Bridges, R.J. et al., "Conformationally Defined Neurotransmitter Analogues. Selective Inhibition of Glutamate Uptake by One Pyrrolidine-2,4-dicarboxylate Diastereomer," J. Med. Chem., 34, 717-725 (1991).

Brown, S.C. et al., "NMR Solution Structure of a Peptide Nucleic Acid Complexed with RNA," Science, 265, 777-780 (1994).

Bundgaard, H., "Design and Application of Prodrugs," A Textbook of Drug Design and Development, eds Krogsgaard-Lassen, P., and Bundgaard, H., Harwood Academic Press, 113-135 (1991).

Burgess, K. et al., "Solid Phase Synthesis of Oligoureas", J.Ame. Chem. Soc., 119: 1556-1564 (1997).

Burgess, K et al., "Solid Phase Synthesis of Unnatural Biopolymers Containing Repeating Urea Units," Agnew Chem. Int. Ed. Engl, 34, No. 8:907-909 (1995).

Carruth, J.A.S., "Clinical applications for photodynamic therapy," J. Photochem Photobiol., 9, 396-397 (1991).

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cho, C Y et al., "An Unnatural Biopolymer", Science, 261: 1303-1305 (1993).

Cooper, N. et al., "Synthesis of novel PBDs as anti-tumour agents," Chem. Commun. (2002) 16:1764-1765.

Courtney, S. M. et al., "A new convenient procedure for the synthesis of pyrrolo[2,1-c][1,4]benzodiazepines", Tetrahedron Letters, vol. 34, No. 33, 5327-28 (1993).

Culver et al., "In Vivo Gene Transfer with Retroviral Vector-Producer Cells for Treatment of Experimental Brain Tumors," Science, 256, 1550-1552 (1992).

Dalton, S. and Treisman, R, "Characterization of SAP-1, a Protein Recruited by Serum Response Factor to the c-fos Serum Response Element," Cell, 68, 597-612 (1992).

Damayanthi, Y., et al., "Design and synthesis of novel pyrrolo {2,1-c][1,4] benzodiazepine-Lexitropsin Conjugates," J. Org. Chem., 64, 290-292 (1999).

Dangles, O. et al., "Selective Cleavage of the Allyl and Allyloxycarbonyl Groups through Palladium-Catalyzed Hydrostannolysis with Tributyltin Hydride. Application to the Selective Protection-Deprotection of Amino Acid Derivatives and in Peptide Synthesis," J. Org. Chem., 52, 4984-4993 (1987).

De Groot, Fmh et al., "Synthesis and biological evaluation of 2'-carbamate-linked 2'-carbonate-linked prodrugs of paclitaxel: selective activation by the tumor-associated protease plasmin," J. Med. Chem. (2000) 43(16):3093-3102.

De Groot, Fmh et al., "Novel 20-carbonate linked prodrugs of camptothecin and 9-aminocamptothecin designed for activation by tumour-associated plasmin," Biorg. Med. Chem. Lett. (2002) 12(17):2371-2376.

Dictionary of Science and Technology, Professor P.M.B. Walker ed. Larousse plc., pp. 63, 457, 523 (1995).

Dressman, B.A., et al., "Solid Phase Synthesis of Hydantoins Using a Carbamate Linker and a Novel Cyclization/Cleavage Step," Tetrahedron Letters, 37, 937-940 (1996).

Drost, K.J. and Cava, M.P., "A Photochemically Based Synthesis of the Benzannelated Analogue of the CC-1065 A Unit," J. Org. Chem., 56:2240-2244 (1991).

Dubowchik, G.M. et al., "Cathepsin B-sensitive dipeptide prodrugs. 1. A model study of structural requirements for efficient release of doxorubicin," Biorg. Med. Chem. Lett. (1998) 8:3341-3346.

Dubowchik, G.M. et al., "Cathepsin B-sensitive dipeptide prodrugs. 2. Models of anticancer drugs paclitaxel (Taxol), Mitomycin C and Doxorubicin," Biorg. Med. Chem. Lett. (1998) 8:3347-3352.

Dubowchik and Walker, "Receptor-mediated and enzyme-dependent targeting of cytotoxic anticancer drugs," Pharmacology and Therapeutics (1999) 83:67-123.

Eashoo, M. et al., "Fibers from a Low Dielectric Constant Fluorinated Polyimide: Solution Spinning and Morphology Control," J. Polymer Science, 35:173-185 (1997).

Edman, P. and Begg, G., "A Protein Sequenator," Eur. J. Biochem., 1, 80-91 (1967).

Egholm, M et al., "Peptide Nucleic Acids (PNA). Oligonucleotide Analogues with an Achiral Peptide Backbone," *J. Am. Chem. Soc.*, 114, 1895-1897 (1992).

Egholm, M et al., "PNA hybridizes to complementary oligonucleotides obeying the Watson-Crick hydrogen-bonding rules," *Nature*, 365, 566-568 (1993).

Englehardt et al., "Direct gene transfer of human CFTR into human bronchial epithelia of xenografts with E1-deleted adenoviruses," *Nature Genetics*, 4, 27-34 (1993).

Farmer, J.D. et al., "DNA binding properties of a new class of linked anthramycin analogs,", *Chemical Abstracts*, Abstract No. 239940r, vol. 114, No. 25, 25 899-903 (1991).

Figliozzi, G.M. et al., "Synthesis of N-substituted Glycine Peptoid Libraries," *Methods in Enzymology*, 267: 437-447 (1996).

Foloppe, M.P. et al., "DNA-binding properties of pyrrolo[2,1-c][1,4]benzodiazephine N10-C11 amidines," *Eur. J. Med. Chem.*, 31, 407-410 (1996).

Fujisawa Pharmaceutical Co., Ltd., Abstract No. 139983k, "Benzodiazepine derivatives", *Chemical Abstracts*, vol. 99, No. 17, 603 (1983).

Fujisawa Pharmaceutical Co., Ltd., Abstract No. 72145x, "Benzodiazepine derivatives", *Chemical Abstracts*, vol. 98, No. 9, 638 (1983).

Fujisawa Pharmaceutical Co. Ltd., "Benzodiazepine derivatives," *SciFinder Scholar*, 2-3 (2002).

Fukuyama, T. et al., "Total Synthesis of (+)-Porothramycin B," *Tetrahedron Letters*, vol. 34, 16, 2577-2580 (1993).

Furka, A. et al., "General method for rapid synthesis of multicomponent peptide mixtures," *Int. J. Peptide Protein Res.*, 37, 487-493 (1991).

Garcia-Echeverria, C., "A Base Labile Handle for Solid Phase Organic Chemistry", *Tetrahedron Letters*, 38,52, 8933-8934 (1997).

Garsky et al., "The synthesis of a prodrug of doxorubicin designed to provide reduced systemic toxicity and greater target efficacy," J. Med. Chem. (2001) 44:4216-4224.

Grant, R. et al., *Grant and Hackh's Chemical Dictionary*, McGraw-Hill Book Company, 282 (1987).

Greene, T.W. and Wuts, P.G.M., *Protective Groups in Organic Synthesis*, John Wiley & Sons, 2$^{nd}$ ed., Ch 7, 315-345 (1991).

Gregson, S. et al., "Synthesis of a novel C2/C2'-exo unsaturated pyrrolobenzodiazepine cross-linking agent with remarkable DNA binding affinity and cytotoxicity," *Chemical Communications*, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J. Med. Chem.*, 44: 737-748 (2001).

Gregson, S.J. et al., "Effect of C2-*exo* Unsaturation on the Cytotoxicity and DNA-Binding Reactivity of Pyrrolo[2,1-c]1,4]benzodiazepines", *Bioorganic & Medicinal Chemistry Letters*, 10: 1845-1847 (2000).

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Guiotto, A. et al., "Synthesis of novel C7-aryl substituted pyrrolo[2,1-c][1,4]benzodiazepines (PBDs) via Pro-N10-troc protection and suzuki coupling," *Bioorganic & Medicinal Chemistry Letters*, 8, No. 21, 3017-3018 (1998).

Hamburger, A.W. et al., "Primary bioassay of human tumor stem cells," Science (1977) 197:461-463.

Hara et al., "DC 102, a new glycosidic pyrrolo(1,4)benzodiazepine antibiotic produced by *streptomyces* sp.", *J. Antibiotics*, 702-704 (1998).

Hauske, J. R. and Dorff, P., "Solid Phase CBZ Chloride Equivalent. A New Matrix Specific Linker", *Tetrahedron Letters*, 36, 10, 1589-1592 (1995).

Hocart et al., "Highly potent cyclic disulfide antagonists of somatostatin," *J. of Medicinal Chem.*, 42:11 (1999).

Hochlowski, J. et al., "Abbeymycin, a new anthramycin-type antibiotic produced by a streptomycete," *J. Antibiotics*, 40, 145-148 (1987).

Holmes, C.P. and Jones, D.G., "Reagents for Combinational Organic Synthesis: Development of a New O-Nitrobenzyl Photolabile Linker for Solid Phase Synthesis", *J. Org. Chem.*, 60, 2318-2319 (1995).

Huber, B. et al., "Retroviral-mediated gene therapy for the treatment of hepatocellular carcinoma: An innovative approach for cancer therapy," *Proc. Natl. Acad. Sci. USA*, 88, 8039-8043 (1991).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).

Itoh et al., "Sibanomicin, a new pyrrolo(1,4)benzodiazepine antitumor antibiotic produced by a *micromonospora* sp." *J. Antibiotics*, 41, 1281-1284 (1988).

Jakobsen et al., "Design, synthesis, and pharmacological evaluation of thapsigargin analogues for targeting apoptosis to prostatic cancer cells," J. Med. Chem. (2001) 44:4696-4703.

Jenkins, T.C. et al., "Structure of a Covalent DNA Minor Groove Adduct with a Pyrrolobenzodiazepine Dimer: Evidence for Sequence-Specific Interstrand Cross-Linking," *J. Med. Chem.*, 37, 4529-4537 (1994).

Jungheim, L.N. and Shepherd, T.A., "Design of Antitumor Prodrugs: Substrates for Antibody Targeted Enzymes," *Am. Chem. Soc. Chem. Rev.*, 94, 1553-1566 (1994).

Kamal, A., et al., "An Efficient Synthesis of Pyrrolo[2,1-c][1,4]Benzodiazepine Antibiotics via Reductive Cyclization," *Bioorg. Med. Chem. Ltrs*, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TRAP", *Tetrahedron*, v. 53, No. 9, 3223-3230 (1997).

Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Kapoor, T.M. et al., "Exploring the Specificity Pockets of Two Homologous SH3 Domains Using Structure-Based, Split-Pool Synthesis and Affinity-Based Selection," *J. Am. Chem. Soc.* 120:23-29 (1998).

Katritzky et al., *Heterocyclic Chemistry*, John Wiley & Sons, Inc., 247-253 (1960).

Kennedy, J.C. and Pottier, R.H., "Endogenous protoporphyrin IX, a clinical useful photosensitiser for photodynamic therapy," *J. Photochem Photobiol*, 14, 275-292 (1992).

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J. Antibiotics*, 37, 200-206 (1984).

Kumar, R. et al., "Synthesis and antitumor cytotoxicity evaluation of novel pyrrolo[2,1-c][1,4]benzodiazepine imidazole containing polyamide conjugates," Oncology Research (2003) 13(4):221-223.

Kumar, R. et al., "Design and synthesis of novel pyrrolo[2,1-c][1,4]benzodiazepine—imidazole containing polyamide conjugates," Heterocyclic Communications (2002) 81(1):19-26.

Kumar, R. et al., "Design, synthesis and in vitro cytotoxicity studies of novel pyrrolo [2,1][1,4]benzodiazepine-glycosylated pyrrole and imidazole polyamide conjugates," *Org. Biomol. Chem.* (2003) 1(19):3327-3342.

Kunimoto et al., "Mazethramycin, a new member of anthramycin group antibiotics," *J. Antibiotics*, 33, 665-667 (1980).

Kunz, H. and Dombo, B., "Solid Phase Synthesis of Peptide and Glycopeptides on Polymeric Supports with Allylic Anchor Groups," *Angew Chem. Int. Ed. Engl*, 5, 711-713 (1988).

Kuzmich, S. et al., "Increased levels of glutathione S-transferase π transcript as a mechanism of resistance to ethacrynic acid," *Journal of Biochemistry*, 281, 219-224 (1992).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," *J. Am. Chem. Soc.*, 110, 2992-2993 (1988).

Leimgruber, W. et al., "Isolation and characterization of anthramycin, a new antitumor antibiotic," *J. Am. Chem. Soc.*, 87, 5791-5793 (1965).

Leimgruber, W. et al., "The structure of anthramycin," *J. Am. Chem. Soc.*, 87, 5793-5795 (1965).

Leimgruber, W. et al., "Total synthesis of anthramycin," *J. Am. Chem. Soc.*, 90, 5641-5643 (1968).

Lescrinier, T. et al., "DNA-Binding Ligands from Peptide Libraries Containing Unnatural Amino Acids," *Chem. Eur. J.*, 4, 3, 425-433 (1998).

Lewis A.D. et al., "Glutathione and glutathione-dependent enzymes in ovarian adenocarcinoma cell lines derived from a patient before and after the onset of drug resistance: intrinsic differences and cell cycle effects," *Carcinogenesis*, 9, 1283-1287 (1988).

Lipshutz, B.H. et al., "Pd(II)_Catalyzed Acetal/Ehtal Hydrolysis/Exchange Reactions," Tetrahedron Lett. (1985) 26(6):705-708.

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026; and Abstract No. 51709.

Mhaka et al., "A 5-fluorodeoxyuridine prodrug as targeted therapy for prostate cancer," Biorg. Med. Chem. Lett. (2002) 12(17:2459-2461.

Mischiati, C. et al., "Binding of hybrid molecules containing pyrrolo [2,1-c][1,4]benzodiazepine (PBD) and oligopyrrole carriers to the human immunodeficiency type 1 virus TAR-RNA," Biochem. Pharmacol. (2004) 67(3):401-410.

Mizushima, S. and Nagata, S., "pEF-BOS, a powerful mammalian expression vector," *Nucl. Acids Res.*, 18, 5322 (1990).

Monks, A. et al., "Feasibility of High-Flux Anticancer Drug Screen Using a Diverse Panel of Cultured Human Tumor Cell Lines," *Journal of National Cancer Institute*, 83, 757-766 (1991).

Moran, E.J. et al., "Novel Biopolymers for Drug Discovery: Biopolymers", *Peptide Science*, John Wiley and Sons, 37: 213-19 (1995).

Morgan, R.A. and Anderson, W.F., "Human Gene Therapy," *Annu. Rev. Biochem.*, 62, 191-217 (1993).

Mori, M. et al., "Total syntheses of prothracarcin and tomaymycin by use of palladium catalyzed carbonylation," Tetrahedron (1986) 42(14):3793-3806.

Mosmann, T., "Rapid Colorimetric Assay for Cellular Growth and Survival: Application to Proliferation and Cytotoxicity Assays," *J. Immunological Methods*, 65, 55-63 (1983).

Mountzouris, J.A. et al., "Comparison of a DSB-120 DNA interstrand cross-linked adduct with the corresponding bis-Tomamycin adduct," J. Med. Chem. (1994) 37:3132-3140.

Mullen, D.G. and Barany, G., "A New Fluoridolyzable Anchoring Linkage for Orthogonal Solid-Phase Peptide Synthesis: Design, Preparation, and Application of the N-(3 or 4)-[[4-(Hydroxymethyl) phenoxy]-tert-butylphenylsilyl]phenyl Pentanedioic Acid Monoamide (Pbs) Handle", *J. Org. Chem.*, 53, 5240-5248 (1988).

Nagasaka, T. and Koseki, Y, "Stereoselective Synthesis of Tilivalline," *Journal of Organic Chemistry*, vol. 63, No. 20, 6797-6801 (1998).

Nagasaka, T. et al., "Stereoselective Synthesis of Tilivalline," *Tetrahedron Letters*, 30:14, 1871-1872 (1989).

Nicolaou, K.C. et al., "Designed Enediynes: A New Class of DNA-Cleaving Molecules with Potent and Selective Anticancer Activity," *Science*, 256, 1172-1178 (1992).

Niculescu-Duvaz, D. et al., "Self-immolative nitrogen mustard prodrugs for suicide gene therapy," J. Med. Chem. (1998) 41(26):5297-5309.

Nielson, P.E. et al., "Sequence-Selective Recognition of DNA by Strand Displacement with a Thymine-Substituted Polyamide," *Science*, 254, 1497-1500 (1991).

O'Neil, I.A., et al., "The Synthesis of Functionalized Pyrrolo-[2,1-c][1,4]-Benzodiazepines," *Synlett*, 75-78 (1997).

O'Neil, Chemical Abstract No. 171573p, "The synthesis of Functionalized Pyrrolo-[2,1-c][1,4]-Benzodiazepines", *Chemical Abstracts*, vol. 126, No. 13, 618 (1997).

O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).

Paikoff, S.J. et al., "The Solid Phase Synthesis of N-Alkylcarbamate Oligomers", *Tetrahedron Letters*, 37, No. 32: 5653-5656 (1996).

Pillai, V.N.R., "Photoremovable protecting groups in organic chemistry," *Synthesis*, 1-26 (1980).

Ram, Z. et al., "In Situ Retroviral-mediated Gene Transfer for the Treatment of Brain Tumors in Rats," *Cancer Research*, 53, 83-88 (1993).

Rawal, V.H. et al., "Photocyclization Strategy for the Synthesis of Antitumor Agent CC-1065: Synthesis of Dideoxy PDE-I and PDE-II. Synthesis of Thiophene and Furan Analogues of Dideoxy PDE-I and PDE-II," *J. Org. Chem.*, 52, 19-28 (1987).

Reddy et al., "Design, synthesis and in vitro cytotoxicity studies of novel pyrrolo[2,1-c][1,4]benzodiazepine (PBD)-polyamide conjugates and 2,2'-PBD dimers," Anti-Cancer Drug Design (2000) 15(3):225-228.

Regula, J. et al., "Photosensitisation and photodynamic therapy of oesophagael, duodenal and colorectal tumours using 5-aminoleavulic acid induced photoporphyrin IX-a pilot study," *Gut*, 36, 67-75 (1995).

Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).

Saha, A.K. et al., "Diisopropylsilyl-Linked Oligonucleotide Analogs: Solid-Phase Synthesis and Physiocochemical Properties," *J. Org. Chem.*, 58, 7827-7831 (1993).

Satyam, A. et al., "Design, Synthesis, and Evaluation of Latent Alkylating Agents Activated by Glutathione *S*-Transferase," *J. Med. Chem.*, 39, 1736-1747 (1996).

Shimizu, K et al., "Prothracarcin, a Novel Antitumor Antibiotic," *J. Antibiotics*, 35, 972-978 (1982).

Simon, R.J. et al., "Peptoids, A Modular Approach to Drug Discovery", *Proc. Natl. Acad. Sci.* USA,89:9367-9371 (1992).

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Soth, M.J. and Nowick, J.S., "Unnatural oligomers and unnatural oligomer libraries", *Curr. Opin. Chem. Biol.*, 1:120-129 (1997).

Star, W.M., "Light delivery and light dosimetry for photodynamic therapy," *Lasers in Medical Science*, 5:107-113 (1990).

Suggs, J.W. et al., "Synthesis and structure of anthramycin analogs via hydride reduction of dilactams," *Tetrahedron Letters*, 26, No. 40, 4871-4874 (1985).

Takeuchi, T. et al., "Neothramycins A and B, New Antitumor Antibiotics," *J. Antibiotics*, 29, 93-96 (1976).

Tew, K.D. and Clapper, M.L., "Glutathione-S-tranferase and anti-cancer drug resistance," *Mechanism of Drug Resistance in*

*Neoplastic Cells*, Woolley, P.V. and Tew, K.D., Eds, Academic Press: Sand Diego, CA 141-159 (1988).

Thurston, D.E. and Thompson, A.S., "The molecular recognition of DNA," *Chem. Brit.*, 26, 767-772 (1990).

Thurston, D.E. and Bose, D.S., "Synthesis of DNA-Interactive Pyrrolo[2,1-c][1,4]benzodiazepines," *Chem. Rev.*, 94:433-465 (1994).

Thurston, D. E., "Advances in the study of Pyrrolo[2,1-c][1,4] benzodiazepine (PBD) Antitumour Antibiotics", *Molecular Aspects of Anticancer Drug-DNA Interaction*, Neidle, S. and Waring, M.J., Eds.; Macmillan Press Ltd, 1:54-88 (1993).

Thurston, D.E. et al., "Effect of A-ring modifications on the DNA-binding behavior and cytotoxicity of pyrrolo[2,1-c][1,4]benzodiazepines", *Journal of Medicinal Chemistry*, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).

Thurston, D.E. et al., "Synthesis of a novel GC-specific covalent-binding DNA affinity-cleavage agent based on pyrrolobenzodiazepines (PBDs)," Chemical Communications, 563-565 (1996).

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.

Tsunakawa, M. et al., "Porothramycin, a new antibiotic of the anthramycin group: Production, isolation, structure and biological activity," *J. Antibiotics*, 41:1366-1373 (1988).

Umezawa, H. et al., Chemical Abstract No. 4427a, "Mazethramycins" *Chemical Abstracts*, vol. 90, No. 1, 428 (1979).

Umezawa, H. et al., "Mazethramycins," *SciFinder Scholar*, 2-3 (2002).

Wells, G. et al., "Pyrrolobenzodiazepine-polyamide libraries: synthesis and DNA binding selectivity," Proc. Am. Assoc. Canc. Res. (2003) 44:85-86, #452.

Wermuth et al., "Molecular Variations Based on Isosteric Replacements," The Practice of Medicinal Chemistry, Chapter 13 (1996) 203-237.

Williams, M.A. et al., "Synthesis of conformationally constrained DTPA analogues. Incorporation of the ethylenediamine units as aminopyrrolidines," J. Org. Chem. (1994) 59(13):3616-3625.

Wilson, S.C. et al., "Design and Synthesis of a Novel Epoxide-Containing Pyrrolo[2,1-c][1,4]benzodiazepine (PBD) via a New Cyclization Procedure," *Tetrahedron Letters*, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", *J. Med. Chem.* 42:4028-4041 (1999).

Zuckerman, R.N. et al., "Discovery of Nanomolecular Ligands for 7-Transmembrane G-Protein-Coupled Receptors from a Diverse N-(Substituted) glycine Peptoid Library", *J. Med. Chem.*, 37:2678-2685 (1994).

PYRROLOBENZODIAZEPINES

CROSS REFERENCE TO RELATED APPLICATIONS

This application is a continuation of U.S. patent application Ser. No. 09/763,767, filed on Feb. 26, 2001 now U.S. Pat. No. 7,049,311 which is a filing under 35 U.S.C. 371 based upon International Application No. PCT/GB99/02838, filed on Aug. 27, 1999, which claims priority to Great Britain Application No. 9818733.9, filed Aug. 27, 1998 and Great Britain Application No. 9901929.1, filed on Jan. 28, 1999.

BACKGROUND OF THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber et al., 1965 *J. Am. Chem. Soc.*, 87, 5793-5795; Leimgruber et al., 1965 *J. Am. Chem. Soc.*, 87, 5791-5793). Since then, a number of naturally occurring PBDs have been reported, and over 10 synthetic routes have been developed to a variety of analogues (Thurston et al., 1994 *Chem. Rev.* 1994, 433-465). Family members include abbeymycin (Hochlowski et al., 1987 *J. Antibiotics*, 40, 145-148), chicamycin (Konishi et al., 1984 *J. Antibiotics*, 37, 200-206), DC-81 (Japanese Patent 58-180 487; Thurston et al., 1990, *Chem. Brit.*, 26, 767-772; Bose et al., 1992 *Tetrahedron*, 48, 751-758), mazethramycin (Kuminoto et al., 1980 *J. Antibiotics*, 33, 665-667), neothramycins A and B (Takeuchi et al., 1976 *J. Antibiotics*, 29, 93-96), porothramycin (Tsunakawa et al., 1988 *J. Antibiotics*, 41, 1366-1373), prothracarcin (Shimizu et al, 1982 *J. Antibiotics*, 29, 2492-2503; Langley and Thurston, 1987 *J. Org. Chem.*, 52, 91-97), sibanomicin (DC-102) (Hara et al., 1988 *J. Antibiotics*, 41, 702-704; Itoh et al., 1988 *J. Antibiotics*, 41, 1281-1284), sibiromycin (Leber et al., 1988 *J. Am. Chem. Soc.*, 110, 2992-2993) and tomamycin (Arima et al., 1972 *J. Antibiotics*, 25, 437-444). PBDs are of the general structure I:

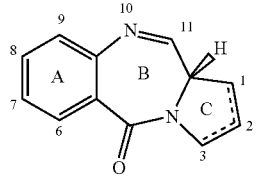

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In *Antibiotics III*. Springer-Verlag, New York, pp. 3-11; Hurley and Needham-VanDevanter, 1986 *Acc. Chem. Res.*, 19, 230-237). Their ability to form an adduct in the minor groove, enables them to interfere with DNA processing, hence their use as antitumour agents.

DISCLOSURE OF THE INVENTION

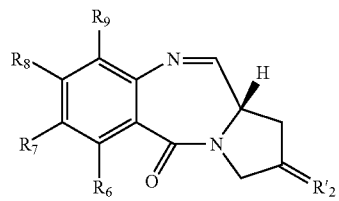

A first aspect of the present invention is a compound with the formula II:

wherein:

$R'_2$ is $CHR''_2$, where $R''_2$ is H.

$R_6$ and $R_9$ are H and $R_7$ is OMe and the compound is a dimer with each monomer being the same and being of formula II, where the $R_8$ groups of the monomers form together a bridge having the formula —O—$(CH_2)_p$—O—, where p is 5, linking the monomers.

A second aspect of the present invention is the use of a compound as described in the first aspect of the invention in a method of therapy. Conditions which may be treated include gene-based diseases, including, for example, neoplastic diseases and Alzheimer's Disease, and also bacterial, parasitic and viral infections. Any condition which may be treated by the regulation of gene expression may be treated using compounds of the invention. In accordance with this aspect of the present invention, the compounds provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated.

Pharmaceutical compositions according to the present invention, and for use in accordance with the present invention, may comprise, in addition to the active ingredient, i.e. a compound of formula II, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A third aspect of the present invention is a pharmaceutical composition containing a compound of formula II, as described above, and a pharmaceutically acceptable carrier or diluent. The preparation of pharmaceutical compositions is described in relation to the second aspect of the invention above.

A fourth aspect of the present invention provides the use of a compound of formula II as described above to prepare a medicament for the treatment of a gene-based disease, preferably a proliferative disease. The compound of formula II may be provided together with a pharmaceutically acceptable carrier or diluent. The compounds may be used for the selective killing of oxic and hypoxic tumour cells in methods for the treatment of cancers, for example leukemias and particularly solid cancers including colon, CNS, renal, and lung tumours, including small cell lung carcinoma, and melanomas. In particular, dimers of formula II may be used for the selective killing of lung, colon, and CNS tumours and melanomas.

A further aspect of the present invention provides the use of a compound of formula II as described above to prepare a medicament for the treatment of a viral, parasitic or bacterial infection. The preparation of a medicament is described in relation to the second aspect of the invention above.

In further aspects, the invention provides processes for preparing compounds according to the first aspect of the present invention.

BRIEF DESCRIPTION OF THE DRAWINGS

Aspects of the invention will now be further described with reference to the accompanying drawings in which.

PREFERRED GENERAL SYNTHETIC STRATEGIES

Figure 1:
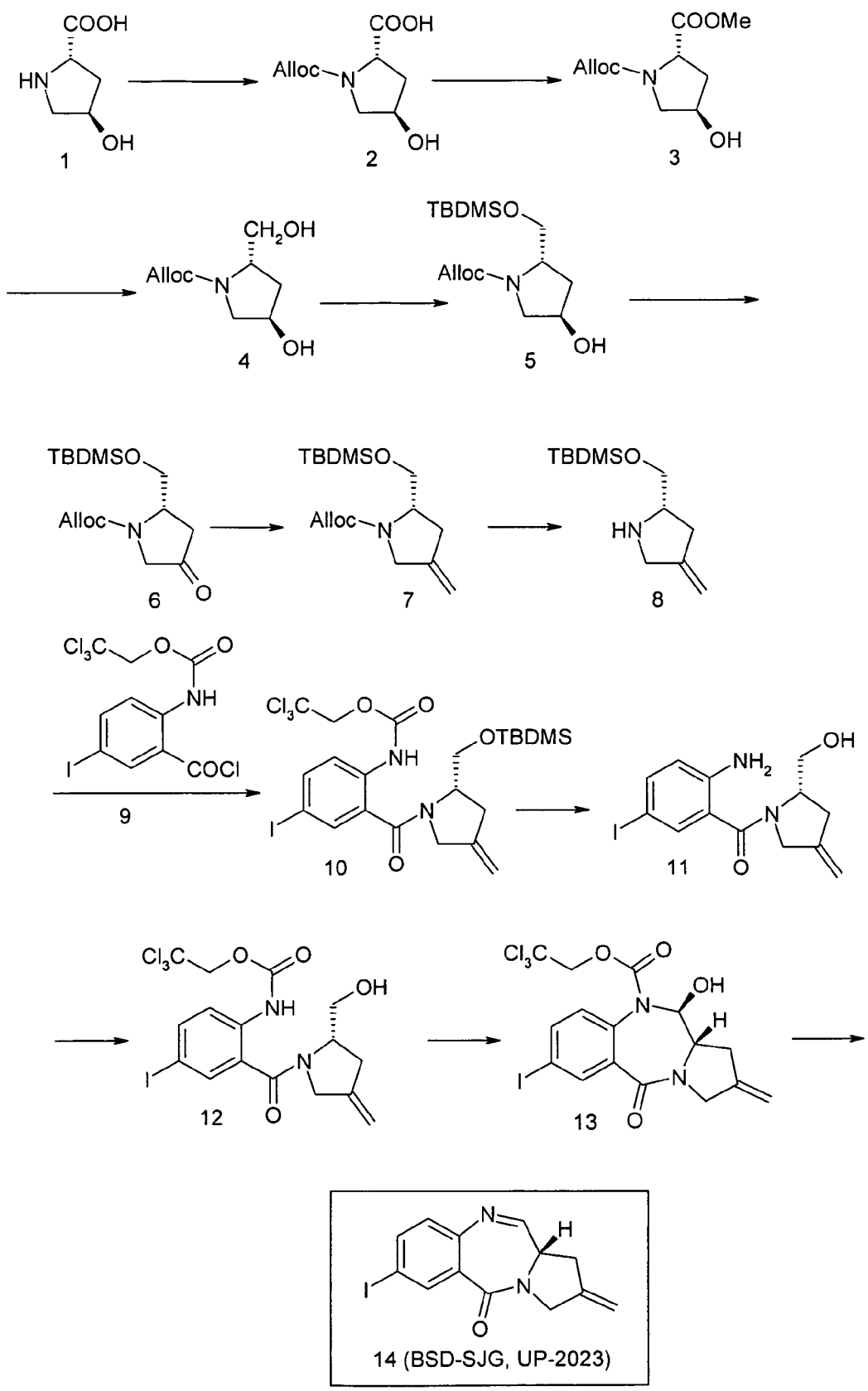
FIGS. 1-8 are synthesis routes for compounds of formula II.

A key step in a preferred route to compounds of formula II is a cyclisation to produce the B-ring, involving generation of an aldehyde (or functional equivalent thereof at what will be the 11-position, and attack thereon by the Pro-N10-nitrogen:

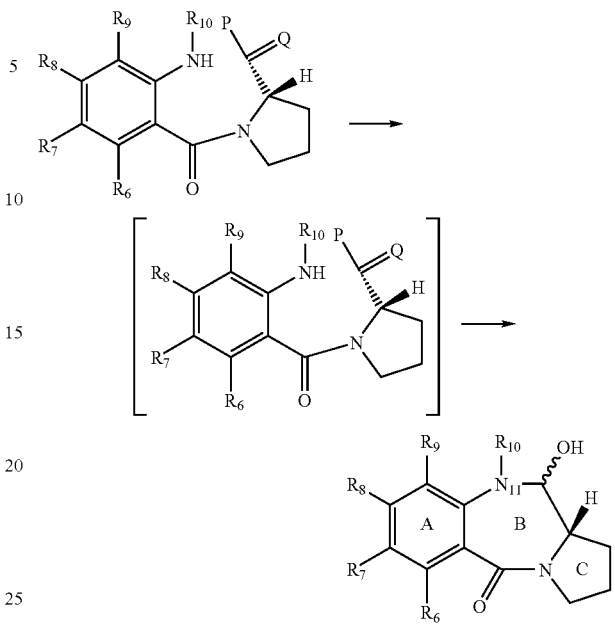

In this structure, no C-ring substitution or unsaturation is shown. $R_{10}$ is a nitrogen protecting group, preferably with a carbamate functionality bonded to the nitrogen of the PBD. The "masked aldehyde"-CPQ may be an acetal or thioacetal (possibly cyclic), in which case the cyclisation involves unmasking. Alternatively, the masked aldehyde may be an aldehyde precursor, such as alcohol —CHOH, in which case the reaction involves oxidation, e.g. by means of TPAP or DMSO (Swern oxidation).

The masked aldehyde compound can be produced by condensing a corresponding 2-substituted pyrrolidine with a 2-nitrobenzoic acid:

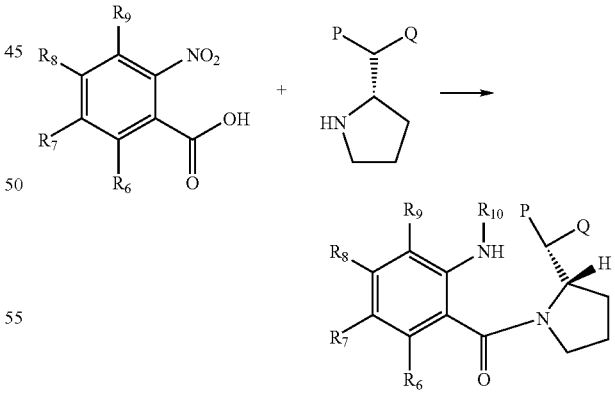

The nitro group can then be reduced to —$NH_2$ and protected by reaction with a suitable reagent, e.g. a chloroformate, which provides the removable nitrogen protecting group in the synthesis route.

A process involving the oxidation-cyclization procedure is illustrated in scheme 1 (an alternative type of cyclisation will be described later with reference to scheme 2).

Scheme 1

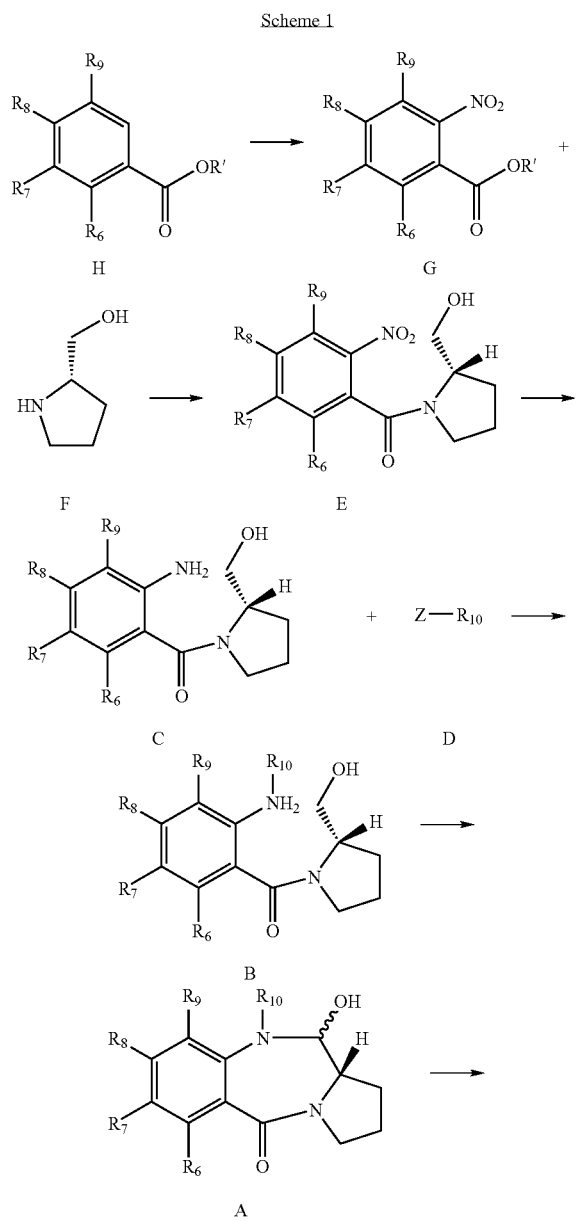

The imine/carbinolamine bond in the PBD (A) can be unprotected by standard methods to yield the desired compound, e.g. if $R_{10}$ is Alloc, then the deprotection is carried out using palladium to remove the N10 protecting group, followed by the elimination of water to give the imine.

Exposure of the alcohol (B) (in which the Pro-N10-nitrogen is generally protected as carbamate) to tetrapropylammonium perruthenate (TPAP)/N-methylmorpholine N-oxide (NMO) over A4 sieves results in oxidation accompanied by spontaneous B-ring closure to afford the desired product. The TPAP/NMO oxidation procedure is found to be particularly convenient for small scale reactions while the use of DMSO-based oxidation methods, particularly Swern oxidation, proves superior for larger scale work (e.g. >1 g).

The uncyclized alcohol (B) may be prepared by the reaction of a nitrogen protection reagent of formula D, which is preferably a chloroformate or acid chloride, to a solution of the amino alcohol C, generally in solution, generally in the presence of a base such as pyridine (preferably 2 equivalents) at a moderate temperature (e.g. at 0° C.). Under these conditions little or no O-acylation is usually observed.

The key amino alcohol C may be prepared by reduction of the corresponding nitro compound E, by choosing a method which will leave the rest of the molecule intact. Treatment of E with tin (II) chloride in a suitable solvent, e.g. refluxing methanol, generally affords, after the removal of the tin salts, the desired product in high yield.

Exposure of E to hydrazine/Raney nickel avoids the production of tin salts and may result in a higher yield of C, although this method is less compatible with the range of possible C and A-ring substituents. For instance, if there is C-ring unsaturation (either in the ring itself, or in $R_2$ or $R_3$), this technique may be unsuitable.

The nitro compound of formula E may be prepared by coupling the appropriate o-nitrobenzoyl chloride to a compound of formula F, e.g. in the presence of $K_2CO_3$ at −25° C. under a $N_2$ atmosphere. Compounds of formula F can be readily prepared, for example by olefination of the ketone derived from L-trans-hydroxy proline. The ketone intermediate can also be exploited by conversion to the enol triflate for use in palladium mediated coupling reactions.

The o-nitrobenzoyl chloride is synthesised from the o-nitrobenzoic acid (or alkyl ester after hydrolysis) of formula G, which itself is prepared from the vanillic acid (or alkyl ester) derivative H. Many of these are commercially available and some are disclosed in Althuis, T. H. and Hess, H. J., *J. Medicinal Chem.*, 20(1), 146-266 (1977).

Alternative Cyclisation (Scheme 2)

Scheme 2

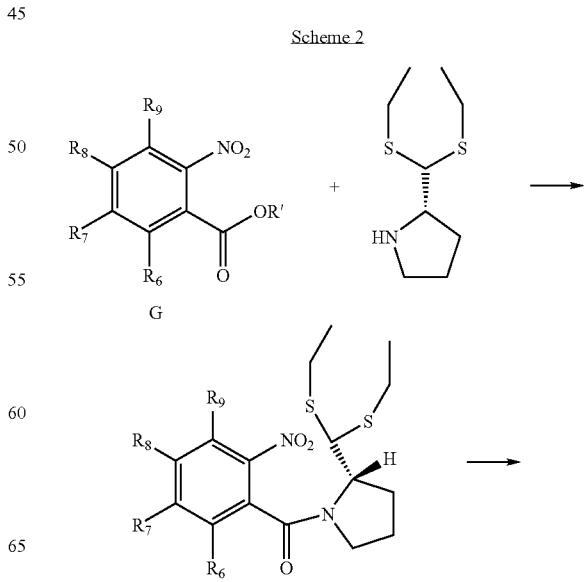

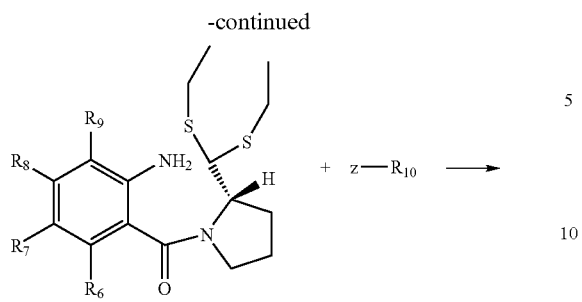
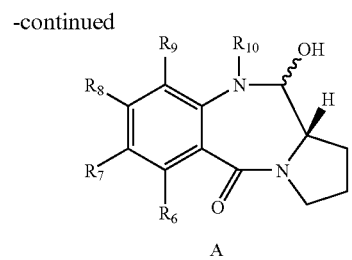

In scheme 1, the final or penultimate step was an oxidative cyclisation. An alternative, using thioacetal coupling, is shown in scheme 2. Mercury-mediated unmasking causes cyclisation to the protected PBD compound (A).

The thioacetal compound may be prepared as shown in scheme 2: the thioacetal protected C-ring [prepared via a literature method: Langley, D. R. & Thurston, D. E., *J. Organic Chemistry*, 52, 91-97 (1987)] is coupled to the o-nitrobenzoic acid (or alkyl ester after hydrolysis) (G) using a literature procedure. The resulting nitro compound cannot be reduced by hydrogenation, because of the thioacetal group, so the tin(II) chloride method is used to afford the amine. This is then N-protected, e.g., by reaction with a chloroformate or acid chloride, such as 2,2,2-trichloroethylchloroformate.

Acetal-containing C-rings can be used as an alternative in this type of route with deprotection involving other methods, including the use of acidic conditions.

Dimer Synthesis (Scheme 3)

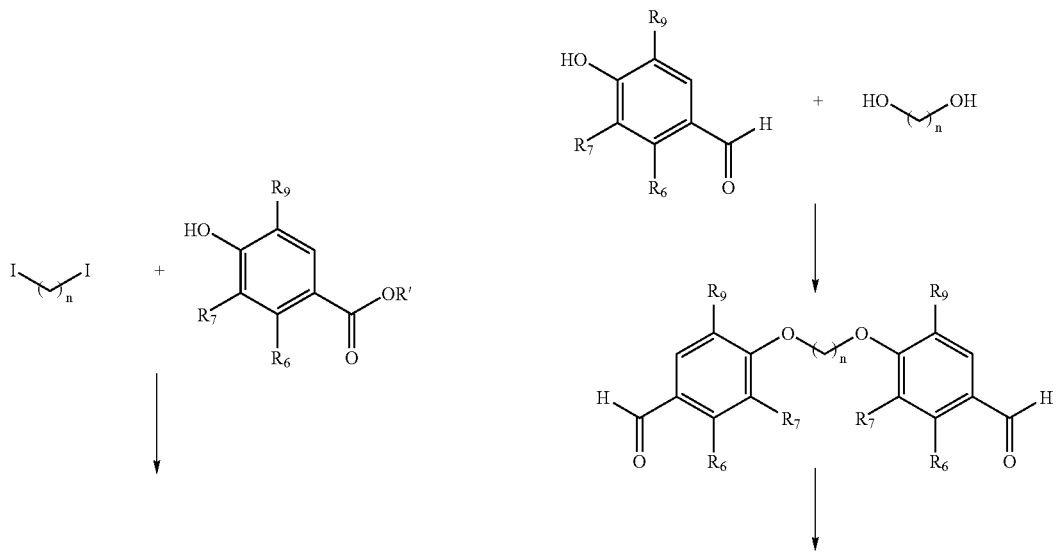

-continued

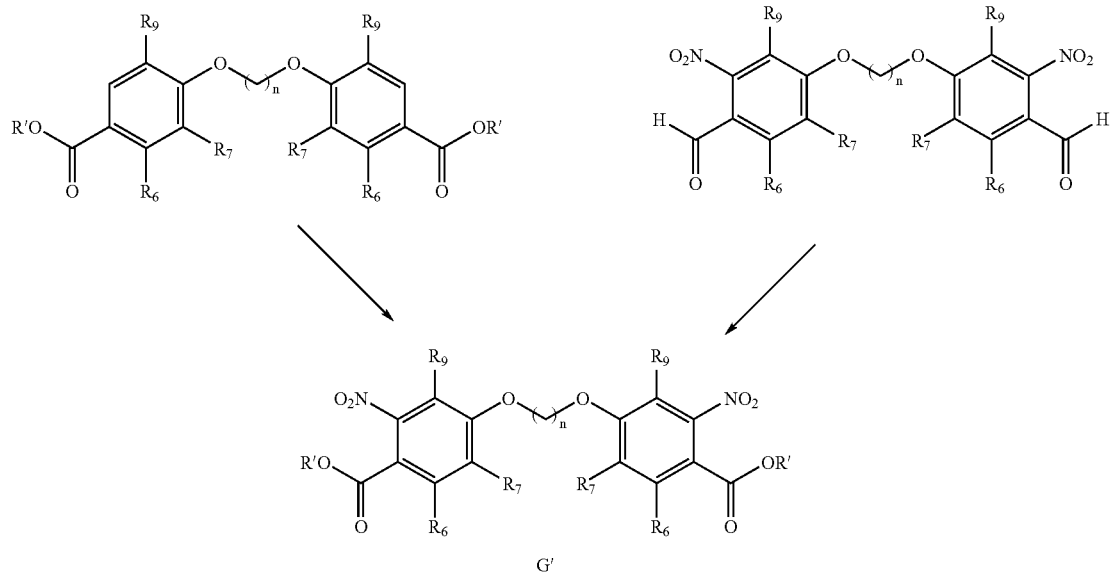

G'

PBD dimers may be synthesized using the strategy developed for the synthesis of protected PBD monomers. The synthesis routes illustrated in scheme 3 show compounds when the dimer linkage is of the formula —O—$(CH_2)_n$—O—. The step of dimer formation is normally carried out to form a bis(nitro acid) G'. This compound can then be treated as compound G in either scheme 1 or scheme 2 above.

The bis(nitro acid) G' may be obtained by nitrating (e.g. using 70% nitric acid) the bis(carboxylic acid). This can be synthesised by alkylation of two equivalents of the relevant benzoic acid with the appropriate diiodoalkane under basic conditions. Many benzoic acids are commercially available and others can be synthesised by conventional methods. Alternatively, the relevant benzoic acid esters can be joined together by a Mitsunobo etherification with an appropriate alkanediol, followed by nitration, and then hydrolysis (not illustrated).

An alternative synthesis of the bis(nitro acid) involves oxidation of the bis(nitro aldehyde), e.g. with potassium permanganate. This can be obtained in turn by direct nitration of the bis(aldehyde), e.g. with 70% $HNO_3$. Finally, the bis(aldehyde) can be obtained via the Mitsunobu etherification of two equivalents of the benzoic aldehyde with the appropriate alkanediol.

An alternative synthesis approach to those detailed above is to protect the pro N10 position on the component which will form the A-ring, before joining the component which will form the C-ring.

The alternative synthesis routes are equally applicable to the synthesis of dimers.

Preferred Synthesis Strategies for Compounds of Formula II

The synthesis route of scheme 1 is generally applicable to compounds of formula II.

C2-unsaturated PBDs of formula II may be synthesised from their N10-carbamate protected precursors. Typically, palladium catalysed removal of an allyl carbamate may be used to generate the N10-C11 imine without affecting the key C2-unsaturation. Alternatively, cadmium-lead couple may be employed to cleave an N10-2,2,2-trichloroethyl carbamate from the protected PBD.

The reduction of the nitro-compound E as shown in scheme 1 with tin (II) chloride maintains the C2-unsaturation, although isolating the aniline C from the tin salts can be problematic.

The compound of formula F may be used in its TBDMS protected form, and therefore a deprotection step has to be included to produce the amino-alcohol compound E.

The TBDMS ether of type E, which is the product of the coupling of the TBDMS protected compound with the appropriate o-nitrobenzoyl chloride, can be treated with AcOH:THF:$H_2O$ (3:1:1). TBAF was found to be unsuitable for this transformation due to the rapid degradation of reaction products.

C-ring providing compounds F(II) can be obtained as shown in scheme 4.

Scheme 4

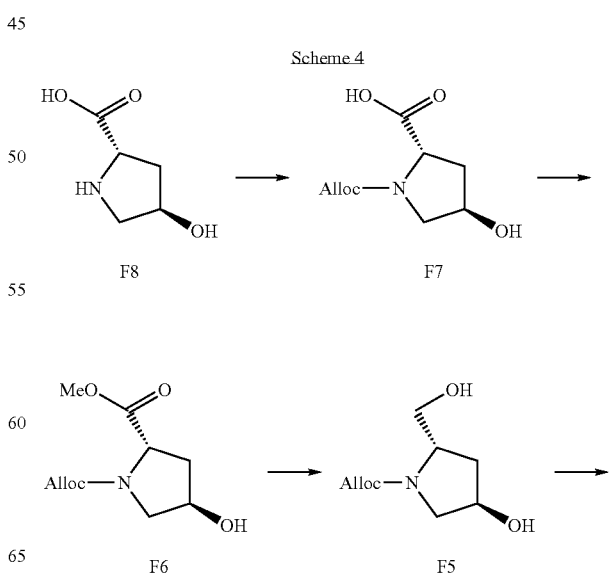

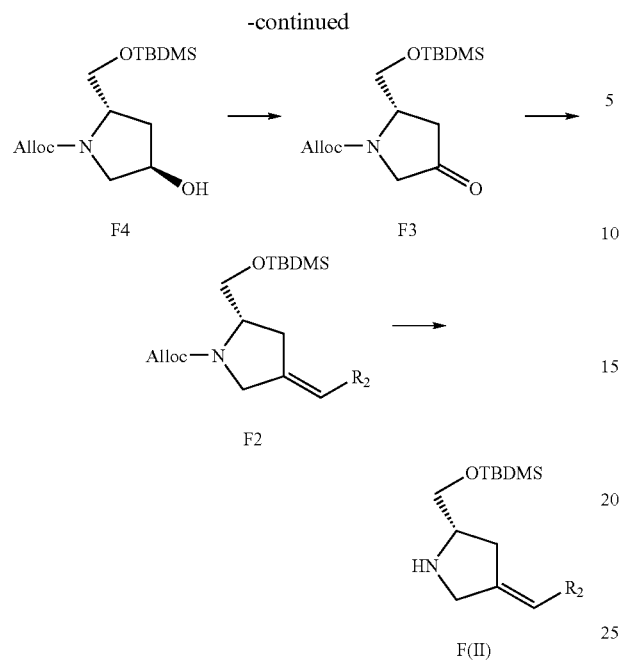

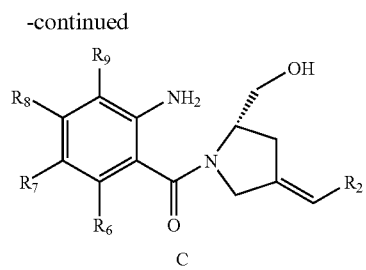

Commercially available trans-4-hydroxy-L-proline F8 can be N-alloc protected to give the allyl carbamate F7 which can then be esterified using standard conditions. Hydride reduction of the ester F6 furnishes the diol F5. Selective TBDMS protection of the diol gives a silyl ether F4, which can then be oxidised, using either Swern or TPAP oxidation, to provide the ketone F3.

The C2-olefinic functionality present in F2 may be introduced by performing the Wittig reaction on ketone F3. Palladium-mediated cleavage of the N-alloc protecting group (Dangles O.; Guibé, F.; Balavoine, G.; Lavielle, S.; Marquet, A.; *J. Org. Chem.* 1987, 52, 4984) yields compound F(II).

Alternative Route to Compound C

Scheme 5

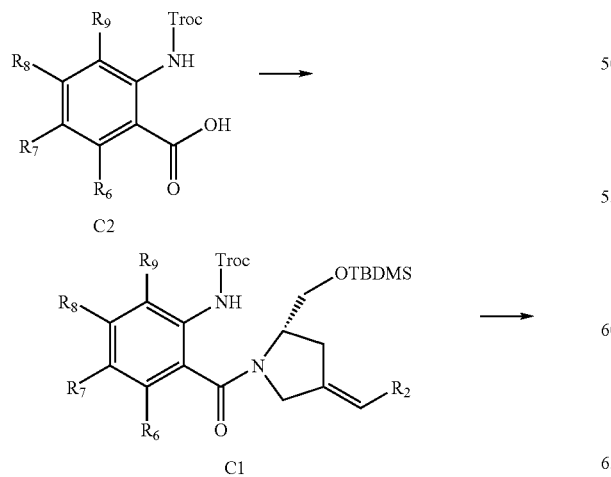

An alternative route to compound C has been developed (Scheme 5). The amide of formula C1 may be synthesised by forming the acid chloride of an N-Troc protected anthranilic acid of type C2. Interestingly, N-Troc anthranilic acids do not generate isatoic anhydrides, thus enabling amide formation reactions with amines of type F(II). Simultaneous TBAF-mediated cleavage of the 2,2,2-trichloroethyl carbamate and TBDMS groups from C1 may provide the key amino-alcohol C.

Alternative Route to Compounds of Formula II

Scheme 6

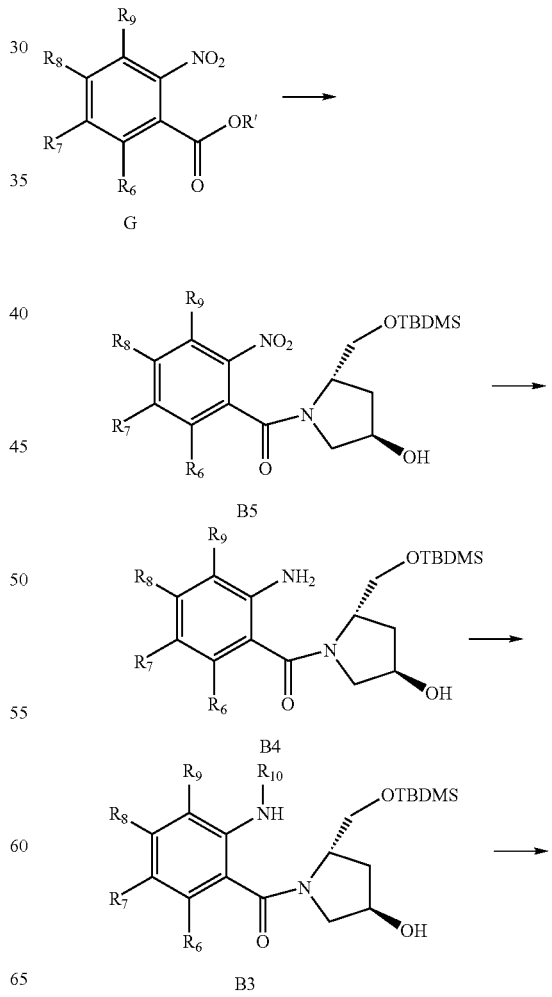

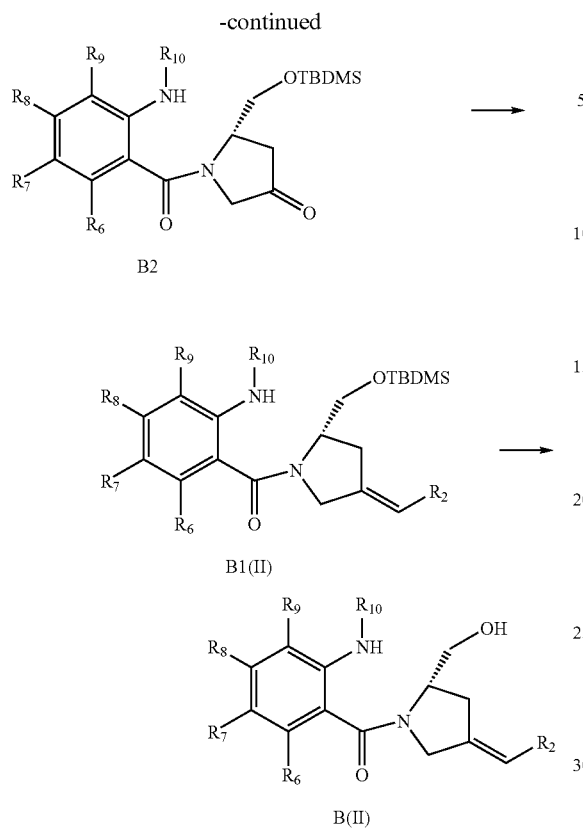
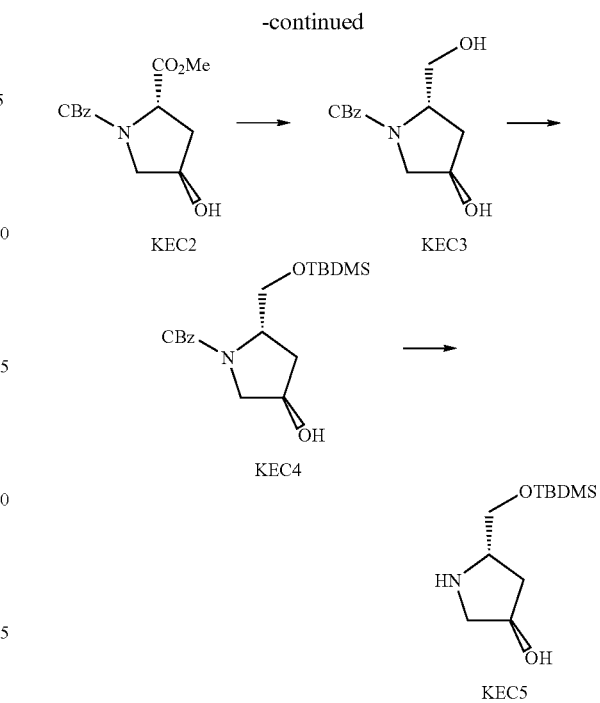

A more linear synthetic route to compound B of scheme 1 has been developed which enables larger scale production of the C2-unsaturated PBDs, and is shown in scheme 6. TBAF-mediated cleavage of the TBDMS group may be used to produce B(II) from B1(II). The key C2-unsaturation present in B1(II) may be introduced by performing the Wittig olefination reaction on a ketone of type B2. Swern oxidation of the secondary alcohol B3 may be used to furnish the ketone B2. The carbamate protected aniline B3 may be prepared from the nitro compound B5 in two steps. Firstly, the nitro group may be reduced to the aniline by employing the Raney nickel/hydrazine method because a compound of type B5 lacks C2-unsaturation. This method is more advantageous than the tin (II) chloride procedure since the product is easier to isolate. The aniline B4 may then be N-carbamate protected in high yield without significant carbonate formation at the C2 oxygen.

An amide of type B5 may be synthesised by coupling an acid chloride of type G to the key amine KEC5 (Scheme 7).

Scheme 7

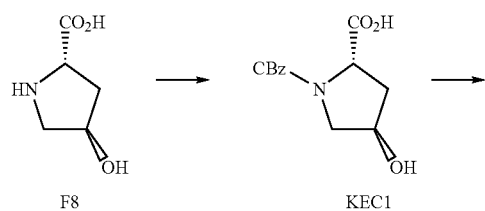

Overall, this route has several advantages over the convergent route which allow larger scale production of the C2-unsaturated PBDs. Firstly, catalytic hydrogenation of KEC4 allows large scale preparation of key intermediate KEC5. Secondly, the nitro reduction step may be carried out on an intermediate devoid of C2-unsaturation. Finally, the Wittig olefination may be performed in the latter stages of the synthetic route where large scale limitations are tolerated.

In dimer synthesis, the routes set out above may be used in preference to those set out in the overall synthetic strategies. In particular, the nitrogen-protecting group may advantageously be a carbamate, as protecting groups of this type may be removed in the final step by a variety of methods which, in general, do not affect the key C2-unsaturation.

General Experimental Methods

Melting points (mp) were determined on a Gallenkamp P1384 digital melting point apparatus and are uncorrected. Infrared (IR) spectra were recorded using a Perkin-Elmer 297 spectrophotometer. $^{1}$H- and $^{13}$C-NMR spectra were recorded on a Jeol GSX 270 MHZ FT-NMR spectrometer operating at 20° C. +/−1° C. Chemical shifts are reported in parts per million (δ) downfield from tetramethylsilane (TMS). Spin multiplicities are described as: s (singlet), bs (broad singlet), d (doublet), dd (doublet of doublets), t (triplet), q (quartet), p (pentuplet) or m (multiplet). Mass spectra (MS) were recorded using a Jeol JMS-DX 303 GC Mass Spectrometer (EI mode: 70 eV, source 117-147° C.). Accurate molecular masses (HRMS) were determined by peak matching using perfluorokerosene (PFK) as an internal mass marker, and FAB mass spectra were obtained from a glycerol/thioglycerol/trifluoroacetic acid (1:1:0.1) matrix with a source temperature of 180° C. Optical rotations at the Na-D line were obtained at ambient temperature using a Perkin-Elmer 141 Polarimeter. Analytical results were generally within +/−0.2% of the theoretical values. Flash chromatography was performed using Aldrich flash chromatography "Silica Gel-60" (E. Merck, 230-400 mesh). Thin-layer chromatography (TLC) was performed using GF$_{254}$ silica gel (with fluorescent indicator) on glass plates. All solvents and reagents, unless otherwise stated, were supplied by the Aldrich Chemical Company Ltd. and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

EXAMPLES

Example 1(a)

Synthesis of the C7-Iodo-C2-methlene PBD Monomer BSD-SJG (14, UP-2023) (see FIG. 1)

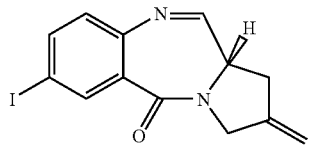

(2S,4R)-N-(Allyloxycarbonyl)-4-hydroxypyrrolidine-2-carboxylic acid (2) A solution of allyl chloroformate (29.2 mL, 33.2 g, 275 mmol) in THF (30 mL) was added dropwise to a suspension of trans-4-hydroxy-L-proline (1) (30 g, 229 mmol) in a mixture of THF (150 mL) and H$_2$O (150 mL) at 0° C. (ice/acetone), whilst maintaining the pH at 9 with 4 N NaOH. After stirring at 0° C. for 1 hour at pH 9, the aqueous layer was saturated with NaCl, and the mixture diluted with EtOAc (100 mL). The aqueous layer was separated, washed with EtOAc (100 mL) and the pH adjusted to 2 with conc. HCl. The resulting milky emulsion was extracted with EtOAc (2×100 mL), washed with brine (200 mL), dried (MgSO$_4$), filtered and evaporated in vacuo to give the allyl carbamate 2 as a clear viscous oil (42.6 g, 87%): $[\alpha]^{20}_D=-62.1°$ (c=0.69, MeOH); $^1$H NMR (270 MHz, CDCl$_3$+DMSO-d$_6$) (Rotamers) δ 5.98-5.81 (m, 1H, NCO$_2$CH$_2$CH=CH$_2$), 5.40-5.14 (m, 2H, NCO$_2$CH$_2$CH=CH$_2$), 4.64-4.42 (m, 4H, NCO$_2$CH$_2$CH=CH$_2$, NCH$_2$CHOHCH$_2$ and CHCO$_2$H), 3.82-3.51 (m, 2H, NCH$_2$CHOHCH$_2$), 2.34-2.08 (m, 2H, NCH$_2$CHOHCH$_2$); $^{13}$C NMR (67.8 MHz, CDCl$_3$+DMSO) (Rotamers) δ 175.0 and 174.5 (CO$_2$H), 155.1 and 154.6 (NC=O), 132.9 and 132.8 (NCO$_2$CH$_2$CH=CH$_2$), 117.6 and 116.7 (NCO$_2$CH$_2$CH=CH$_2$), 69.5 and 68.8 (NCH$_2$CHOH), 65.9 and 65.8 (NCO$_2$CH$_2$CH=CH$_2$), 58.0 and 57.7 (CHCO$_2$H), 55.0 and 54.5 (NCH$_2$CHOH), 39.3 and 38.3 (NCH$_2$CHOHCH$_2$); MS (EI), m/z (relative intensity) 215 (M+., 10) 197(12), 170 (M-CO$_2$H, 100), 152 (24), 130 (M-CO$_2$C$_3$H$_5$, 97), 126 (34), 112 (50), 108 (58), 86 (11), 68 (86), 56 (19); IR (Neat) 3500-2100 (br, OH), 2950, 1745 and 1687 (br, C=O), 1435, 1415, 1346, 1262, 1207, 1174, 1133, 1082, 993, 771 cm1; exact mass calcd for C$_9$H$_{13}$NO$_5$ m/e 215.0794, obsd m/e 215.0791.

Methyl (2S,4R)-N-(Allyloxycarbonyl)-4-hydroxy-pyrrolidine-2-carboxylate (3)

A catalytic amount of concentrated H$_2$SO$_4$ (4.5 mL) was added to a solution of Alloc-hydroxyproline (2) (43 g, 200 mmol) in MeOH (300 mL) at 10° C. (ice) and the reaction mixture was then heated at reflux for 2 h. After cooling to room temperature the reaction mixture was treated with TEA (43 mL) and the MeOH evaporated in vacuo. The residue was dissolved in EtOAc (300 mL), washed with brine (200 mL), dried (MgSO$_4$), filtered and concentrated in vacuo to give a viscous oil. Purification by flash chromatography (40% EtOAc/Petroleum Ether) removed the high Rf impurity to provide the pure ester 3 as a transparent yellow oil (19.6 g, 43%): $[\alpha]^{23}_D=-79.0°$ (c=0.35, CHCl3); $^1$H NMR (270 MHz, CDCl$_3$) (Rotamers) δ 5.98-5.78 (m, 1H, NCO$_2$CH$_2$CH=CH$_2$), 5.35-5.16 (m, 2H, NCO$_2$CH$_2$CH=CH$_2$), 4.65-4.45 (m, 4H, NCO$_2$CH$_2$CH=CH$_2$, NCH$_2$CHOHCH$_2$ and NCHCO$_2$CH$_3$), 3.75 and 3.72 (s×2, 3H, OCH$_3$), 3.70-3.54 (m, 2H, NCH$_2$CHOHCH$_2$), 3.13 and 3.01 (br s×2, 1H, OH), 2.39-2.03 (m, 2H, NCH$_2$CHOHCH$_2$); $^{13}$C NMR (67.8 MHz, CDCl$_3$) (Rotamers) δ 173.4 and 173.2 (CO$_2$CH$_3$), 155.0 and 154.6 (NC=O), 132.6 and 132.4 (NCO$_2$CH$_2$CH=CH$_2$), 117.6 and 117.3 (NCO$_2$CH$_2$CH=CH$_2$), 70.0 and 69.2 (NCH$_2$CHOH), 66.2 (NCO$_2$CH$_2$CH=CH$_2$), 57.9 and 57.7 (NCHCO$_2$CH$_3$), 55.2 and 54.6 (NCH$_2$CHOH), 52.4 (OCH$_3$), 39.1 and 38.4 (NCH$_2$CHOHCH$_2$); MS (EI), m/z (relative intensity) 229 (M$^+$, 7), 170 (M-CO$_2$Me, 100), 144 (M-CO$_2$C$_3$H$_5$, 12), 126 (26), 108 (20), 68 (7), 56 (8); IR (Neat) 3438 (br, OH), 2954, 1750 and 1694 (br, C=O), 1435, 1413, 1345, 1278, 1206, 1130, 1086, 994, 771 cm$^{-1}$; exact mass calcd for C$_{10}$H$_{15}$NO$_5$ m/e 229.0950, obsd m/e 229.0940.

(2S,4R)-N-(Allyloxycarbonyl)-4-hydroxy-2-(hydroxymethyl) pyrrolidine (4)

A solution of the ester 3 (19.5 g, 85 mmol) in THF (326 mL) was cooled to 0°C (ice/acetone) and treated with LiBH$_4$ (2.78 g, 128 mmol) in portions. The reaction mixture was allowed to warm to room temperature and stirred under a nitrogen atmosphere for 2.5 hours at which time TLC (50% EtOAc/Petroleum Ether) revealed complete consumption of ester 3. The mixture was cooled to 0° C. and water (108 mL) was carefully added followed by 2 N HCl (54 mL). After evaporation of the THF in vacuo, the mixture was neutralised to pH 7 with 10 N NaOH and saturated with solid NaCl. The saturated aqueous solution was then extracted with EtOAc (5×100 mL), the combined organic layers washed with brine (200 mL), dried (MgSO$_4$), filtered and evaporated in vacuo to furnish the pure diol 4 as a clear colourless oil (16.97 g, 99%): $[\alpha]^{24}_D=-57.0°$ (c=0.61, CHCl$_3$); $^1$H NMR (270 MHz, CDCl$_3$) δ 6.01-5.87 (m, 1H, NCO$_2$CH$_2$CH=CH$_2$), 5.36-5.20 (m, 2H, NCO$_2$CH$_2$CH=CH$_2$), 4.84 (br s, 1H, NCHCH$_2$OH), 4.60 (d, 2H, J=5.31 Hz, NCO$_2$CH$_2$CH=CH$_2$), 4.39 (br s, 1H, NCHCH$_2$OH), 4.18-4.08 (m, 1H, 3.35, NCH$_2$CHOH), 3.90-3.35 (m, 4H, NCH$_2$CHOH, NCHCH$_2$OH, and OH), 3.04 (brs, 1H, OH), 2.11-2.03 (m, 1H, NCH$_2$CHOHCH$_2$), 1.78-1.69 (m, 1H, NCH$_2$CHOHCH$_2$); $^{13}$C NMR (67.8 MHz, CDCl$_3$) δ 157.1 (NC=O), 132.6 (NCO$_2$CH$_2$CH=CH$_2$), 117.7 (NCO$_2$CH$_2$CH=CH$_2$), 69.2 (NCH$_2$CHOH), 66.4 and 66.2 (NCO$_2$CH$_2$CH=CH$_2$ and NCHCH$_2$OH), 59.2 (NCHCH$_2$OH), 55.5 (NCH$_2$CHOH), 37.3 (NCH$_2$CHOHCH$_2$); MS (EI), m/z (relative intensity) 201 (M$^+$, 2), 170 (M-CH$_2$OH, 100), 144 (M-OC$_3$H$_5$, 6), 126 (26), 108 (20), 68 (9); IR (Neat) 3394 (br, OH), 2946, 2870, 1679 (C=O), 1413, 1339, 1194, 1126, 1054, 980, 772 cm$^{-1}$; exact mass calcd for C$_9$H$_{15}$NO$_4$ m/e 201.1001, obsd m/e 201.1028

(2S,4R)-N-(Allyloxycarbonyl)-2-(tert-butyidimethylsilyloxymethyl)-4-hydroxypyrrolidine (5)

A solution of the diol 4 (16.97 g, 84 mmol) in CH$_2$Cl$_2$ (235 mL) was treated with TEA (11.7 mL, 8.5 g, 84 mmol) and stirred for 15 minutes at room temperature. TBDMSCl (9.72 g, 64 mmol) and DBU (16.8 mmol, 2.51 mL, 2.56 g) were added and the reaction mixture stirred for a further 16 hours under a nitrogen atmosphere. The reaction mixture was diluted with EtOAc (500 mL), washed with saturated NH$_4$Cl (160 mL), brine (160 mL), dried (MgSO$_4$), filtered and evaporated in vacuo to give an oil which was a mixture of the required product (major component), unreacted diol and the presumed disilyated compound by TLC (50% EtOAc/Petroleum Ether). Flash chromatography (20-100% EtOAc/Petroleum Ether) isolated the three components, to provide the monosilylated compound 5 as a slightly yellow transparent oil (13.85 g, 52%): [α]$^{21}_D$=−58.6° (c=1.14, CHCl3); $^1$H NMR (270 MHz, CDCl$_3$) (Rotamers) δ 6.01-5.86 (m, 1H, NCO$_2$CH$_2$CH=CH$_2$), 5.34-5.18 (m, 2H, NCO$_2$CH$_2$CH=CH$_2$), 4.59-4.49 (m, 3H, NCO$_2$CH$_2$CH=CH$_2$ and NCHCH$_2$OTBDMS), 4.06-3.50 (m, 5H, NCH$_2$CHOH, NCH$_2$CHOH and NCHCH$_2$OTBDMS), 2.20-2.01 (m, 2H, NCH$_2$CHOHCH$_2$), 0.87 (s, 9H, SiC(CH$_3$)$_3$), 0.0 (s, 6H, Si(CH$_3$)$_2$); $^{13}$C NMR (67.8 MHz, CDCl$_3$) (Rotamers) δ 155.0 (NC=O), 133.1 (NCO$_2$CH$_2$CH=CH$_2$), 117.6 and 117.1 (NCO$_2$CH$_2$CH=CH$_2$), 70.3 and 69.7 (NCH$_2$CHOH), 65.9 and 65.6 (NCO$_2$CH$_2$CH=CH$_2$), 63.9 and 62.8 (NCHCH$_2$OTBDMS), 57.8 and 57.4 (NCHCH$_2$OTBDMS), 55.7 and 55.2 (NCH$_2$CHOH), 37.3 and 36.6 (NCH$_2$CHOHCH$_2$), 25.9 (SiC(CH$_3$)$_3$), 18.2 (SiC(CH$_3$)$_3$), −5.5 (Si(CH$_3$)$_2$); MS (EI), m/z (relative intensity) 316 (M$^+$+1, 29), 315 (M$^+$, 4), 300 (M-CH$_3$, 26), 284 (4), 261 (8), 260 (50), 259 (100), 258 (M-OC$_3$H$_5$or M-$^t$Bu, 100), 218 (13), 215(10), 214 (52), 200 (12), 170 (M-CH$_2$OTBDMS, 100), 156 (40), 126 (58), 115 (33), 108 (41), 75 (35); IR (Neat) 3422 (br, OH), 2954, 2858, 1682 (C=O), 1467, 1434, 1412 (SiCH$_3$), 1358, 1330, 1255 (SiCH$_3$), 1196, 1180, 1120, 1054, 995, 919, 837, 776, 669 cm$^{-1}$; exact mass calcd for C$_{15}$H$_{29}$NO$_4$Si m/e 315.1866, obsd m/e 315.1946.

(2S)-N-(Allyloxycarbonyl)-2-(tert-butyldimethylsilyloxymethyl)-4-oxopyrrolidine (6)

Method A: A solution of DMSO (12.9 mL, 14.3 g, 183 mmol) in CH$_2$Cl$_2$ (90 mL) was added dropwise to a solution of oxalyl chloride (45.1 mL of a 2.0 M solution in CH$_2$Cl$_2$, 90.2 mmol) at −60° C. (dry ice/acetone) under a nitrogen atmosphere. After stirring at −70° C. for 30 minutes, a solution of the alcohol 5 (25.8 g, 81.9 mmol) dissolved in CH$_2$Cl$_2$ (215 mL) was added dropwise at −60° C. After 1.5 hours at −70° C., the mixture was treated dropwise with TEA (57.2 mL, 41.5 g, 410 mmol) and allowed to warm to 10° C. The reaction mixture was treated with brine (150 mL) and acidified to pH 3 with conc. HCl. The layers were separated and the organic phase washed with brine (200 mL), dried (MgSO$_4$), filtered and concentrated in vacuo to give an orange oil. Purification by flash chromatography (40% EtOAc/Petroleum Ether) furnished the ketone 6 as a pale yellow oil (24.24 g, 95%):

Method B: A solution of the alcohol 5 (4.5 g, 14.3 mmol) in CH$_2$Cl$_2$ (67.5 mL) was treated with CH$_3$CN (7.5 mL), 4 Å powdered molecular sieves (3.54 g) and NMO (2.4 g, 20.5 mmol). After 15 minutes stirring at room temperature, TPAP (0.24 g, 0.7 mmol) was added to the reaction mixture and a colour change (green→black) was observed. The reaction mixture was allowed to stir for a further 2.5 hours at which time complete consumption of starting material was observed by TLC (50% EtOAc/Petroleum ether 40°-60°). The black mixture was concentrated in vacuo and the pure ketone 6 was obtained by flash chromatography (50% EtOAc/Petroleum Ether) as a golden oil (4.1 g, 92%): [α]$^{22}_D$=+1.25° (c=10.0, CHCl3); $^1$H NMR (270 MHz, CDCl$_3$) (Rotamers) δ 6.0-5.90 (m, 1H, NCO$_2$CH$_2$CH=CH$_2$), 5.35-5.22 (m, 2H, NCO$_2$CH$_2$CH=CH$_2$), 4.65-4.63 (m, 2H, NCO$_2$CH$_2$CH=CH$_2$), 4.48-4.40 (m, 1H, NCHCH$_2$OTBDMS), 4.14-3.56 (m, 4H, NCH$_2$C=O and NCHCH$_2$OTBDMS), 2.74-2.64 (m, 1H, NCH$_2$C=OCH$_2$), 2.46 (d, 1H, J=18.69 Hz, NCH$_2$C=OCH$_2$), 0.85 (s, 9H, SiC(CH$_3$)$_3$), 0.0 (s, 6H, Si(CH$_3$)$_2$); $^{13}$C NMR (67.8 MHz, CDCl$_3$) (Rotamers) δ 210.1 (C=O), 154.1 (NC=O), 132.7 (NCO$_2$CH$_2$CH=CH$_2$), 118.0 and 117.7 (NCO$_2$CH$_2$CH=CH$_2$), 66.0 and 65.8 (NCO$_2$CH$_2$CH=CH$_2$), 65.0 (NCHCH$_2$OTBDMS), 55.7 (NCHCH$_2$OTBDMS), 53.6 (NCH$_2$C=O), 40.8 and 40.1 (NCH$_2$C=OCH$_2$), 25.7 (SiC(CH$_3$)$_3$), 18.1 (SiC(CH$_3$)$_3$), −5.7 and −5.8 (Si(CH$_3$)$_2$); MS (CI), m/z (relative intensity) 314 (M$^+$+1, 100), 256 (M-OC$_3$H$_5$ or M-$^t$Bu, 65); IR (Neat) 2930, 2858, 1767 (C=O), 1709 (NC=O), 1409 (SiCH$_3$), 1362, 1316, 1259 (SiCH$_3$), 1198, 1169, 1103, 1016, 938, 873, 837, 778, 683 cm$^{-1}$; exact mass calcd for C$_{15}$H$_{27}$NO$_4$Si m/e 313.1710, obsd m/e 313.1714.

(S)-N-(Allyloxycarbonyl)-2-(tert-butyidimethylsilyloxymethyl)-4-methylidenepyrrolidine (7)

Potassium tert-butoxide (41.0 mL of a 0.5 M solution in THF, 20.5 mmol) was added dropwise to a suspension of methyltriphenylphosphonium bromide (7.29 g, 20.4 mmol) in THF (20 mL) at 0° C. (ice/acetone) under nitrogen. After stirring for 2 hours at 0° C., a solution of the ketone 6 (3.20 g, 10.2 mmol) in THF (10 mL) was added dropwise and the mixture allowed to warm to room temperature. After stirring for a further 30 minutes the reaction mixture was diluted with EtOAc (150 mL) and water (150 mL) and the organic layer separated, washed with brine, dried (MgSO$_4$), filtered and evaporated in vacuo to give a yellow oil in which crystals (TPO) formed upon standing in the freezer. Purification by flash chromatography (5% EtOAc/Petroleum Ether) isolated the pure olefin 7 as a colourless oil (2.76 g, 87%): [α]$^{21}_D$=−22.2° (c=0.25, CHCl$_3$); $^1$H NMR (270 MHz, CDCl$_3$) (Rotamers) δ 6.02-5.87 (m, 1H, NCO$_2$CH$_2$CH=CH$_2$), 5.31 (ddd, 1H, J=1.65, 3.11, 17.20 Hz, NCO$_2$CH$_2$CH=CH$_2$), 5.21 (dd, 1H, J=1.46, 10.40 Hz, NCO$_2$CH$_2$CH=CH$_2$), 4.99-4.61 (m, 2H, NCH$_2$C=CH$_2$), 4.60 (d, 2H, J=4.94 Hz, NCO$_2$CH$_2$CH=CH$_2$), 4.19-3.98 (m, 2H, NCHCH$_2$OTBDMS), 3.93-3.87 (m, 1H, NCHCH$_2$OTBDMS), 3.66-3.42 (m, 2H, NCH$_2$C=CH$_2$), 2.80-2.56 (m, 2H, NCH$_2$C=CH$_2$CH$_2$), 0.87 (s, 9H, SiC(CH$_3$)$_3$), 0.03-0.02 (m, 6H, Si(CH$_3$)$_2$); $^{13}$C NMR (67.8 MHz, CDCl$_3$) (Rotamers) δ 154.4 (NC=O), 145.1 and 144.1 (NCH$_2$C=CH$_2$), 133.1 (NCO$_2$CH$_2$CH=CH$_2$), 117.5 and 117.2 (NCO$_2$CH$_2$CH=CH$_2$), 107.5 and 106.9 (NCH$_2$C=CH$_2$), 65.8 and 65.6 (NCO$_2$CH$_2$CH=CH$_2$), 63.7 and 63.1 (NCHCH$_2$OTBDMS), 58.7 and 58.3 (NCHCH$_2$OTBDMS), 51.1 (NCH$_2$C=CH$_2$), 34.9 and 34.2 (NCH$_2$C=CH$_2$CH$_2$), 25.8 (SiC(CH$_3$)$_3$), 18.2 (SiC(CH$_3$)$_3$), −5.5 (Si(CH$_3$)$_2$); MS (CI), m/z (relative intensity) 312 (M$^+$+1, 82), 296 (9), 279 (5), 255 (20), 254 (M-OC$_3$H$_5$or M-$^t$Bu, 100), 168 (8), 122 (14); IR (Neat) 3083 (C=CH$_2$), 2954, 2847, 1709 (NC=O), 1533, 1467, 1404 (SiCH$_3$), 1360, 1310, 1252 (SiCH$_3$), 1207, 1174, 1103, 1076, 1006, 836, 776, 680 cm$^{-1}$.

(2S)-2-(tert-butyldimethylsilyloxymethyl)-4-methylidenepyrrolidine (8)

A catalytic amount of PdCl$_2$(PPh$_3$)$_2$ (92 mg, 0.131 mmol) was added to a solution of the allyl carbamate 7 (1.0 g, 3.22 mmol) and H$_2$O (0.34 mL, 18.9 mmol) in CH$_2$Cl$_2$ (30 mL). After 5 minutes stirring at room temperature, Bu$_3$SnH (0.96 mL, 1.04 g, 3.57 mmol) was added rapidly in one portion. A slightly exothermic reaction with vigorous gas evolution immediately ensued. The mixture was stirred for 16 hours at room temperature under nitrogen at which point TLC (50% EtOAc/Petroleum Ether) revealed the formation of amine. After diluting with CH$_2$Cl$_2$ (30 mL), the organic solution was dried (MgSO$_4$), filtered and evaporated in vacuo to give an orange oil which was purified by flash chromatography (50-100% EtOAc/Petroleum Ether) to afford the amine 8 as a slightly orange oil (0.56 g, 77%): [α]$^{21}_D$=−3.9° (c=5.0, CHCl$_3$); $^1$H NMR (270 MHz, CDCl$_3$) δ 4.93 (t, 1H, J=2.02 Hz, NCH$_2$C=CH$_2$), 4.90 (t, 1H, J=2.02 Hz, NCH$_2$C=CH$_2$), 3.68-3.46 (m, 4H, NCHCH$_2$OTBDMS and NCH$_2$C=CH$_2$), 3.30-3.21 (m, 1H, NCHCH$_2$OTBDMS), 2.53-2.41 (m, 2H, NCH$_2$C=CH$_2$CH$_2$ and NH), 2.26-2.17 (m, 1H, NCH$_2$C=CH$_2$CH$_2$), 0.90 (s, 9H, SiC(CH$_3$)$_3$), 0.06 (s, 6H, Si(CH$_3$)$_2$); $^{13}$C NMR (67.8 MHz, CDCl$_3$) δ 150.0 (NCH$_2$C=CH$_2$), 104.7 (NCH$_2$C=CH$_2$), 64.7 (NCHCH$_2$OTBDMS), 60.5 (NCHCH$_2$OTBDMS), 51.3 (NCH$_2$C=CH$_2$), 34.9 (NCH$_2$C=CH$_2$CH$_2$), 25.9 (SiC(CH$_3$)$_3$), 18.3 (SiC(CH$_3$)$_3$), −5.4 (Si(CH$_3$)$_2$); MS (EI), m/z (relative intensity) 227 (M$^+$, 8), 212 (6), 170 (M-$^t$Bu, 36), 96 (8), 82 (M-CH$_2$OTBDMS, 100), 75 (11); IR (Neat) 3550-3100 (br, NH), 3074 (C=CH$_2$), 2929, 2857, 1664 (C=C), 1472, 1424, 1391, 1380, 1361, 1255, 1190, 1101, 1006, 939, 880, 838, 777, 723, 668 cm$^{-1}$.

(2S)-N-[5-Iodo-2-(2,2,2-trichloroethyloxycarbonylamino)-benzoyl]-2-(tert-butyldimethylsilyloxymethyl)-4-methylidenepyrrolidine (10)

A catalytic amount of DMF (3 drops) was added to a stirred solution of Troc protected anthranilic acid 9 (0.46 g, 1.04 mmol) and oxalyl chloride (0.10 mL, 0.15 g, 1.15 mmol) in CH$_2$Cl$_2$ (30 mL). After 16 hours at room temperature the resulting acid chloride solution was added dropwise over 30 minutes to a stirred mixture of the amine 8 (0.26 g, 1.15 mmol) and TEA (0.26 g, 0.36 mL, 2.58 mmol) in CH$_2$Cl$_2$ (15 mL) at −20° C. (CCl$_4$/liq.N$_2$) under a nitrogen atmosphere. The reaction mixture was allowed to warm to room temperature and stirred for a further 45 minutes. At this point TLC analysis (50% EtOAc/Petroleum Ether) revealed complete reaction. The mixture was washed with saturated NaHCO$_3$ (30 mL), saturated NH$_4$Cl (30 mL), H$_2$O (25 mL), brine (30 mL), dried (MgSO$_4$), filtered and evaporated in vacuo to give the amide 10 as a dark oil (0.65 g, 96%): $^1$H NMR (270 MHz, CDCl$_3$) (Rotamers) δ 8.92 (br s, 1H), 8.05-7.88 (m, 1H), 7.74-7.64 (m, 1H), 7.56-7.46 (m, 1H), 5.08-4.95 (m, 2H), 4.84 (d, 1H, J=11.91 Hz), 4.75 (d, 1H, J=11.91 Hz), 4.74-4.65 (m, 1H), 4.21-3.68 (m, 4H), 2.96-2.65 (m, 2H), 0.95-0.87 (m, 9H), 0.1-0.03 (m, 6H).

(2S)-N-(2-Amino-5-iodobenzoyl)-2-(hydroxymethyl)-4-methylidenepyrrolidine (11)

A solution of TBAF (1.24 mL of a 1 M solution in THF, 1.24 mmol) was added to the silyl-ether 10 (0.64 g, 0.99 mmol) in THF (15 mL) at 0° C. (ice/acetone). The reaction mixture was allowed to warm to room temperature and after 45 minutes TLC (50% EtOAc/Pet-Ether 40°-60°) revealed the complete disappearance of starting material. Saturated NH$_4$Cl (75 mL) was added and the reaction mixture extracted with EtOAc (3×30 mL), washed with brine (30 mL), dried (MgSO$_4$), filtered and evaporated in vacuo to give an orange oil. Purification by flash chromatography (50% EtOAc/Pet-Ether 40°-60°) provided the pure aminoalcohol 61 as a viscous oil (0.18 g, 51%): $^1$H NMR (270 MHz, CDCl$_3$) δ 7.72-7.61 (m, 1H), 7.55-7.40 (m, 1H), 6.51-6.49 (m, 1H), 5.02-4.94 (m, 2H), 4.80-3.80 (m, 8H), 2.81-2.79 (m, 1H), 2.43-2.40 (m, 1H); MS (EI), m/z (relative intensity) 359 (M$^+$+1, 5), 358 (M$^+$, 33), 328 (3), 327 (10), 254 (3), 247 (11), 246 (100), 218 (18), 164 (2), 127 (4), 120 (4), 119 (10), 113 (9), 112 (91), 94 (2), 91 (20), 90 (5), 82 (10), 67 (2), 64 (3), 63 (3), 52 (3).

(2S)-N-[5-Iodo-2-(2,2,2-trichloroethyloxycarbonylamino)-benzoyl]-2-(hydroxymethyl)-4-methylidenepyrrolidine (12)

A solution of the amine 11 (179 mg, 0.50 mmol) in CH$_2$Cl$_2$ (15 mL) was cooled to 0° C. (ice/acetone) and treated with pyridine (81 μL, 79 mg, 1.0 mmol). A solution of 2,2,2-trichloroethylchloroformate (76 μL, 117 mg, 0.55 mmol) in CH$_2$Cl$_2$ (5 mL) was then added dropwise to the stirred mixture. The reaction mixture was allowed to warm to room temperature and stirred for a further 2 h, at which point TLC (EtOAc) revealed complete consumption of amine 11. The reaction mixture was washed with saturated CuSO$_4$ (25 mL), H$_2$O (25 mL), brine (25 mL), dried (MgSO$_4$), filtered and evaporated in vacuo. The crude residue was purified by flash chromatography (50% EtOAc/Petroleum Ether) to afford the pure troc-amino compound 12 as an oil (189 mg, 71%): $^1$H NMR (270 MHz, CDCl$_3$) δ 8.90 (brs, 1H), 7.75-7.66 (m, 3H), 5.02-4.92 (m, 3H), 4.87 (d, 1H, J=12.09 Hz), 4.72 (d, 1H, J=12.09 Hz), 4.15-4.08 (m, 2H), 3.90-3.85 (m, 2H), 3.65-3.63 (m, 1H), 2.80-2.71 (m, 1H), 2.50 (d, 1H, J=14.83 Hz); $^{13}$C NMR (67.8 MHz, CDCl$_3$) δ 167.7, 151.9, 142.7, 139.6, 135.6, 134.8, 127.7, 123.4, 108.4, 95.1, 86.6, 74.3, 63.9, 59.0, 53.5, 33.7; MS (EI), m/z (relative intensity) 536 (5), 535 (3), 534 (15), 533 (M$^+$, 3), 532 (15), 503 (2), 501 (2), 422 (4), 420 (5), 385 (8), 384 (8), 366 (3), 353 (11), 290 (9), 273 (8), 272 (76), 246 (6), 245 (18), 218 (4), 217 (5), 216 (8), 146 (4), 145 (10), 133 (4), 131 (4), 119 (6), 117 (7), 115 (11), 113 (17), 112 (39), 97 (4), 96 (3), 95 (12), 90 (5), 84 (5), 83 (7), 82 (100), 79 (7), 77 (21), 67 (2), 63 (4), 61 (3), 51 (6); exact mass calcd for C$_{16}$H$_{16}$N$_2$O$_4$Cl$_3$I m/z 531.9221, obsd m/z 531.9155.

(11S,11aS)-11-Hydroxy-7-iodo-2-methylidene-10-(2,2,2-trichloroethyloxycarbonylamino)-1,2,3,10,11,11a-hexahydro-5H-pyrrolo[2,1-c][1,4]benzodiazepin-5-one (13)

A solution of the alcohol 12 (189 mg, 0.35 mmol) in CH$_2$Cl$_2$/CH$_3$CN (12 mL, 3:1) was treated with 4 Å powdered molecular sieves (100 mg) and NMO (62 mg, 0.53 mmol). After 15 minutes stirring at room temperature, TPAP (6.2 mg, 17.7 μmol) was added and stirring continued for a further 1 hour at which point TLC (50% EtOAc/Petroleum Ether) showed product formation along with some unoxidised starting material. The mixture was then treated with a further quantity of NMO (62 mg, 0.53 mmol) and TPAP (6.2 mg, 17.7 μmol) and allowed to stir for a further 30 minutes after which time TLC revealed complete reaction. The mixture was evaporated in vacuo onto silica and subjected to flash chromatography (40% EtOAc/Petroleum Ether) to provide the protected carbinolamine 13 as a white glass (93 mg, 49%): $^1$H NMR (270 MHz, CDCl$_3$) δ 8.09 (d, 1H, J=2.01 Hz), 7.80 (dd, 1H, J=8.43, 2.20 Hz), 7.10 (d, 1H, J=8.43 Hz), 5.60 (d, 1H, J=9.71Hz), 5.20-5.04 (m, 3H), 4.79-4.50 (m, 1H), 4.32-4.08 (m, 3H), 3.63 (t, 1H, J=8.79Hz), 2.99-2.89 (m, 1H), 2.72 (d, 1H, J=15.94 Hz); $^{13}$C NMR (67.8 MHz, CDCl$_3$) δ 165.0, 154.1, 141.0, 140.2, 137.7, 134.5, 133.6, 132.0, 110.4, 94.7, 93.4, 85.7, 75.0, 59.4, 50.7, 35.0; MS (EI), m/z (relative intensity) 533 (6), 532 (22), 531 (M$^+$, 8), 530 (17), 529 (10), 449 (5), 383 (6), 354 (7), 353 (5), 338 (6), 325 (5), 290 (5), 274 (15), 273 (8), 272 (43), 254 (5), 245 (8), 218 (5), 216 (12), 147 (5), 146 (6), 145 (9), 133 (10), 131 (9), 128 (5), 127 (15), 119 (11), 117 (5), 97 (6), 95 (9), 92 (6), 91 (6), 90 (6), 83 (11), 82 (100), 81 (7), 80 (8), 75 (5), 63 (7), 53 (5); exact mass calcd for C$_{16}$H$_{14}$N$_2$O$_4$ICl$_3$ m/e 531.9037, obsd m/e 531.8988.

(11aS)-7-Iodo-2-methylidene-1,2,3,11a-tetrahydro-5H-pyrrolo[2,1-c][1,4]benzodiazepin-5-one (14, UP2023, BSD-SJG)

10% cadmium-lead couple (109 mg, 0.875 mmol) was added to a stirred solution of the Troc-protected carbinolamine 13 (93 mg, 0.175 mmol) in THF (1 mL) and aqueous 1 N ammonium acetate (1 mL). After 45 minutes at room temperature TLC revealed complete reaction (70% EtOAc/Petroleum Ether). The mixture was diluted with EtOAc (30 mL), dried (MgSO$_4$), filtered and evaporated in vacuo. The crude residue was purified by flash chromatography (70% EtOAc/Petroleum Ether) to provide the novel PBD (14, BSD-SJG, UP2023) as a white solid (27 mg, 46%): mp ° C.; $^1$H NMR (270 MHz, CDCl$_3$+CD$_3$OD) (11S,11aS isomer) δ 8.10 (d, 1H, J=1.46Hz), 7.65 (d, 1H, J=8.79 Hz), 6.86 (d, 1H, J=8.06 Hz), 5.14-5.10 (m, 2H), 4.66 (d, 1H, J=5.13 Hz), 4.34 (d, 1H, J=16.12 Hz), 4.23 (d, 1H, J=16.12 Hz), 3.80-3.71 (m, 1H), 3.34 (s, 3H), 3.03-2.86 (m, 1H), 2.65 (d, 1H, J=16.02 Hz); MS (EI), m/z (relative intensity) (N10-C11 imine form) 339 (M$^+$+1, 20), 338 (M$^+$, 100), 337 (17), 323 (5), 311 (4), 310 (5), 257 (5), 230 (4), 229 (13), 211 (4), 203 (4), 202 (8), 184 (8), 183 (4), 103 (5), 82 (17), 81 (4), 80 (5), 76 (6), 75 (16), 74 (5), 55 (4), 53 (4); IR (NUJOL$^7$) 3295 (br), 2923, 2853, 1716, 1615, 1506, 1457, 1377, 1317, 1278, 1238, 1169, 1118, 1063, 999, 895, 818, 751, 718 cm$^{-1}$; exact mass calcd for C$_{13}$H$_{11}$N$_2$OI m/e 337.9916, obsd m/e 337.9870.

Figure 2:
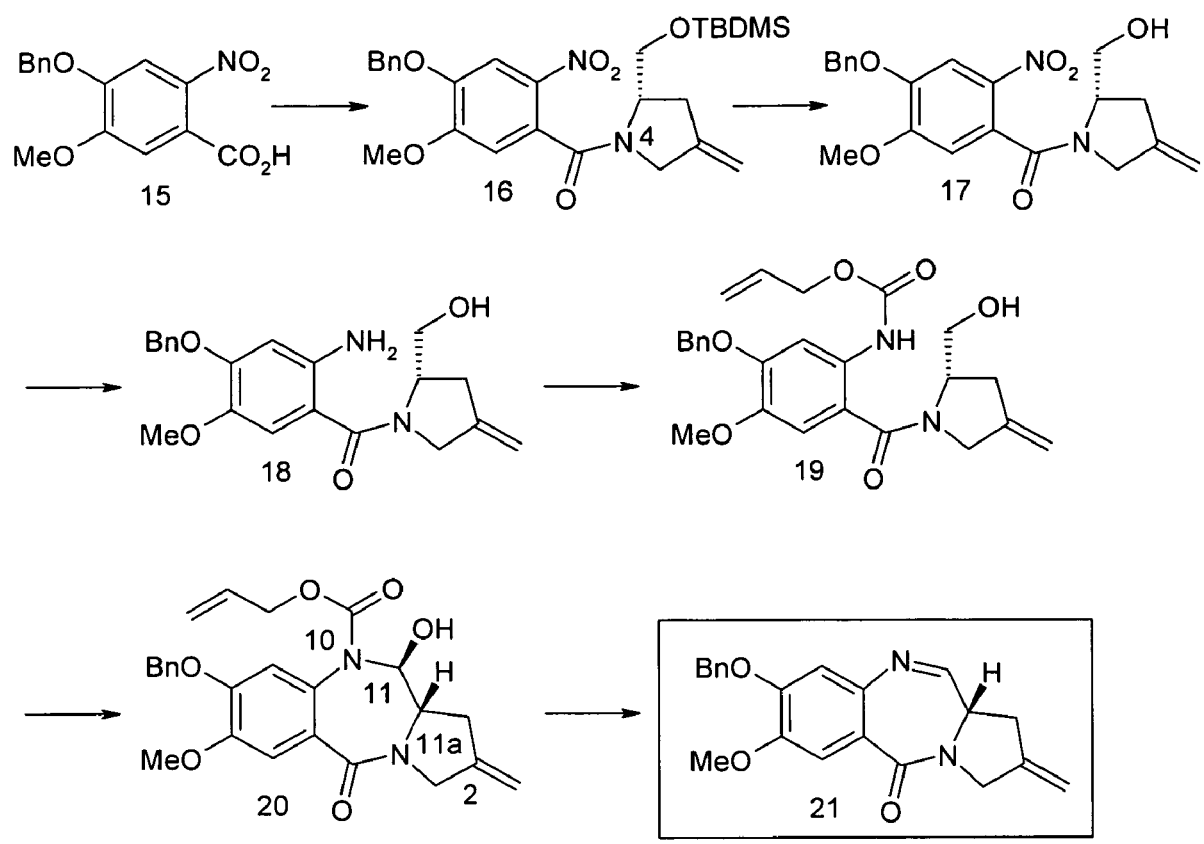

Example 1(b)
Synthesis of the
C8-Benzyl-C7-Methoxy-C2-methlene PBD
Monomer SJG-244 (21) (see FIG. 2)

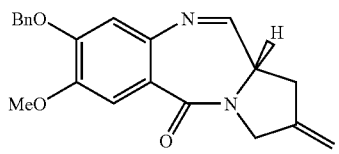

(2S)-N-(4-Benzyloxy-5-methoxy-2-nitrobenzoyl)-2-(tert-butyldimethylsilyloxymethyl)-4-methylidenepyrrolidine (16)

A catalytic amount of DMF (2 drops) was added to a stirred solution of nitro-acid 15 (0.645 g, 2.13 mmol) and oxalyl chloride (0.23 mL, 0.33 g, 2.60 mmol) in CH$_2$Cl$_2$ (40 mL). After 16 hours at room temperature the resulting acid chloride solution was added dropwise to a stirred mixture of the amine 8 (0.522 g, 2.30 mmol) and TEA (0.58 g, 0.80 mL, 5.73 mmol) in CH$_2$Cl$_2$ (5 mL) at 0° C. (ice/acetone) under a nitrogen atmosphere. The reaction mixture was allowed to warm to room temperature and stirred for a further 2.5 h. The mixture was diluted with CH$_2$Cl$_2$ (50 mL), washed with saturated NaHCO$_3$ (50 mL), saturated NH$_4$Cl (50 mL), H$_2$O (50 mL), brine (50 mL), dried (MgSO$_4$), filtered and evaporated in vacuo to give the crude product as a dark orange oil. Purification by flash chromatography (20% EtOAc/Petroleum Ether) isolated the pure amide 16 as a sticky orange oil (0.86 g, 79%): [α]$^{22}_D$=−47.2° (c=2.79, CHCl$_3$); $^1$H NMR (270 MHz, CDCl$_3$) (Rotamers) δ 7.78 and 7.77 (s×2, 1H$_{arom}$), 7.48-7.35 (m, 5H$_{arom}$), 6.82 and 6.78 (s×2, 1H$_{arom}$), 5.23 and 5.21 (s×2, 2H, PhCH$_2$O), 5.09-4.83 (m, 2H, NCH$_2$C=CH$_2$), 4.59-4.49 (m, 1H, NCHCH$_2$OTBDMS), 4.03-3.08 (m, 7H, NCHCH$_2$OTBDMS, NCH$_2$C=CH$_2$ and OCH$_3$), 2.80-2.56 (m, 2H, NCH$_2$C=CH$_2$CH$_2$), 0.89 and 0.79 (s×2, 9H, SiC (CH$_3$)$_3$), 0.122, −0.11 and −0.14 (s×3, 6H, Si(CH$_3$)$_2$); $^{13}$C NMR (67.8 MHz, CDCl$_3$) (Rotamers) δ 166.2 (NC=O), 154.8 and 154.6 (C$_{quat}$), 148.2 and 148.0 (C$_{quat}$), 144.1 and 143.2 (C$_{quat}$), 137.1 (C$_{quat}$), 135.3 (C$_{quat}$), 128.8 and 128.5 (BnC—H$_{arom}$), 128.2 (C$_{quat}$), 127.6 (BnC—H$_{arom}$), 110.1 and 109.2 (C—H$_{arom}$), 109.0 and 108.5 (C—H$_{arom}$), 107.5 (NCH$_2$C=CH$_2$), 71.3 (PhCH$_2$O), 63.7 (NCHCH$_2$OTBDMS), 60.2 (NCHCH$_2$OTBDMS), 58.1 and 56.6 (OCH$_3$), 52.8 and 50.5 (NCH$_2$C=CH$_2$), 34.9 and 33.9 (NCH$_2$C=CH$_2$CH$_2$), 25.8 and 25.7 (SiC(CH$_3$)$_3$), 18.2 (SiC (CH$_3$)$_3$), −5.4 and −5.6 (Si(CH$_3$)$_2$); MS (EI), m/z (relative intensity) 512 (M$^+$, 3), 497 (M-CH$_3$, 4), 455 (M-$^t$Bu, 100), 380 (2), 364 (5), 286 (M-NCH$_2$C=CH$_2$CH$_2$CHCH$_2$OTBDMS, 40), 279 (9), 226 (NCH$_2$C=CH$_2$CH$_2$CHCH$_2$OTBDMS, 5), 168 (10), 149 (27), 91 (PhCH$_2$, 62), 73 (8), 57 (9); IR (NEAT) 3066, 3034, 2953, 2856, 2245, 1644 (NC=O), 1578, 1520, 1454, 1426, 1379, 1335, 1276, 1220, 1186, 1106, 1059, 1016, 910, 836, 815, 779, 734, 697, 655, 614 cm$^{-1}$.

(2S)-N-(4-Benzyloxy-5-methoxy-2-nitrobenzoyl)-2-(hydroxymethyl)-4-methylidenepyrrolidine (17)

A solution of TBAF (2.10 mL of a 1M solution in THF, 2.10 mmol) was added to the silyl-ether 16 (0.86 g, 1.68 mmol) in THF (20 mL) at 0° C. (ice/acetone). The reaction mixture was allowed to warm to room temperature following a colour change (yellow→dark red). After a further 40 minutes TLC (50% EtOAc/Pet-Ether 40°-60°) revealed the complete disappearance of starting material. Saturated NH$_4$Cl (100 mL) was added and the reaction mixture extracted with EtOAc (3×40 mL), washed with brine (30 mL), dried (MgSO$_4$), filtered and evaporated in vacuo to give a dark orange oil which was purified by flash chromatography (60% EtOAc/Petroleum Ether) to provide the pure alcohol 17 as a white solid (0.64 g, 96%): [α]$^{19}_D$=−22.9° (c=0.20, MeOH); $^1$H NMR (270 MHz, CDCl$_3$) (Rotamers) δ 7.78 and 7.76 (s×2, 1H$_{arom}$), 7.49-7.33 (m, 5H$_{arom}$), 6.91 and 6.82 (s×2, 1H$_{arom}$), 5.22 (s, 2H, PhCH$_2$O), 5.10 (m,1H, OH), 5.03-5.01 (m, 1H, NCH$_2$C=CH$_2$), 4.90-4.85 (m,1H, NCH$_2$C=CH$_2$), 4.65-4.55 (m, 1H, NCHCH$_2$OH), 3.99 and 3.95 (s×2, 3H, OCH$_3$), 3.90-3.72 (m, 4H, NCHCH$_2$OH and NCH$_2$C=CH$_2$), 2.90-2.87 (m,1H, NCH$_2$C=CH$_2$CH$_2$), 2.53-2.47 (m, 1H, NCH$_2$C=CH$_2$CH$_2$); $^{13}$C NMR (67.8 MHz, CDCl$_3$) (Rotamers) δ 177.4 (NC=O), 155.1 (C$_{quat}$), 148.3 (C$_{quat}$), 142.6 (C$_{quat}$), 137.0 (C$_{quat}$), 135.2 (C$_{quat}$), 128.9,128.6 and 127.6 (BnC—H$_{arom}$), 109.1 (C—H$_{arom}$), 108.5 (C—H$_{arom}$), 108.3 (NCH$_2$C=CH$_2$), 71.4 (PhCH$_2$O), 65.2 and 63.7 (NCHCH$_2$OH), 60.4 (NCHCH$_2$OH), 56.8 and 56.7 (OCH$_3$), 53.0 and 50.1 (NCH$_2$C=CH$_2$), 35.1 and 34.4 (NCH$_2$C=CH$_2$CH$_2$); MS (EI), m/z (relative intensity) 398 (M$^+$, 2), 380 (3), 368 (4), 354 (1), 286 (M-NCH$_2$C=CH$_2$CH$_2$CHCH$_2$OH, 54), 270 (2), 256 (1), 164 (2), 136 (4), 135 (3), 121 (4), 112 (NCH$_2$C=CH$_2$CH$_2$CHCH$_2$OH, 3), 91 (PhCH$_2$, 100), 82 (3), 69 (4), 65 (6); IR (NUJOL$^7$) 3600-3200 (br, OH), 2923, 2853, 1718, 1663, 1611 (NC=O), 1577, 1517, 1460, 1376, 1332, 1275, 1224, 1176, 1052, 990, 925, 886, 862, 796, 759, 723, 702 615 cm$^{-1}$; exact mass calcd for C$_{21}$H$_{22}$N$_2$O$_6$ m/e 398.1478, obsd m/e 398.1490.

(2S)-N-(2-Amino-4-benzyloxy-5-methoxybenzoyl)-2-(hydroxymethyl)-4-methylidenepyrrolidine (18)

The nitro-alcohol 17 (0.637 g, 1.60 mmol), SnCl$_2$ 2H$_2$O (1.81 g, 8.0 mmol) and methanol (36 mL) were heated at reflux and monitored by TLC (90% CHCl$_3$/MeOH). After 1 hour the MeOH was evaporated in vacuo and the resulting residue cooled (ice), and treated carefully with saturated NaHCO$_3$ (120 mL). The mixture was diluted with EtOAc (120 mL), and after 16 hours stirring at room temperature the inorganic precipitate was removed by filtration through celite. The organic layer was separated, washed with brine (100 mL), dried (MgSO$_4$), filtered and evaporated in vacuo to give an orange glass. Flash chromatography (EtOAc) afforded the pure amine 18 as a pale yellow glass (0.37 g, 63%): [α]$^{23}_D$=−42.7° (c=3.7, CHCl$_3$); $^1$H NMR (270 MHz, CDCl$_3$) δ 7.44-7.29 (m, 5H$_{arom}$), 6.77 (s, 1H$_{arom}$), 6.27 (s, 1H$_{arom}$), 5.12 (s, 2H, PhCH$_2$O), 5.06-5.00 (m, 1H, NCH$_2$C=CH$_2$), 4.99-4.92 (m, 1H, NCH$_2$C=CH$_2$), 4.63-4.53 (m, 1H, NCHCH$_2$OH), 4.25-3.60 (m, 10H, NCHCH$_2$OH, NCH$_2$C=CH$_2$, OCH$_3$, OH and NH$_2$), 2.77 (dd, 1H, J=8.52, 15.85 Hz, NCH$_2$C=CH$_2$CH$_2$), 2.43-2.39 (m, 1H, NCH$_2$C=CH$_2$CH$_2$); $^{13}$C NMR (67.8 MHz, CDCl$_3$) δ 171.4 (NC=O), 151.0 (C$_{quat}$), 143.3 (C$_{quat}$), 141.5 (C$_{quat}$), 140.6 (C$_{quat}$), 136.5 (C$_{quat}$), 128.6 and 128.0 (BnC—H$_{arom}$), 127.8 (C$_{quat}$), 127.1 (BnC—H$_{arom}$), 112.5 (C—H$_{arom}$), 107.8 (NCH$_2$C=CH$_2$), 103.0 (C—H$_{arom}$), 70.6 (PhCH$_2$O), 65.9 (NCHCH$_2$OH), 60.0 (NCHCH$_2$OH), 57.1 (OCH$_3$), 53.3 (NCH$_2$C=CH$_2$), 34.4 (NCH$_2$C=CH$_2$CH$_2$); MS (EI), m/z (relative intensity) 368 (M$^+$, 100), 353 (M-CH$_3$, 2), 340 (1), 286 (2), 273 (4), 256 (M-NCH$_2$C=CH$_2$CH$_2$CHCH$_2$OH, 59 ), 249 (8), 226 (4), 200 (2), 196 (2), 166 (5), 138 (17), 112 (NCH$_2$C=CH$_2$CH$_2$CHCH$_2$OH, 39), 91 (PhCH$_2$, 70), 82 (5), 65 (5); IR (NEAT) 3600-3000 (br, NH$_2$ and OH), 3065, 3052, 2932, 2869, 2246, 1668, 1620, 1592, 1513, 1454, 1408, 1264, 1229, 1197, 1176, 1113, 1079, 1002, 909, 733, 698, 645 cm$^{-1}$; exact mass calcd for C$_{21}$H$_{24}$N$_2$O$_4$ m/e 368.1736, obsd m/e 368.1662.

(2S)-N-[(2-Allyloxycarbonylamino)-4-benzyloxy-5-methoxybenzoyl]-2-(hydroxymethyl)-4-methylidenepyrrolidine (19)

A solution of the amino-alcohol 18 (0.33 g, 0.90 mmol) in CH$_2$Cl$_2$ (20 mL) was cooled to 0° C. (ice/acetone) and treated with pyridine (0.14 mL, 0.14 g, 1.77 mmol). A solution of allyl chloroformate (87 μL, 99 mg, 0.82 mmol) in CH$_2$Cl$_2$ (7 mL) was then added dropwise to the stirred mixture. The reaction mixture was allowed to warm to room temperature and stirred for a further 2.5 h, at which point TLC (EtOAc) revealed complete consumption of amine 18. The reaction mixture was diluted with CH$_2$Cl$_2$ (30 mL) and washed with saturated CuSO$_4$ (40 mL), H$_2$O (40 mL), brine (40 mL), dried (MgSO$_4$), filtered and evaporated in vacuo. The crude residue was purified by flash chromatography (80% EtOAc/Petroleum Ether) to afford the pure allocamino compound 19 as a white solid (0.34 g, 84%): [α]$^{22}_D$=−22.4° (c=3.4, CHCl$_3$); $^1$H NMR (270 MHz, CDCl$_3$) δ 8.52 (br s, 1H, NH), 7.82 (br s, 1H$_{arom}$), 7.49-7.29 (m, 5H$_{arom}$), 6.84 (s, 1H$_{arom}$), 6.02-5.88 (m, 1H, NCO$_2$CH$_2$CH=CH$_2$), 5.39-5.22 (m, 2H, NCO$_2$CH$_2$CH=CH$_2$), 5.17 (s, 2H, PhCH$_2$O), 5.01 (brs, 1H, NCH$_2$C=CH$_2$), 4.94 (br s, 1H, NCH$_2$C=CH$_2$), 4.64-4.59 (m, 3H, NCHCH$_2$OH and NCO$_2$CH$_2$CH=CH$_2$), 4.21-3.60 (m, 8H, NCHCH$_2$OH, NCH$_2$C=CH$_2$, OCH$_3$ and OH), 2.77 (dd, 1H, J=8.61, 15.94 Hz, NCH$_2$C=CH$_2$CH$_2$), 2.46 (d, 1H, J=15.94 Hz, NCH$_2$C=CH$_2$CH$_2$); $^{13}$C NMR (67.8 MHz, CDCl$_3$) δ 171.4 (NC=O$_{amide}$), 153.7 (NC=O$_{carbamate}$), 150.3 (C$_{quat}$), 144.5 (C$_{quat}$), 143.0 (C$_{quat}$), 136.2 (C$_{quat}$), 132.4 (NCO$_2$CH$_2$CH=CH$_2$), 131.3 (C$_{quat}$), 128.6, 128.1, and 127.7 (BnC—H$_{arom}$), 118.1 (NCO$_2$CH$_2$CH=CH$_2$), 111.1 (C—H$_{arom}$), 108.1 (NCH$_2$C=CH$_2$), 106.5 (C—H$_{arom}$), 70.7 (PhCH$_2$O), 65.8 (NCO$_2$CH$_2$CH=CH$_2$), 65.5 (NCHCH$_2$OH), 59.9 (NCHCH$_2$OH), 56.7 (OCH$_3$), 54.0 (NCH$_2$C=CH$_2$), 34.1 (NCH$_2$C=CH$_2$CH$_2$); MS (EI), m/z (relative intensity) 452 (M$^+$, 38), 395 (M-OC$_3$H$_5$, 4), 394 (10), 340 (M-NCH$_2$C=CH$_2$CH$_2$CHCH$_2$OH, 20), 298 (7), 282 (22), 255 (8), 206 (2), 192 (2), 163 (3), 136 (3), 114 (6), 112 (NCH$_2$C=CH$_2$CH$_2$CHCH$_2$OH, 12), 91 (PhCH$_2$, 100), 82 (10), 65 (4), 57 (OC$_3$H$_5$, 7); IR (NUJOL$^7$) 3600-2000 (br, OH), 3335, 3242, 2922, 2854, 1724, 1614, 1537, 1463, 1407, 1378, 1349, 1280, 1214, 1178, 1117, 1054, 1028, 995, 947, 908, 892, 853, 821, 768, 735, 697, 629, 601, 514 cm$^{-1}$; exact mass calcd for C$_{25}$H$_{28}$N$_2$O$_6$ m/e 452.1947, obsd m/e 452.1923.

(11S,11aS)-10-Allyloxycarbonyl-8-benzyloxy-11-hydroxy-7-methoxy-2-methylidene-1,2,3,10,11,11a-hexahydro-5H-pyrrolo[2,1-c][1,4]benzodiazepin-5-one (20)

A solution of DMSO (0.18 mL, 0.20 g, 2.56 mmol) in CH$_2$Cl$_2$ (4 mL) was added dropwise over 30 minutes to a solution of oxalyl chloride (0.63 mL of a 2.0 M solution in CH$_2$Cl$_2$, 1.26 mmol) at −45° C. (dry ice/CH$_3$CN) under a nitrogen atmosphere. After stirring at −45° C. for 30 minutes, a solution of the alcohol 19 (0.42 g, 0.93 mmol) dissolved in CH$_2$Cl$_2$ (8 mL) was added dropwise over 35 minutes at −45° C. After 45 minutes at −45° C., the mixture was treated dropwise with TEA (0.50 mL, 0.36 g, 3.56 mmol) in CH$_2$Cl$_2$ (4 mL) over 30 minutes at −45° C. After 35 minutes, the reaction mixture was allowed to warm to room temperature and was diluted with CH$_2$Cl$_2$ (30 mL), washed with 1 N HCl (20 mL), H$_2$O (20 mL), brine (30 mL), dried (MgSO$_4$), filtered and evaporated in vacuo. TLC (80% EtOAc/Petroleum Ether) of the crude material revealed sufficient product formation and a trace of unoxidised starting material. Purification by flash chromatography (50% EtOAc/Petroleum Ether) furnished the protected carbinolamine 20 as white glass (0.172 g, 41%): $^1$H NMR (270 MHz, CDCl$_3$) δ 7.48-7.27 (m, 5H$_{arom}$), 7.25 (s, 1H$_{arom}$), 6.74 (br s, 1H$_{arom}$), 5.65-5.53 (m, 1H, NCO$_2$CH$_2$CH=CH$_2$), 5.56 (d, 1H, J=9.89Hz, NCHCHOH), 5.22-5.04 (m, 6H, NCH$_2$C=CH$_2$, NCO$_2$CH$_2$CH=CH$_2$ and PhCH$_2$O), 4.64-4.42 (m, 3H, NCO$_2$CH$_2$CH=CH$_2$ and OH), 4.28 (d, 1H, J=15.94Hz, NCH$_2$C=CH$_2$), 4.09 (d, 1H, J=15.94 Hz, NCH$_2$C=CH$_2$), 3.92 (s, 3H, OCH$_3$), 3.62 (t, 1H, J=8.79Hz, NCHCHOH), 2.90 (dd, 1H, J=8.97, 16.03 Hz, NCH$_2$C=CH$_2$CH$_2$), 2.67 (d, 1H, J=16.03 Hz, NCH$_2$C=CH$_2$CH$_2$); $^{13}$C NMR (67.8 MHz, CDCl$_3$) δ 166.8 (NC=O$_{amide}$), 156.0 (NC=O$_{carbamate}$), 150.1 (C$_{quat}$), 149.0 (C$_{quat}$), 141.8 (C$_{quat}$), 136.1 (C$_{quat}$), 131.8 (NCO$_2$CH$_2$CH=CH$_2$), 128.6, 128.1 and 127.3 (BnC—H$_{arom}$), 125.6 (C$_{quat}$), 118.0 (NCO$_2$CH$_2$CH=CH$_2$), 114.6 (C—H$_{arom}$), 110.6 (C—H$_{arom}$), 109.8 (NCH$_2$C=CH$_2$), 85.8 (NCHCHOH), 71.0 (PhCH$_2$O), 66.7 (NCO$_2$CH$_2$CH=CH$_2$), 59.8 (NCHCHOH), 56.2 (OCH$_3$), 50.7 (NCH$_2$C=CH$_2$), 35.0 (NCH$_2$C=CH$_2$CH$_2$); MS (EI), m/z (relative intensity) 450 (M$^+$, 24), 422 (1), 392 (1), 364 (1), 348 (3), 340 (12), 298 (6), 282 (8), 257 (2), 229 (2), 192 (3), 178 (2), 164 (4), 136 (3), 110 (3), 91 (PhCH$_2$, 100), 82 (17), 65 (7); IR (NUJOL[7]) 3600-2500 (br, OH) 2923, 2854, 1711, 1619, 1601, 1513, 1463, 1405, 1377, 1300, 1278, 1202, 1119, 1045, 993, 956, 909, 790, 768, 724, 697, 637 cm$^{-1}$; exact mass calcd for C$_{25}$H$_{26}$N$_2$O$_6$m/e 450.1791, obsd m/e 450.1790.

Alternative synthesis (11S,11aS)-10-Allyloxycarbonyl-8-benzyloxy-11-hydroxy-7-methoxy-2-methylidene-1,2,3,10,11,11a-hexahydro-5H-pyrrolo[2,1-c][1,4]benzodiazepin-5-one (20)

A solution of the alcohol 19 (0.32 g, 0.71 mmol) in CH$_2$Cl$_2$/CH$_3$CN (30 mL, 3:1) was treated with 4 A powdered molecular sieves (0.2 g) and NMO (126 mg, 1.08 mmol). After 15 minutes stirring at room temperature, TPAP (12.6 mg, 35.9 µmol) was added and stirring continued for a further 1 hour 20 minutes at which point TLC (80% EtOAc/Petroleum Ether) revealed product formation along with some unoxidised starting material. The mixture was then treated with a further quantity of NMO (126 mg, 1.08 mmol) and TPAP (12.6 mg, 35.9 µmol), and allowed to stir for a further 0.5 hours after which time TLC revealed reaction completion. The mixture was evaporated in vacuo onto silica and subjected to flash chromatography (50% EtOAc/Petroleum Ether) to provide the protected carbinolamine 20 as a white glass (153 mg, 48%): $[\alpha]^{23}_D$=+129.8° (c=1.5, CHCl$_3$); $^1$H NMR (270 MHz, CDCl$_3$) δ 7.48-7.27 (m, 5H$_{arom}$), 7.25 (s, 1H$_{arom}$), 6.74 (br s, 1H$_{arom}$), 5.65-5.53 (m, 1H, NCO$_2$CH$_2$CH=CH$_2$), 5.56 (d, 1H, J=9.89 Hz, NCHCHOH), 5.22-5.04 (m, 6H, NCH$_2$C=CH$_2$, NCO$_2$CH$_2$CH=CH$_2$ and PhCH$_2$O), 4.64-4.42 (m, 3H, NCO$_2$CH$_2$CH=CH$_2$ and OH), 4.28 (d, 1H, J=15.94 Hz, NCH$_2$C=CH$_2$), 4.09 (d, 1H, J=15.94 Hz, NCH$_2$C=CH$_2$), 3.92 (s, 3H, OCH$_3$), 3.62 (t, 1H, J=8.79 Hz, NCHCHOH), 2.90 (dd, 1H, J=8.97, 16.03 Hz, NCH$_2$C=CH$_2$CH$_2$), 2.67 (d, 1H, J=16.03 Hz, NCH$_2$C=CH$_2$CH$_2$); $^{13}$C NMR (67.8 MHz, CDCl$_3$) δ 166.8 (NC=O$_{amide}$), 156.0 (NC=O$_{carbamate}$), 150.1 (C$_{quat}$), 149.0 (C$_{quat}$), 141.8 (C$_{quat}$), 136.1 (C$_{quat}$), 131.8 (NCO$_2$CH$_2$CH=CH$_2$), 128.6, 128.1 and 127.3 (BnC—H$_{arom}$), 125.6 (C$_{quat}$), 118.0 (NCO$_2$CH$_2$CH=CH$_2$), 114.6 (C—H$_{arom}$), 110.6 (C—H$_{arom}$), 109.8 (NCH$_2$C=CH$_2$), 85.8 (NCHCHOH), 71.0 (PhCH$_2$O), 66.7 (NCO$_2$CH$_2$CH=CH$_2$), 59.8 (NCHCHOH), 56.2 (OCH$_3$), 50.7 (NCH$_2$C=CH$_2$), 35.0 (NCH$_2$C=CH$_2$CH$_2$); MS (EI), m/z (relative intensity) 450 (M$^+$, 24), 422 (1), 392 (1), 364 (1), 348 (3), 340 (12), 298 (6), 282 (8), 257 (2), 229 (2), 192 (3), 178 (2), 164 (4), 136 (3), 110 (3), 91 (PhCH$_2$, 100), 82 (17), 65 (7); IR (NUJOL[7]) 3600-2500 (br, OH), 2923, 2854, 1711, 1619, 1601, 1513, 1463, 1405, 1377, 1300, 1278, 1202, 1119, 1045, 993, 956, 909, 790, 768, 724, 697, 637 cm$^{-1}$; exact mass calcd for C$_{25}$H$_{26}$N$_2$O$_6$m/e 450.1791, obsd m/e 450.1790.

(11aS)-8-Benzyloxy-7-methoxy-2-methylidene-1,2,3,11a-tetrahydro-5H-pyrrolo[2,1-c][1,4]benzodiazepin-5-one (21, SJG-244)

A catalytic amount of tetrakis(triphenylphosphine)palladium (12.0 mg, 10.4 µmol) was added to a stirred solution of the Alloc-protected carbinolamine 20 (0.18 g, 0.40 mmol), triphenylphosphine (5.25 mg, 20 µmol) and pyrrolidine (29 mg, 0.41 mmol) in CH$_2$Cl$_2$ (15 mL). After 2 hours stirring at room temperature under a nitrogen atmosphere, TLC (98% CHCl$_3$/MeOH) revealed the complete consumption of starting material. The solvent was evaporated in vacuo and the crude residue was purified by flash chromatography (60% EtOAc/Petroleum Ether) to afford 21 (SJG-244) as a white glass (116 mg, 83%) which was repeatedly evaporated in vacuo with CHCl$_3$ in an attempt to provide the N10-C11 imine form: $[\alpha]^{22}_D$=+754.2° (c=0.54, CHCl$_3$); $^1$H NMR (270 MHz, CDCl$_3$) (mainly imine, plus trace of carbinolamine form) δ 7.70-7.30 (m, 7H, HCαN and 6H$_{arom}$), 6.84 (s, 1H$_{arom}$), 5.25-5.13 (m, 4H, NCH$_2$C=CH$_2$ and PhCH$_2$O), 4.42 (br s, 2H, NCH$_2$C=CH$_2$), 3.95 (s, 3H, OCH$_3$), 3.88-3.66 (m, 1H, NCHHC=N), 3.09 (dd, 1H, J=8.98, 16.12 Hz, NCH$_2$C=CH$_2$CH$_2$), 2.94-2.87 (m, 1H, NCH$_2$C=CH$_2$CH$_2$); $^{13}$C NMR (67.8 MHz, CDCl$_3$) δ 164.7 (NC=O), 162.6 (HC=N), 150.6 (C$_{quat}$), 148.1 (C$_{quat}$), 141.6 (C$_{quat}$), 140.5 (C$_{quat}$), 136.1 (C$_{quat}$), 132.0, 128.7, 128.6, 128.1 and 127.3 (BnC—H$_{arom}$), 120.1 (C$_{quat}$), 111.5 (C—H$_{arom}$), 111.2 (C—H$_{arom}$), 109.4 (NCH$_2$C=CH$_2$), 70.8 (PhCH$_2$O), 56.2 (OCH$_3$), 53.7 (NCHHC=N), 51.3 (NCH$_2$C=CH$_2$), 35.4 (NCH$_2$C=CH$_2$CH$_2$); MS (EI), m/z (relative intensity) (imine form) 348 (M$^+$, 100), 333 (M-CH$_3$, 42), 319 (3), 269 (5), 257 (M-PhCH$_2$, 25), 241 (11), 229 (56), 227 (11), 213 (5), 186 (4), 156 (6), 136 (22), 122 (4), 91 (PhCH$_2$, 85), 82 (5), 65 (22); IR (NUJOL[7]) 3318 (br, OH of carbinolamine form), 2923, 2853, 1722, 1668, 1600, 1557, 1504, 1462, 1377, 1261, 1216, 1120, 1003, 892, 789, 722, 695, 623, 542 cm$^{-1}$; exact mass calcd for C$_{21}$H$_{20}$N$_2$O$_3$m/e 348.1474, obsd m/e 348.1469.

Example 1(c)

Figure 3:
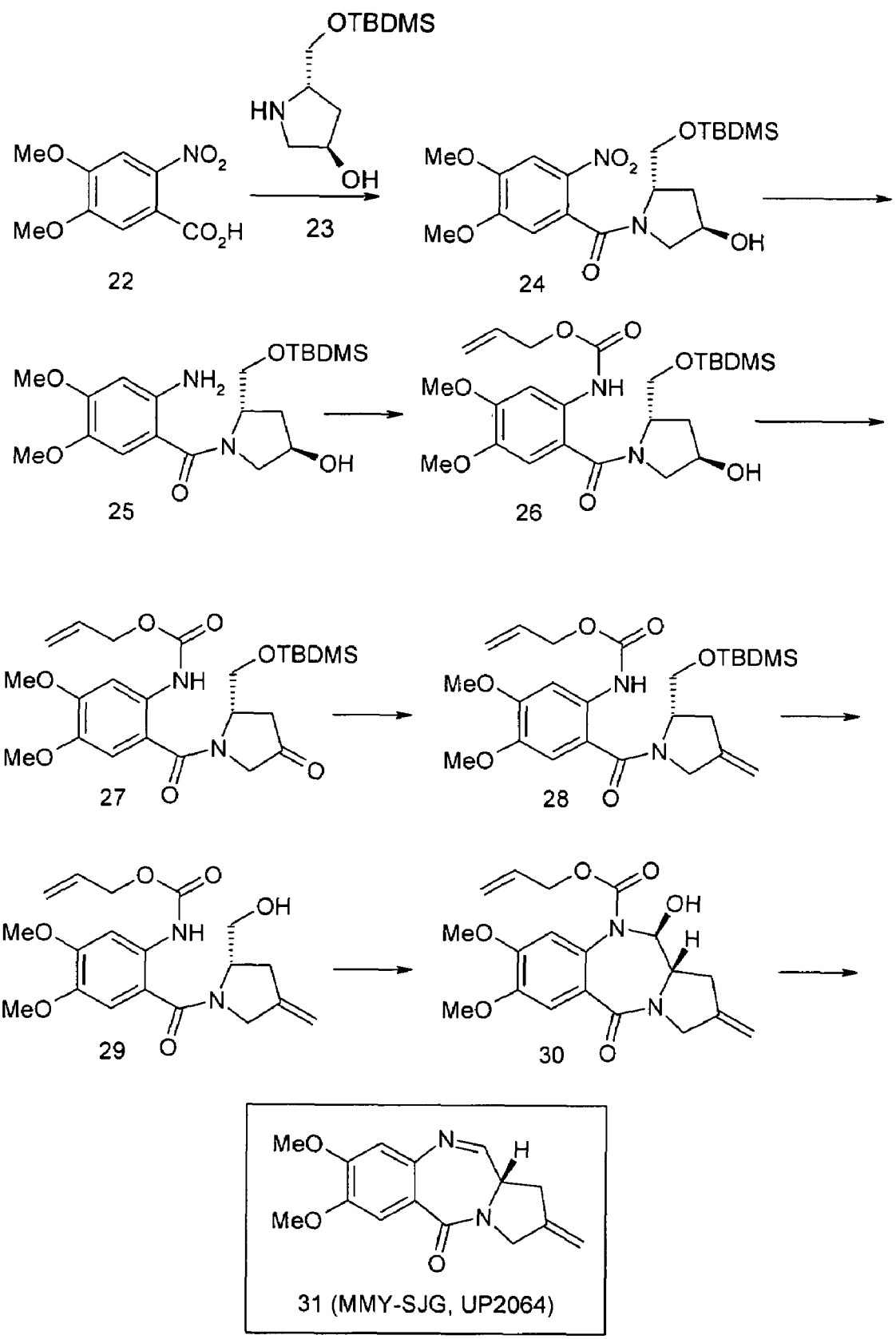

Synthesis of MMY-SJG (31, UP2064)(see FIG. 3)

(2S)(4R)-N-(4,5-Dimethoxy-2-nitrobenzoyl)-2-(tert-butyidimethylsilyloxymethyl)-4-hydroxypyrrolidine (24)

A catalytic amount of DMF (2 drops) was added to a stirred solution of nitro-acid 22 (12.45 g, 54.8 mmol) and oxalyl chloride (5.75 mL, 8.37 g, 65.9 mmol) in CH$_2$Cl$_2$ (300 mL). After 16 hours at room temperature the resulting acid chloride solution was added dropwise over 4.5 hours to a stirred mixture of the amine 23 (12.65 g, 54.8 mmol) and TEA (13.86 g, 19.1 mL, 137 mmol) in CH$_2$Cl$_2$ (300 mL) at 0° C. (ice/acetone) under a nitrogen atmosphere. The reaction mixture was allowed to warm to room temperature and stirred for a further 2.5 h. The mixture was washed with saturated NaHCO$_3$ (300 mL), saturated NH$_4$Cl (300 mL), H$_2$O (250 mL), brine (300 mL), dried (MgSO$_4$), filtered and evaporated in vacuo to give the crude product as a dark orange oil. Purification by flash chromatography (80% EtOAc/Petroleum Ether) isolated the pure amide 24 as a sticky orange oil (18.11 g, 75%): $[\alpha]^{22}_D$=−105.7° (c=1.17, CHCl$_3$); $^1$H NMR (270 MHz, CDCl$_3$) (Rotamers) δ 7.71 and 7.68 (s×2, 1H), 6.86 and 6.79 (s×2, 1H), 4.50 and 4.38 (br s×2, 2H), 4.13-4.10 (m, 1H), 3.98 (s, 3H), 3.94 (s, 3H), 3.78-3.74 (m, 1H), 3.35-3.27 (m, 1H), 3.07 (d, 1H, J=11.17 Hz), 3.01-2.79 (br s, 1H), 2.35-2.26 (m, 1H), 2.11-2.04 (m, 1H), 0.91 and 0.81 (s×2, 9H), 0.10, 0.09, −0.07, and −0.10 (s×4, 6H); $^{13}$C NMR (67.8 MHz, CDCl$_3$) (Rotamers) δ 166.6, 154.2 and 154.1, 149.3 and 148.9, 137.5, 128.0, 109.2, 107.1, 70.1 and 69.4, 64.7 and 62.5, 59.0 and 54.9, 57.3, 56.6, 56.5, 37.4 and 36.3, 25.9 and 25.7, 18.2, −5.4, −5.5 and −5.7; MS (EI), m/z (relative intensity) 440 (M$^+$, 2), 426 (9), 386 (4), 385 (20), 384 (65), 383 (100), 367 (4), 320 (4), 308 (7), 295 (8), 286 (5), 211 (15), 210 (100), 194 (12), 180 (4), 165 (17), 164 (8), 137 (4), 136 (25), 121 (4), 93 (6), 91 (9), 82 (6), 75 (15), 73 (15), 59 (4), 57 (4); IR (NEAT) 3391 (br, OH), 3012 2952, 2931, 2857, 1616, 1578, 1522, 1456, 1436, 1388, 1338, 1279, 1225, 1183, 1151, 1074, 1053, 1029, 1004, 939, 870, 836, 816, 785, 757, 668, 650, 620 cm$^{-1}$; exact mass calcd for C$_{20}$H$_{32}$N$_2$O$_7$Si m/e 440.1979, obsd m/e 440.1903.

(2S)(4R)-N-(2-Amino-4,5-dimethoxybenzoyl)-2-(tert-butyidimethylsilyloxymethyl)-4-hydroxypyrrolidine (25)

A solution of hydrazine (6.59 g, 6.40 mL, 205.5 mmol) in MeOH (110 mL) was added dropwise to a solution of the nitro-compound 24 (18.1 g, 41.1 mmol), over anti-bumping granules and Raney Ni (2.6 g) in MeOH (325 mL) and heated at reflux. After 1 hour at reflux TLC (95% CHCl$_3$/MeOH) revealed some amine formation. The reaction mixture was treated with further Raney Ni (2.6 g) and hydrazine (6.40 mL) in MeOH (50 mL) and was heated at reflux for an additional 30 minutes at which point TLC revealed reaction completion. The reaction mixture was then treated with sufficient Raney Ni to decompose any remaining hydrazine and heated at reflux for a further 1.5 h. Following cooling to room temperature the mixture was filtered through a sinter and the resulting filtrate evaporated in vacuo. The resulting residue was then treated with CH$_2$Cl$_2$ (300 mL), dried (MgSO$_4$), filtered and evaporated in vacuo to provide the amine 25 as a green oil (16.03 g, 95%): $[α]^{22}_D$=−116.32° (c=0.31, CHCl$_3$); $^1$H NMR (270 MHz, CDCl$_3$) (Rotamers) δ 6.70 (s, 1H), 6.28 (s, 1H), 4.51-4.49 (m, 1H), 4.36-4.34 (m, 1H), 4.06-3.77 (m, 10H), 3.61-3.50 (m, 3H), 2.23-2.21 (m, 1H), 2.01-1.98 (m, 1H), 0.89 (s, 9H), 0.04 (s, 6H); $^{13}$C NMR (67.8 MHz, CDCl$_3$) (Rotamers) δ 170.2, 151.5, 141.2, 140.5, 112.2, 112.0, 101.1, 70.4, 62.6, 59.0, 56.9, 56.6, 55.8, 35.7, 25.9 and 25.7, 18.2, −5.4 and −5.5; MS (EI), m/z (relative intensity) 412 (M$^+$+2, 3), 411 (M$^+$+1, 10), 410 (M$^+$, 32), 354 (6), 353 (23), 263 (3), 212 (5), 181 (11), 180 (100), 179 (3), 165 (3), 164 (6), 152 (10), 137 (4), 136 (4), 125 (5), 120 (3), 100 (3), 94 (6), 75 (9), 73 (7), 57 (3); IR (CHCl$_3$) 3353 (br), 2953, 2930, 2857, 1623, 1594, 1558, 1517, 1464, 1435, 1404, 1260, 1234, 1215, 1175, 1119, 1060, 1005, 915, 836, 777, 755, 666 cm$^{-1}$; exact mass calcd for C$_{20}$H$_{34}$N$_2$O$_5$Si m/e 410.2237, obsd m/e 410.2281.

(2S)(4R)-N-[(2-Allyloxycarbonylamino)-4,5-dimethoxybenzoyl]-2-(tert-butyidimethylsilyloxymethyl)-4-hydroxypyrrolidine (26)

A solution of the amine 25 (16.03 g, 39 mmol) in CH$_2$Cl$_2$ (450 mL) was cooled to 0° C. (ice/acetone) and treated with pyridine (6.94 mL, 6.78 g, 85.8 mmol). A solution of allyl chloroformate (4.35 mL, 4.94 g, 40.95 mmol) in CH$_2$Cl$_2$ (90 mL) was then added dropwise to the stirred mixture. The reaction mixture was allowed to warm to room temperature and stirred for a further 1.5 h, at which point TLC (EtOAc) revealed complete consumption of amine 25. The reaction mixture was washed with saturated CuSO$_4$ (300 mL), H$_2$O (300 mL), brine (300 mL), dried (MgSO$_4$), filtered and evaporated in vacuo. The crude residue was purified by flash chromatography (35% EtOAc/Petroleum Ether) to afford the pure alloc-amino compound 26 as a clear oil (16.78 g, 87%): $[α]^{23}_D$=−93.35° (c=0.27, CHCl$_3$); $^1$H NMR (270 MHz, CDCl$_3$) (Rotamers) δ 8.93 (brs, 1H), 7.72 (s, 1H), 6.77 (s, 1H), 6.01-5.87 (m, 1H), 5.34 (dd, 1H, J=17.22, 3.12 Hz), 5.23 (dd, 1H, J=10.44, 1.29 Hz), 4.63-4.55 (m, 3H), 4.40-4.38 (m, 1H), 4.15-4.08 (m, 1H), 3.91 (s, 3H), 3.81 (s, 3H), 3.62-3.55 (m, 2.34-2.24 (m, 2H), 2.07-1.99 (m, 1H), 0.89 (s, 9H), 0.05 and 0.04 (s×2, 6H), $^{13}$C NMR (67.8 MHz, CDCl$_3$) (Rotamers) δ 169.5, 153.8, 150.9, 143.8, 132.5, 118.0, 115.9, 111.0, 104.6, 70.5, 65.8, 62.2, 59.0, 57.2, 56.2, 56.0, 35.7 and 31.1, 25.8, 18.1, −5.4 and −5.5; MS (EI), m/z (relative intensity) 496 (M$^+$+2, 6), 495 (M$^+$+1, 18), 494 (M$^+$, 50), 439 (11), 438 (29), 437 (100), 380 (4), 379 (14), 337 (13), 336 (4), 265 (15), 264 (91), 263 (4), 258 (6), 224 (4), 223 (15), 220 (11), 212 (7), 208 (4), 207 (11), 206 (75), 192 (5), 180 (20), 179 (18), 174 (15), 172 (4), 164 (7), 156 (5), 152 (5), 150 (6), 136 (4), 99 (9), 86 (16), 75 (10), 73 (11), 57 (6); IR (CHCl$_3$) 3337 (br), 2952, 2930, 2857, 1733, 1600, 1522, 1458, 1420, 1399, 1327, 1288, 1261, 1229, 1203, 1165, 1121, 1039, 1004, 931, 836, 777, 668 cm$^{-1}$; exact mass calcd for C$_{24}$H$_{38}$N$_2$O$_7$Si m/e 494.2448, obsd m/e 494.2365.

(2S)-N-[(2-Allyloxycarbonylamino)-4,5-dimethoxybenzoyl]-2-(tert-butyidimethylsilyloxymethyl)-4-oxopyrrolidine (27)

A solution of DMSO (7.24 mL, 7.97 g, 102 mmol) in CH$_2$Cl$_2$ (150 mL) was added dropwise over 2 hours to a solution of oxalyl chloride (25.5 mL of a 2.0 M solution in CH$_2$Cl$_2$, 51.0 mmol) at −60° C. (liq.N$_2$/CHCl$_3$) under a nitrogen atmosphere. After stirring at −50° C. for 1 hour, a solution of the alcohol 26 (16.75 g, 33.9 mmol) in CH$_2$Cl$_2$ (250 mL) was added dropwise over a period of 2 h. After 1 hour at −55° C., the mixture was treated dropwise with a solution of TEA (32.2 mL, 23.4 g, 231 mmol) in CH$_2$Cl$_2$ (100 mL) and allowed to warm to room temperature. The reaction mixture was treated with brine (250 mL) and washed with cold 1N HCl (2×300 mL). TLC (50% EtOAc/Petroleum Ether) analysis of the CH$_2$Cl$_2$ layer revealed complete reaction. The layers were separated and the organic phase washed with H$_2$O (300 mL), brine (300 mL), dried (MgSO$_4$), filtered and concentrated in vacuo to give the ketone 27 as an orange glass (16.37 g, 98%): $[α]^{21}_D$=−9.96° (c=1.51, CHCl$_3$); $^1$H NMR (270 MHz, CDCl$_3$) δ 8.69 (s, 1H), 7.82 (s, 1H), 6.75 (s, 1H), 6.01-5.89 (m, 1H), 5.36 (dd, 1H, J=17.22, 3.11 Hz), 5.28-5.23 (m, 1H), 5.20-4.95 (m, 1H), 4.65-4.62 (m, 2H), 4.20-3.83 (m, 9H), 3.67-3.56 (m, 1H), 2.74 (dd, 1H, J=17.86, 9.44 Hz), 2.52 (d, 1H, J=17.95 Hz), 0.87 (s, 9H), 0.05 (s, 6H); $^{13}$C NMR (67.8 MHz, CDCl$_3$) (Rotamers) δ 208.9, 169.1, 153.5, 151.3, 143.9, 132.4, 118.2, 114.4, 110.1, 104.6, 66.1, 65.8, 56.2, 56.0, 39.7, 25.6, 18.0, −5.7 and −5.8; MS (EI), m/z (relative intensity) 494 (M$^+$+2, 6), 493 (M$^+$+1, 16), 492 (M$^+$, 43), 437 (8), 436 (22), 435 (74), 377 (11), 336 (6), 335 (21), 334 (8), 294 (8), 265 (9), 264 (50), 250 (5), 223 (17), 220 (18), 208 (7), 207 (15), 206 (100), 192 (9), 180 (23), 179 (28), 172 (33), 171 (10), 164 (16), 155 (7), 152 (9), 150 (16), 136 (13), 115 (14), 108 (6), 88 (6), 75 (20), 73 (33), 59 (13), 58 (6), 57 (62), 56 (14); IR (NEAT) 3337 (br, NH), 3086, 3019, 2954, 2932, 2858, 1766, 1732, 1623, 1603, 1520, 1464, 1398, 1362, 1332, 1313, 1287, 1262, 1204, 1166, 1110, 1052, 1038, 1004, 938, 870, 838, 810, 756, 666, 621, 600 cm$^{-1}$; exact mass calcd for $C_{24}H_{36}N_2O_7Si$ m/e 492.2292, obsd m/e 492.2349.

(2S)-N-[(2-Allyloxycarbonylamino)-4,5-dimethoxybenzoyl]-2-(tert-butyidimethylsilyloxymethyl)-4-methylidinepyrrolidine (28)

Potassium tert-butoxide (21.2 mL of a 0.5 M solution in THF, 10.6 mmol) was added dropwise to a suspension of methyltriphenylphosphonium bromide (3.78 g, 10.6 mmol) in THF (11 mL) at 0° C. (ice/acetone) under nitrogen. After stirring for 2 hours at 0° C., a solution of ketone 27 (2.0 g, 4.07 mmol) in THF (7 mL) was added dropwise and the mixture allowed to warm to room temperature. After stirring for a further 45 minutes the reaction mixture was diluted with EtOAc (60 mL) and water (60 mL). The organic layer was separated, washed with brine, dried (MgSO$_4$), filtered and evaporated in vacuo to give a dark oil. Purification by flash chromatography (20% EtOAc/Petroleum Ether) isolated the pure olefin 28 as a transparent oil (1.71 g, 86%): $[\alpha]^{22}_D$=−44.55° (c=0.20, CHCl$_3$); $^1$H NMR (270 MHz, CDCl$_3$) (Rotamers) δ 8.85 (br s, 1H), 7.86 (s, 1H), 6.82 (s, 1H), 6.03-5.89 (m, 1H), 5.35 (ddd, 1H, J=17.22; 3.11,1.47 Hz), 5.24 (ddd, 1H, J=10.44, 2.75, 1.28 Hz), 4.99-4.92 (m, 2H), 4.70-4.57 (m, 3H), 4.23-3.57 (m, 10H), 2.72-2.68 (m, 2H), 0.96-0.85 (m, 9H), 0.09-0.03 (m, 6H); $^{13}$C NMR (67.8 MHz, CDCl$_3$) (Rotamers) δ 168.7, 153.6, 150.9, 143.6, 132.5, 132.2, 118.1, 115.3, 110.6, 107.1, 104.3, 65.7, 63.6, 56.3, 56.0, 33.1, 25.8, 18.1, −5.5 and −5.6; MS (EI), m/z (relative intensity) 492 (M$^+$+2, 7), 491 (M$^+$+1, 20), 490 (M$^+$, 50), 475 (4), 435 (10), 447 (3), 434 (29), 433 (94), 376 (4), 375 (13), 348 (5), 333 (11), 332 (6), 294 (3), 265 (16), 264 (100), 227 (8), 226 (24), 224 (5), 223 (18), 220 (15), 210 (4), 208 (5), 207 (13), 206 (96), 192 (7), 180 (18), 179 (25), 170 (21), 169 (8), 168 (28), 164 (13), 152 (7), 150 (13), 136 (10), 108 (5), 96 (5), 95 (12), 94 (7), 89 (8), 82 (25), 75 (20), 73 (30), 59 (7), 58 (5), 57 (41), 56 (7), 55 (4); IR (NEAT) 3324 (br, NH), 3082, 2953, 2930, 2857, 1732, 1600, 1523, 1490, 1464, 1419, 1397, 1360, 1333, 1287, 1259, 1228, 1203, 1172, 1115, 1039, 1004, 939, 837, 814, 777 666 cm$^{-1}$.

(2S)-N-[(2-Allyloxycarbonylamino)-4,5-dimethoxybenzoyl]-2-(hydroxymethyl)-4-methylidinepyrrolidine (29)

A solution of TBAF (4.29 mL of a 1M solution in THF, 4.29 mmol) was added to the silyl-ether 28 (1.68 g, 3.43 mmol) in THF (45 mL) at 0° C. (ice/acetone). The reaction mixture was allowed to warm to room temperature and after 1 hour TLC (50% EtOAc/Pet-Ether 40°-60°) revealed the complete disappearance of starting material. Saturated NH$_4$Cl (110 mL) was added and the reaction mixture extracted with EtOAc (3×50 mL), washed with brine (100 mL), dried (MgSO$_4$) and evaporated in vacuo to give a dark orange oil. Purification by flash chromatography (99% CHCl$_3$/MeOH) provided the pure alcohol 29 as a white solid (1.15 g, 89%): $[\alpha]^{21}_D$=−13.17° (c=0.15, CHCl$_3$); $^1$H NMR (270 MHz, CDCl$_3$) δ 8.59 (br s, 1H), 7.69 (s, 1H), 6.82 (s, 1H), 6.03-5.89 (m, 1H), 5.35 (ddd, 1H, J=17.22, 3.11, 1.65 Hz), 5.24 (ddd, 1H, J=10.44, 2.75, 1.28 Hz), 5.02-4.94 (m, 2H), 4.66-4.62 (m, 3H), 4.23-3.57 (m, 11H), 2.77 (dd, 1H, J=15.94, 8.42 Hz), 2.48 (d, 1H, J=15.94 Hz); $^{13}$C NMR (67.8 MHz, CDCl$_3$) δ 170.3, 153.8, 151.0, 144.2, 143.1, 132.5, 131.2, 118.1, 115.9, 110.4, 108.1, 104.9, 65.8, 65.1, 59.8, 56.4, 56.0, 54.2, 34.1; MS (EI), m/z (relative intensity) 378 (M$^+$+2, 3), 377 (M$^+$+1, 14), 376 (M$^+$, 51), 319 (3), 265 (10), 264 (62), 263 (4), 259 (8), 224 (4), 223 (18), 220 (17), 208 (5), 207 (14), 206 (100), 192 (8), 190 (5), 180 (27), 179 (29), 178 (4), 164 (23), 163 (4), 152 (12), 151 (6), 150 (19), 137 (5), 136 (22), 135 (6), 125 (6), 120 (6), 113 (6), 112 (31), 109 (6), 108 (11), 95 (4), 94 (9), 82 (28), 80 (8), 67 (5), 57 (5), 54 (7), 53 (7); IR (NUJOL$^7$) 3341 and 3245 (br, OH and NH), 3115, 2918, 2850, 1727, 1616, 1540, 1464, 1399, 1378, 1351, 1283, 1264, 1205, 1179, 1117, 1055, 1040, 996, 946, 909, 894, 855, 823, 768, 754, 722, 696, 623, 602 cm$^{-1}$; exact mass calcd for $C_{19}H_{24}N_2O_6$ m/e 376.1634, obsd m/e 376.1614.

(11S,11aS)-10-Allyloxycarbonyl-7,8-dimethoxy-11-hydroxy-2-methylidene-1,2,3,10,11,11a-hexahydro-5H-pyrrolo[2,1-c][1,4]benzodiazepin-5-one (30)

A solution of DMSO (0.75 mL, 0.82 g, 10.5 mmol) in CH$_2$Cl$_2$ (27 mL) was added dropwise over 38 minutes to a solution of oxalyl chloride (2.64 mL of a 2.0 M solution in CH$_2$Cl$_2$, 5.27 mmol) at −45° C. (liq.N$_2$/Chlorobenzene) under a nitrogen atmosphere. After stirring at −45° C. for 1 h, a solution of the alcohol 29 (1.10 g, 2.93 mmol) in CH$_2$Cl$_2$ (27 mL) was added dropwise over 1 hour at −45° C. After 1 hour at −45° C., the mixture was treated dropwise with a solution of TEA (1.71 mL, 1.24 g, 12.29 mmol) in CH$_2$Cl$_2$ (15 mL) over 40 minutes at −45° C. After a further 30 minutes, the reaction mixture was allowed to warm to room temperature and was diluted with CH$_2$Cl$_2$ (50 mL), washed with 1N HCl (50 mL), H$_2$O (50 mL), brine (50 mL), dried (MgSO$_4$), filtered and evaporated in vacuo. TLC (80% EtOAc/Petroleum Ether) of the crude material revealed reaction completion. Purification by flash chromatography (60% EtOAc/Petroleum Ether) furnished the protected carbinolamine 30 as a white glass (0.45 g, 41%): $[\alpha]^{22}_D$=+236.51° (c=0.14, CHCl$_3$); $^1$H NMR (270 MHz, CDCl$_3$) δ 7.23 (s, 1H), 6.69 (s, 1H), 5.83-5.81 (m, 1H), 5.60-5.58 (m, 1H), 5.34-5.23 (m, 4H), 4.74-4.66 (m, 1H), 4.50-4.40 (m, 1H), 4.30 (d, 1H, J=15.94 Hz), 4.15 (d, 1H, J=15.93 Hz), 3,96-3.86 (m, 7H), 3.65 (t, 1H, J=8.61 Hz), 2.92 (dd, 1H, 16.21, 9.07 Hz), 2.70 (d, 1H, J=15.94 Hz); $^{13}$C NMR (67.8 MHz, CDCl$_3$) δ 166.7, 156.0, 150.8, 148.4, 141.8, 131.7, 128.5, 125.2, 118.1, 112.4, 110.3, 109.8, 85.9, 66.8, 59.6, 56.3, 56.1, 50.7, 35.0; MS (EI), m/z (relative intensity) 376 (M$^+$+2, 6), 375 (M$^+$+1, 22), 374 (M$^+$, 100), 346 (5), 293 (8), 288 (10), 271 (5), 265 (11), 264 (67), 248 (5), 237 (5), 223 (10), 220 (9), 209 (6), 208 (42), 207 (14), 206 (70), 192 (7), 190 (5), 180 (17), 179 (16), 165 (8), 164 (15), 153 (5), 152 (10), 150 (12), 149 (7), 137 (6), 136 (10), 135 (5), 125 (8), 110 (8), 108 (5), 94 (5), 83 (5), 82 (59), 80 (7),; IR (CHCl$_3$) 3275 (br, OH), 3075, 2936, 2851, 1706, 1624, 1604, 1516, 1457, 1436, 1403, 1368, 1312, 1301, 1278, 1262, 1218, 1119, 1074, 1045, 940, 916, 893, 867, 851, 666, 637 cm$^{-1}$; exact mass calcd for $C_{19}H_{22}N_2O_6$ m/e 374.1478, obsd m/e 374.1687.

(11aS)-7,8-Dimethoxy-2-methylidene-1,2,3,11a-tetrahydro-5H-pyrrolo[2,1-c][1,4]benzodiazepin-5-one (31, UP2064, MMY-SJG)

A catalytic amount of tetrakis(triphenylphosphine)palladium (32.4 mg, 28.1 μmol) was added to a stirred solution of the Alloc-protected carbinolamine 30 (0.42 g, 1.12 mmol), triphenylphosphine (14.7 mg, 56.2 μmol) and pyrrolidine (83.9 mg, 1.18 mmol) in $CH_2Cl_2$ (55 mL). After 2.5 hours stirring at room temperature under a nitrogen atmosphere, TLC (95% $CHCl_3$/MeOH) revealed the complete consumption of starting material. The solvent was evaporated in vacuo and the crude residue was purified by flash chromatography ($CHCl_3$) to afford the novel PBD (31, MMY-SJG, UP2064) as a yellow oil which was repeatedly evaporated in vacuo with $CHCl_3$ in order to provide the N10-C11 imine form (259 mg, 85%): $[\alpha]^{22}_D=+583.14°$ (c=1.42, $CHCl_3$); $^1H$ NMR (270 MHz, $CDCl_3$) δ 7.69 (d, 1H, J=4.39 Hz), 7.51 (s, 1H), 6.82 (s, 1H), 5.21-5.17 (m, 2H), 4.44-4.23 (m, 2H), 3.96-3.81 (m, 7H), 3.17-3.08 (m, 1H), 2.95 (d, 1H, J=14.29 Hz); $^{13}C$ NMR (67.8 MHz, $CDCl_3$) δ 164.7, 162.6, 151.5, 147.6, 141.6, 140.8, 119.8, 111.2, 109.4, 109.4, 56.2, 56.1, 53.8, 51.4, 35.5; MS (EI), m/z (relative intensity) 273 ($M^++1$, 16), 272 ($M^+$, 100), 271 (35), 270 (9), 255 (5), 243 (7), 241 (7), 230 (6), 228 (6), 226 (5), 212 (3), 192 (4), 191 (16), 165 (4), 164 (19), 163 (4), 136 (22), 93 (6), 82 (7), 80 (3), 53 (3); IR (NEAT) 3312 (br), 3083, 2936, 2843, 1624, 1603, 1505, 1434, 1380, 1264, 1217, 1180, 1130, 1096, 1069, 1007, 935, 895, 837, 786, 696, 666, 594, 542 $cm^{-1}$; exact mass calcd for $C_{15}H_{16}N_2O_3$ m/e 272.1161, obsd m/e 272.1154.

Example 1(d)

Figure 4:
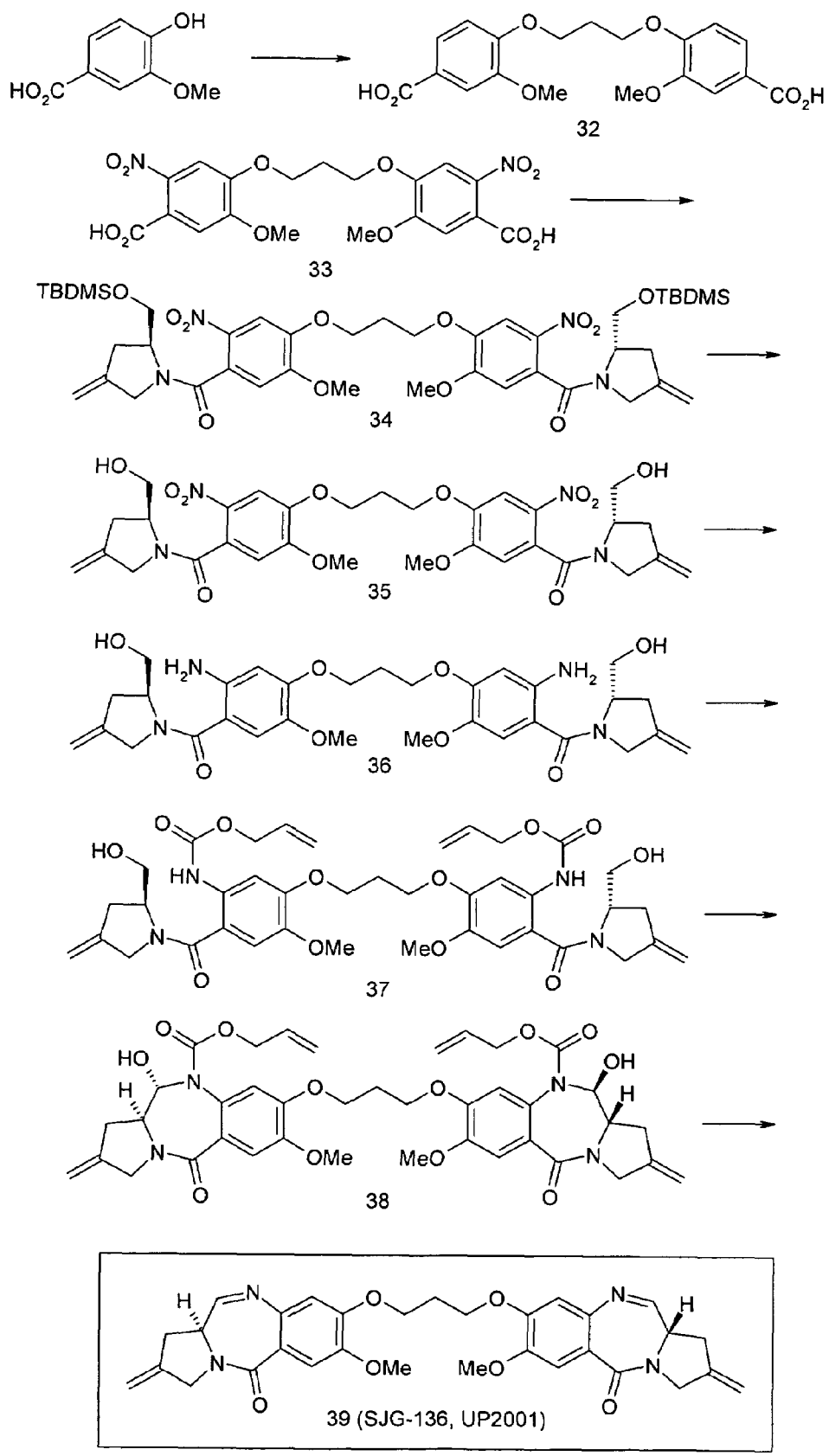

Synthesis of the PBD Dimer SJG-136 (39, UP2001) (see FIG. 4)

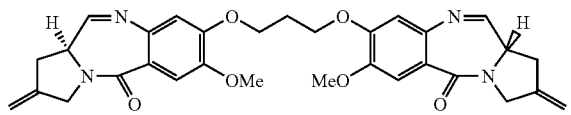

1=, 3=-Bis(4-carboxy-2-methoxyphenoxy)propane (32)

A solution of diiodopropane (8.79 g, 29.7 mmol) in THF (50 mL), was added dropwise over a period of 4 hours to a vigorously stirred solution of vanillic acid (10 g, 59.5 mmol) in THF (100 mL) and aqueous NaOH (225 mL, 0.5 M) at 65° C. in the absence of light (foil-wrapped flask). After heating at reflux for 48 hours in the dark, the suspension was cooled, washed with hexane (3×100 mL) and the THF removed by evaporation in vacuo. The aqueous residue was acidified to pH 1 with conc. HCl and the resultant precipitate collected by filtration, dried and recrystallised from glacial acetic acid to afford the corresponding bis-carboxylic acid (32) as a white crystalline solid (9.4 g, 84%). mp 238-240° C.; 1H-NMR (DMSO-d6): δ 2.23 (t, 2H, J=6.0 Hz, H13), 3.80 (s, 6H, $CH_3O$), 4.20 (t, 4H, J=6.0 Hz, H12), 7.09 (d, 2H, J=8.4 Hz, H10), 7.45 (d, 2H, J=1.8 Hz, H6) 7.54 (dd, 2H, J=8.4 Hz, 1.8 Hz, H9), 12.76 (bs, 2H, $CO_2H$); 13C-NMR (DMSO-d6) δ 28.4 (C13), 55.4 (CH3O), 64.8 (C12), 111.9 (C9), 112.0 (C6), 122.9 (C10), 123.0 (Q), 148.3 (Q), 151.6 (Q), 167.0 (C=O). IR (KBr): v=3600-2000, 1680 (C=O), 1600 (C=C), 1515, 1465, 1430, 1345, 1310, 1270, 1225 (C—O—C), 1180, 1140, 1115, 1030, 990, 970, 950, 925, 875, 850, 825, 765, 725, 645 $cm^{-1}$. MS (EI): m/z (relative intensity) 376 (M+, 28), 360 (3), 249 (2), 209 (45), 165 (29), 153 (16), 151 (19), 137 (19), 121 (7), 78 (15), 44 (100); HRMS: Calcd for $C_{19}H_{20}O_8$=376.1158. found 376.1168.

1=,3=-Bis(4-carboxy-2-methoxy-5-nitrophenoxy) propane (33)

The diacid 32 (2.0 g, 5.30 mmol) was added portionwise to conc. $HNO_3$ (40 mL) at −10° C. and stirred at room temperature over 12 h. The reaction mixture was poured on to ice (400 mL) and the resulting precipitate collected by filtration, washed with ether (3×50 mL) and dried to afford the nitro acid (33) as a yellow solid (1.73 g, 70%). m.p. 243-246° C. 1H-NMR (DMSO-d6): δ 2.25 (t, 2H, J=5.9 Hz, H13), 3.90 (s, 6H, CH3O), 4.27 (t, 4H, J=5.9 Hz, H12), 7.29 (s, 2H, H6), 7.62 (s, 2H, H9), 13.6 (bs, 2H, $CO_2H$). 13C-NMR (DMSO-d6) δ 28.0 (C13), 56.3 (CH3O), 65.7 (C12), 108.0 (C9), 111.2 (C6), 121.1 (C5), 141.3 (Q), 149.1 (C8), 151.7 (Q), 165.9 (C=O). IR (KBr): v=3620-2280, 1700 (C=O), 1595 (C=C), 1570, 1515 (NO2), 1460, 1415, 1350 (NO2), 1270, 1210, 1180, 1135, 1045, 930, 880, 810, 750, 730, 645 cm−1. MS (EI): m/z (relative intensity) 467 (MH+, 1), 450 (1), 436 (3), 423 (8), 378 (4), 268 (1), 255 (4), 236 (4), 210 (7), 194 (2), 182 (7), 164 (14), 153 (2), 123 (3), 91 (6), 77 (3), 55 (5), 44 (100). HRMS (EI) m/z calcd for $C_{19}H_{18}N_2O_{12}$=466.0860. found 466.0871.

(2S)-1,1=-[[(Propane-1,3-diyl)dioxy]bis[(2-nitro-5-methoxy-1,4-phenylene)carbonyl]]bis[2-(tert-butyldimethylsilyloxymethyl)-4-methylidenepyrrolidine] (34)

A catalytic amount of DMF (2 drops) was added to a solution of the dimer acid 33 (0.66 g, 1.42 mmol) and oxalyl chloride (0.31 mL, 0.45 g, 3.55 mmol) in THF (12 mL). The reaction mixture was stirred for 16 hours under nitrogen, concentrated in vacuo, and redissolved in THF (10 mL). The resulting solution of bis-acid chloride was added dropwise to the amine 58 (0.65 g, 2.86 mmol), $H_2O$ (0.84 mL) and TEA (0.83 mL, 0.60 g, 5.93 mmol) in THF (2 mL) at 0° C. (ice/acetone) under nitrogen. The reaction mixture was allowed to warm to room temperature and stirred for a further 2 hours at which time TLC (EtOAc) revealed reaction completion. After removal of the THF by evaporation in vacuo, the residue was partitioned between $H_2O$ (100 mL) and EtOAc (100 mL). The aqueous layer was washed with EtOAc (3×50 mL), and the combined organic layers washed with saturated $NH_4Cl$ (100 mL), brine (100 mL), dried ($MgSO_4$), filtered and concentrated in vacuo to give the crude product as a dark orange oil. Purification by flash chromatography (50% EtOAc/Petroleum Ether) afforded the pure amide 34 as a pale yellow glass (0.93 g, 74%): $[\alpha]^{21}_D=-51.1°$ (c=0.08, $CHCl_3$); $^1H$ NMR (270 MHz, $CDCl_3$) (Rotamers) δ 7.77 and 7.74 (s×2, $2H_{arom}$), 6.81 and 6.76 (s×2, $2H_{arom}$), 5.09-4.83 (m, 4H, $NCH_2C=CH_2$), 4.60 (m, 2H, $NCHCH_2OTBDMS$), 4.35-4.31 (m, 4H, $OCH_2CH_2CH_2O$), 4.08-3.74 (m, 14H, $NCHCH_2OTBDMS$, $NCH_2C=CH_2$ and $OCH_3$), 2.72-2.45 (m, 6H, $NCH_2C=CH_2CH_2$ and $OCH_2CH_2CH_2O$), 0.91 and 0.79 (s×2, 18H, $SiC(CH_3)_3$), 0.09, −0.09, and −0.12 (s×3, 12H, $Si(CH_3)_2$); $^{13}C$ NMR (67.8 MHz, $CDCl_3$) (Rotamers) δ 166.2 (NC=O), 154.7 and 154.5 ($C_{quat}$), 148.4 and 148.2 ($C_{quat}$), 144.1 and 143.2 ($C_{quat}$), 137.2 ($C_{quat}$), 128.2 and 127.4 ($C_{quat}$), 110.1 and 108.6 ($C—H_{arom}$), 109.1 and 108.3 ($C—H_{arom}$), 107.5 ($NCH_2C=CH_2$), 65.7 and 65.5 ($OCH_2CH_2CH_2O$), 63.9 and 62.6 ($NCHCH_2OTBDMS$), 60.2 ($NCHCH_2OTBDMS$), 58.1 and 56.6 ($OCH_3$), 52.8 and 50.5 ($NCH_2C=CH_2$), 35.0 and 33.9 ($NCH_2C=CH_2$), 30.8 and 28.6 ($OCH_2CH_2CH_2O$), 25.8 and 25.7 ($SiC(CH_3)_3$), 18.2 ($SiC(CH_3)_3$), −5.5 and −5.6 ($Si(CH_3)_2$); MS (EI), m/z (relative intensity) 885 ($M^+$, 7), 828 (M−$^t$Bu, 100), 740 (M-CH$_2$OTBDMS, 20), 603 (3), 479 (26), 391 (27), 385 (25), 301 (7), 365 (10), 310 (14), 226 (8), 222 (13), 170 (21), 168 (61), 82 (39), 75 (92); IR (NUJOL$^7$) 2923, 2853, 2360, 1647, 1587, 1523 (NO$_2$), 1461, 1429, 1371, 1336 (NO$_2$), 1277, 1217, 1114, 1061, 1021, 891, 836 772, 739 cm$^{-1}$.

(2S)-1,1'-[[(Propane-1,3-diyl)dioxy]bis[(2-nitro-5-methoxy-1,4-phenylene)carbonyl]]bis[2-(hydroxymethyl)-4-methylidenepyrrolidine] (35)

A solution of TBAF (3.98 mL of a 1M solution in THF, 3.98 mmol) was added to the bis-silyl ether 34 (1.41 g, 1.59 mmol) in THF (35 mL) at 0° C. (ice/acetone). The reaction mixture was allowed to warm to room temperature and after a further 30 minutes saturated NH$_4$Cl (120 mL) was added. The aqueous solution was extracted with EtOAc (3×80 mL), washed with brine (80 mL), dried (MgSO$_4$), filtered and evaporated in vacuo to give a dark orange oil which was purified by flash chromatography (97% CHCl$_3$/MeOH) to provide the pure diol 35 as a light orange solid (0.98 g, 94%): $[\alpha]^{19}_D$=−31.9° (c=0.09, CHCl$_3$); $^1$H NMR (270 MHz, CDCl$_3$) (Rotamers) δ 7.75 and 7.71 (s×2, 2H$_{arom}$), 6.96 and 6.84 (s×2, 2H$_{arom}$), 5.08, 5.02 and 4.88 (br s×3, 4H, NCH$_2$C=CH$_2$), 4.61-4.50 (m, 2H, NCHCH$_2$OH), 4.35-4.33 (m, 4H, OCH$_2$CH$_2$CH$_2$O), 4.02-3.65 (m, 14H, NCHCH$_2$OH, NCH$_2$C=CH$_2$ and OCH$_3$), 2.88-2.43 (m, 6H, NCH$_2$C=CH$_2$CH$_2$ and OCH$_2$CH$_2$CH$_2$O); $^{13}$C NMR (67.8 MHz, CDCl$_3$) (Rotamers) δ 167.9 and 166.9 (NC=O), 154.9 and 154.3 (C$_{quat}$), 148.4 and 148.2 (C$_{quat}$), 143.3 and 142.6 (C$_{quat}$), 137.2 and 137.0 (C$_{quat}$), 127.6 and 127.3 (C$_{quat}$), 109.1 (C—H$_{arom}$), 108.4 (NCH$_2$C=CH$_2$), 108.2 (C—H$_{arom}$), 65.6 and 65.4 (OCH$_2$CH$_2$CH$_2$O), 64.5 and 63.3 (NCHCH$_2$OH), 60.5 and 60.0 (NCHCH$_2$OH), 56.8 and 56.7 (OCH$_3$), 52.9 (NCH$_2$C=CH$_2$), 35.0 and 34.3 (NCH$_2$C=CH$_2$CH$_2$), 29.6 and 28.6 (OCH$_2$CH$_2$CH$_2$O); MS (FAB) (Relative Intensity) 657 (M$^+$+1, 10), 639 (M-OH, 2), 612 (1), 544 (M-NCH$_2$CCH$_2$CH$_2$CHCH$_2$OH, 4), 539 (1), 449 (16), 433(9), 404 (8), 236 (32), 166 (65), 151 (81), 112 (82), 82 (100); IR (NUJOL$^7$) 3600-3200 (br, OH), 2923, 2853, 2360, 1618, 1582, 1522 (NO$_2$), 1459, 1408, 1375, 1335 (NO$_2$), 1278, 1218, 1061, 908, 810, 757 cm$^{-1}$.

(2S)-1,1'-[[(Propane-1,3-diyl)dioxy]bis[(2-amino-5-methoxy-1,4-phenylene)carbonyl]]bis[2-(hydroxymethyl)4-methylidenepyrrolidine] (36)

A mixture of the diol 35 (0.98 g, 1.49 mmol) and SnCl$_2$.2H$_2$O (3.36 g, 14.9 mmol) in MeOH (35 mL) was heated at reflux and the progress of the reaction monitored by TLC (90% CHCl$_3$/MeOH). After 45 minutes, the MeOH was evaporated in vacuo and the resulting residue was cooled (ice), and treated carefully with saturated NaHCO$_3$ (120 mL). The mixture was diluted with EtOAc (120 mL), and after 16 hours stirring at room temperature the inorganic precipitate was removed by filtration through celite. The organic layer was separated, washed with brine (100 mL), dried (MgSO$_4$), filtered and evaporated in vacuo to give a brown solid. Flash chromatography (95% CHCl$_3$/MeOH) afforded the pure bis-amine 36 as an orange solid (0.54 g, 61%): $[\alpha]^{19}_D$=−31.8° (c=0.30, CHCl$_3$); $^1$H NMR (270 MHz, CDCl$_3$) δ 6.74 (s, 2H$_{arom}$), 6.32 (s, 2H$_{arom}$), 5.00 (br s, 2H, NCH$_2$C=CH$_2$), 4.93 (br s, 2H, NCH$_2$C=CH$_2$), 4.54 (br s, 2H, NCHCH$_2$OH), 4.24-4.14 (m, 4H, OCH$_2$CH$_2$CH$_2$O), 3.98-3.50 (m, 14H, NCHCH$_2$OH, NCH$_2$C=CH$_2$ and OCH$_3$), 2.76 (dd, 2H, J=8.61, 15.91 Hz, NCH$_2$C=CH$_2$CH$_2$), 2.46-2.41 (m, 2H, NCH$_2$C=CH$_2$CH$_2$), 2.33-2.28 (m, 2H, OCH$_2$CH$_2$CH$_2$O); $^{13}$C NMR (67.8 MHz CDCl$_3$) δ 171.0 (NC=O), 151.0 (C$_{quat}$), 143.5 (C$_{quat}$), 141.3 (C$_{quat}$), 140.6 (C$_{quat}$), 112.4 (C—H$_{arom}$), 111.9 (C$_{quat}$), 107.8 (NCH$_2$C=CH$_2$), 102.4 (C—H$_{arom}$), 65.2 (OCH$_2$CH$_2$CH$_2$O), 65.0 (NCHCH$_2$OH), 59.8 (NCHCH$_2$OH), 57.1 (OCH$_3$), 53.3 (NCH$_2$C=CH$_2$), 34.4 (NCH$_2$C=CH$_2$CH$_2$), 29.0 (OCH$_2$CH$_2$CH$_2$O); MS (FAB) (Relative Intensity) 596 (M$^+$, 13), 484 (M-NCH$_2$CCH$_2$CH$_2$CHCH$_2$OH, 14), 389 (10), 371 (29), 345 (5), 224 (8), 206 (44), 166 (100), 149 (24), 112 (39), 96 (34), 81 (28); IR (NUJOL$^7$) 3600-3000 (br, OH), 3349 (NH$_2$), 2922, 2852, 2363, 1615, 1591 (NH$_2$), 1514, 1464, 1401, 1359, 1263, 1216, 1187, 1169, 1114, 1043, 891, 832, 761 cm$^{-1}$.

(2S,4R)&(2S,4S)-1,1'-[[(Propane-1,3-diyl)dioxy]bis[(2-amino-5-methoxy-1,4-phenylene)carbonyl]]bis[2-(hydroxymethyl)-4-methylpyrrolidine] (36)

A solution of hydrazine (23 mg, 23 μL, 0.72 mmol) in MeOH (5 mL) was added dropwise to a solution of the diol 35 (95 mg, 0.145 mmol) and Raney Ni (20 mg) in MeOH (15 mL) heated at reflux. After 1 hour at reflux TLC (90% CHCl$_3$/MeOH) revealed some amine formation. The reaction mixture was treated with further Raney Ni (20 mg) and hydrazine (23 mg, 23 μL, 0.72 mmol) in MeOH (5 mL) and was heated at reflux for an additional 30 minutes at which point TLC revealed complete reaction. The reaction mixture was then treated with enough Raney Ni to decompose any remaining hydrazine and heated at reflux for a further 1.5 hours. Following cooling to room temperature the mixture was filtered through a sinter and the resulting filtrate evaporated in vacuo. The resulting residue was then treated with CH$_2$Cl$_2$ (30 mL), dried (MgSO$_4$), filtered and evaporated in vacuo to provide the bis-amine (36) as a yellow oil (54 mg, 63%): $^1$H NMR (270 MHz, CDCl$_3$) (diastereoisomers) δ 6.73 (s, 2H$_{arom}$), 6.32 (s, 2H$_{arom}$), 4.60-4.30 (m, 2H, NCHCH$_2$OH), 4.19 (t, 4H, J=5.87 Hz, OCH$_2$CH$_2$CH$_2$O), 3.78-3.50 (m, 14H, NCHCH$_2$OH, NCH$_2$CHCH$_3$ and OCH$_3$), 2.40-1.55 (m, 8H, NCH$_2$CHCH$_3$, OCH$_2$CH$_2$CH$_2$O and NCH$_2$CHCH$_3$CH$_2$), 1.00-0.95 (m, 6H, NCH$_2$CHCH$_3$); MS (EI), m/z (relative intensity) 600 (M$^+$, 16), 459 (46), 345 (16), 206 (13), 186 (17), 180 (31), 166 (37), 149 (6), 142 (76), 100 (6), 98 (13), 97 (29), 84 (81), 69 (7), 55 (100).

(2S)-1,1'-[[(Propane-1,3-diyl)dioxy]bis[(2-allyloxycarbonylamino-5-methoxy-1,4-phenylene)carbonyl]]bis[2-(hydroxymethyl)-4-methylidenepyrrolidine] (37)

Pyridine (0.47 mL, 0.46 g, 5.82 mmol) was added to a stirred solution of the bis-amine 36 (0.857 g, 1.44 mmol) in CH$_2$Cl$_2$ (30 mL) at 0° C. (ice/acetone). The cool mixture was then treated dropwise with a solution of allyl chloroformate (0.33 mL, 0.38 g, 3.15 mmol) in CH$_2$Cl$_2$ (10 mL). After 2.5 hours stirring at room temperature, the mixture was diluted with CH$_2$Cl$_2$ (60 mL), washed with 1N HCl (2×50 mL), H$_2$O (80 mL), brine (80 mL), dried (MgSO$_4$), filtered and evaporated in vacuo. The crude residue was purified by flash chromatography (70-100% EtOAc/Petroleum Ether) to afford the allyl cartamate compound 37 as a slightly orange glass (0.548 g, 50%): $^1$H NMR (270 MHz, CDCl$_3$) δ 8.58 (br s, 2H, NH), 7.56 (s, 2H$_{arom}$), 6.78 (s, 2H$_{arom}$), 6.03-5.88 (m, 2H, NCO$_2$CH$_2$CH=CH$_2$), 5.39-5.21 (m, 4H, NCO$_2$CH$_2$CH=CH$_2$), 5.00 (br s, 2H, NCH$_2$C=CH$_2$), 4.93 (br s, 2H, NCH$_2$C=CH$_2$), 4.70-4.57 (m, 4H, NCO$_2$CH$_2$CH=CH$_2$), 4.30-4.25 (m, 4H, OCH$_2$CH$_2$CH$_2$O), 4.17-3.90 (m, 8H, NCHCH$_2$OH and NCH$_2$C=CH$_2$), 3.81-3.54 (m, 8H, NCHCH$_2$OH and OCH$_3$), 2.76 (dd, 2H, J=8.52, 15.85 Hz, NCH$_2$C=CH$_2$CH$_2$), 2.49-2.44 (m, 2H, NCH$_2$C=CH$_2$CH$_2$), 2.36-2.28 (m, 2H, OCH$_2$CH$_2$CH$_2$O); $^{13}$C NMR (67.8 MHz, CDCl$_3$) δ 170.3 (NC=O$_{amide}$), 153.8 (NC=O$_{carbamate}$), 150.5 (C$_{quat}$), 144.8 (C$_{quat}$), 143.1 (C$_{quat}$), 132.5 (NCO$_2$CH$_2$CH=CH$_2$), 130.7 (C$_{quat}$), 118.1 (NCO$_2$CH$_2$CH=CH$_2$), 116.8 (C$_{quat}$), 110.9 (C—H$_{arom}$), 108.1 (NCH$_2$C=CH$_2$), 106.9 (C—H$_{arom}$), 65.7 (NCO$_2$CH$_2$CH=CH$_2$), 65.4 (OCH$_2$CH$_2$CH$_2$O), 65.1 (NCHCH$_2$OH), 59.8 (NCHCH$_2$OH), 56.5 (OCH$_3$), 53.9 (NCH$_2$C=CH$_2$), 34.2 (NCH$_2$C=CH$_2$CH$_2$), 29.7 and 29.2 (OCH$_2$CH$_2$CH$_2$O); MS (FAB) (Relative Intensity) 765 (M$^+$+1, 10), 652 (M-NCH$_2$CCH$_2$CH$_2$CHCH$_2$OH, 32), 594 (4), 539 (2), 481 (51), 441 (31), 290 (3), 249 (13), 232 (38), 192 (83), 166 (49), 149 (32), 114 (100).

1,1=-[[(Propane-1,3-diyl)dioxy]bis[(11S,11aS)-10-(allyloxycarbonyl)-11-hydroxy-7-methoxy-2-methylidene-1,2,3,10,11,11a-hexahydro-5H-pyrrolo[2,1-c][1,4]benzodiazepin-5-one] (38)

A solution of the bis-alloc compound 37 (150 mg, 0.196 mmol) in CH$_2$Cl$_2$/CH$_3$CN (12 mL, 3:1) was treated with 4 Å powdered molecular sieves (0.2 g) and NMO (70 mg, 0.598 mmol). After 15 minutes stirring at room temperature, TPAP (7 mg, 19.9 μmol) was added and stirring continued for a further 2 hours at which time TLC (95% CHCl$_3$/MeOH) indicated formation, of the fully cyclised product along with the presumed semi-cyclised product 38, and unreacted starting material 37 present in the reaction mixture. The mixture was then treated with a further quantity of NMO (35 mg, 0.299 mmol) and TPAP (3.5 mg, 9.96 μmol), and allowed to stir for a further 0.5 hours when TLC revealed reaction completion. The solvent was evaporated in vacuo and the black residue was subjected to flash chromatography (98% CHCl$_3$/MeOH) to provide the pure protected carbinolamine 38 as a white solid (47 mg, 32%): $^1$H NMR (270 MHz, CDCl$_3$) δ 7.23 (s, 2H$_{arom}$), 6.74 (s, 2H$_{arom}$), 5.90-5.65 (m, 2H, NCO$_2$CH$_2$CH=CH$_2$), 5.57 (d, 2H, J=8.24 Hz, NCHCHOH), 5.26-5.07 (m, 8H, NCH$_2$C=CH$_2$ and NCO$_2$CH$_2$CH=CH$_2$), 4.67-4.10 (m, 14H, NCO$_2$CH$_2$CH=CH$_2$, NCH$_2$C=CH$_2$, OCH$_2$CH$_2$CH$_2$O and OH), 3.89 (s, 6H, OCH$_3$), 3.63 (m, 2H, NCHCHOH), 2.91 (dd, 2H, J=8.79, 15.76 Hz, NCH$_2$C=CH$_2$CH$_2$), 2.68 (d, 2H, J=16.10 Hz, NCH$_2$C=CH$_2$CH$_2$), 2.42-2.24 (m, 2H, OCH$_2$CH$_2$CH$_2$O); $^{13}$C NMR (67.8 MHz, CDCl$_3$) δ 166.7 (NC=O$_{amide}$), 150.1 (C$_{quat}$), 149.0 (C$_{quat}$), 141.7 (C$_{quat}$), 131.7 (NCO$_2$CH$_2$CH=CH$_2$), 130.6 (C$_{quat}$), 128.9 (C$_{quat}$), 128.8 (C$_{quat}$), 118.3 (NCO$_2$CH$_2$CH=CH$_2$), 114.7 (C—H$_{arom}$), 110.7 (C—H$_{arom}$), 109.8 (NCH$_2$C=CH$_2$), 85.9 (NCHCHOH), 66.9 (NCO$_2$CH$_2$CH=CH$_2$), 66.0 (OCH$_2$CH$_2$CH$_2$O), 59.7 (NCHCHOH), 56.1 (OCH$_3$), 50.7 (NCH$_2$C=CH$_2$), 35.0 (NCH$_2$C=CH$_2$CH$_2$), 29.7 and 29.1 (OCH$_2$CH$_2$CH$_2$O); MS (FAB) (Relative Intensity) 743 (M$^+$-17, 16), 725 (17), 632 (13), 574 (8), 548 (13), 490 (10), 481 (9), 441 (7), 425 (6), 257 (12), 232 (20), 192 (46), 166 (52), 149 (100), 91 (59); IR (NUJOL$^7$) 3234 (br, OH), 2923, 2853, 2361, 1707, 1604, 1515, 1464, 1410, 1377, 1302, 1267, 1205, 1163, 1120, 1045, 999, 955, 768, 722 cm$^{-1}$.

1,1=-[[(Propane-1,3-diyl)dioxy]bis[(11aS)-7-methoxy-2-methylidene-1,2,3,11a-tetrahydro-5H-pyrrolo[2,1-c][1,4]benzodiazepin-5-one] (39, SJG-136)

A catalytic amount of tetrakis(triphenylphosphine)palladium (11 mg, 9.52 μmol) was added to a stirred solution of the bis-alloc-carbinolamine 38 (139 mg, 0.183 mmol), triphenylphosphine (4.8 mg, 18.3 μmol) and pyrrolidine (27 mg, 0.380 mmol) in CH$_2$Cl$_2$/CH$_3$CN (13 mL, 10:3) at 0° C. (ice/acetone) under a nitrogen atmosphere. The reaction mixture was allowed to warm to room temperature and the progress monitored by TLC (95% CHCl$_3$/MeOH). After 2 hours 15 minutes TLC revealed the reaction was complete, proceeding via the presumed half-imine product, to give a TLC spot which fluoresced brightly under UV. The solvent was evaporated in vacuo and the resulting residue subjected to flash chromatography (98% CHCl$_3$/MeOH) to give the bis-imine target molecule 39 (SJG-136) as a pale orange glass (78 mg, 77%) which was repeatedly evaporated in vacuo with CHCl$_3$ to provide the imine form: [α]$^{21}_D$=+357.7° (c=0.07, CHCl$_3$); Reverse Phase HPLC (C$_4$ stationary phase, 65% MeOH/H$_2$O mobile phase, 254 nm), Retention time=6.27 minutes, % Peak area=97.5%; $^1$H NMR (270 MHz, CDCl$_3$) (imine form) δ 7.68 (d, 2H, J=4.4 Hz, HC=N), 7.49 (s, 2H$_{arom}$), 6.85 (s, 2H$_{arom}$), 5.20 (s, 2H, NCH$_2$C=CH$_2$), 5.17 (s, 2H, NCH$_2$C=CH$_2$), 4.46-4.19 (m, 4H, OCH$_2$CH$_2$CH$_2$O), 3.92 (s, 6H, OCH$_3$), 3.89-3.68 (m, 6H, NCH$_2$C=CH$_2$ and NCHHC=N), 3.12 (dd, 2H, J=8.61, 16.21 Hz, NCH$_2$C=CH$_2$CH$_2$), 2.68 (d, 2H, J=16.30 Hz, NCH$_2$C=CH$_2$CH$_2$), 2.45-2.38 (m, 2H, OCH$_2$CH$_2$CH$_2$O); $^{13}$C NMR (67.8 MHz, CDCl$_3$) (imine form) δ 164.7 (NC=O), 162.6 (HC=N), 150.7 (C$_{quat}$), 147.9 (C$_{quat}$), 141.5 (C$_{quat}$), 140.6 (C$_{quat}$), 119.8 (C$_{quat}$), 111.5 (C—H$_{arom}$), 110.7 (C—H$_{arom}$), 109.4 (NCH$_2$C=CH$_2$), 65.4 (OCH$_2$CH$_2$CH$_2$O), 56.1 (OCH$_3$), 53.8 (NCHHC=N), 51.4 (NCH$_2$C=CH$_2$), 35.4 (NCH$_2$C=CH$_2$CH$_2$), 28.8 (OCH$_2$CH$_2$CH$_2$O); MS (FAB) (Relative Intensity) (imine form) 773 (M$^+$+1+(Thioglycerol adduct×2), 3), 665 (M$^+$+1+Thioglycerol adduct, 7), 557 (M$^+$+1, 9), 464 (3), 279 (12), 257 (5), 201 (5), 185 (43), 166 (6), 149 (12), 93 (100); IR (NUJOL$^7$) 3600-3100 (br, OH of carbinolamine form), 2923, 2849, 1599, 1511, 1458, 1435, 1391, 1277, 1228, 1054, 1011, 870, 804, 761, 739 cm$^{-1}$.

Figure 5A:
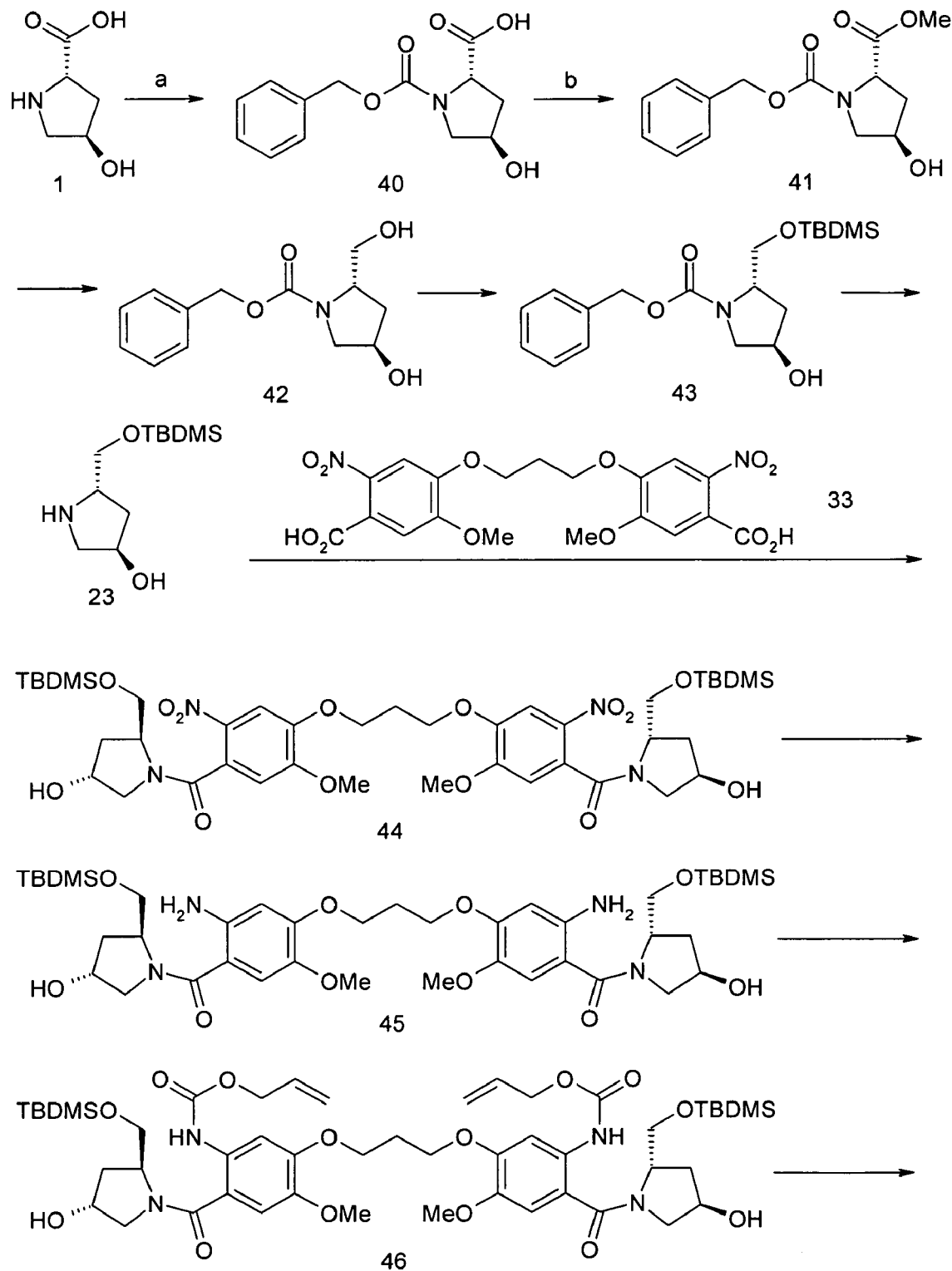
Figure 5B:
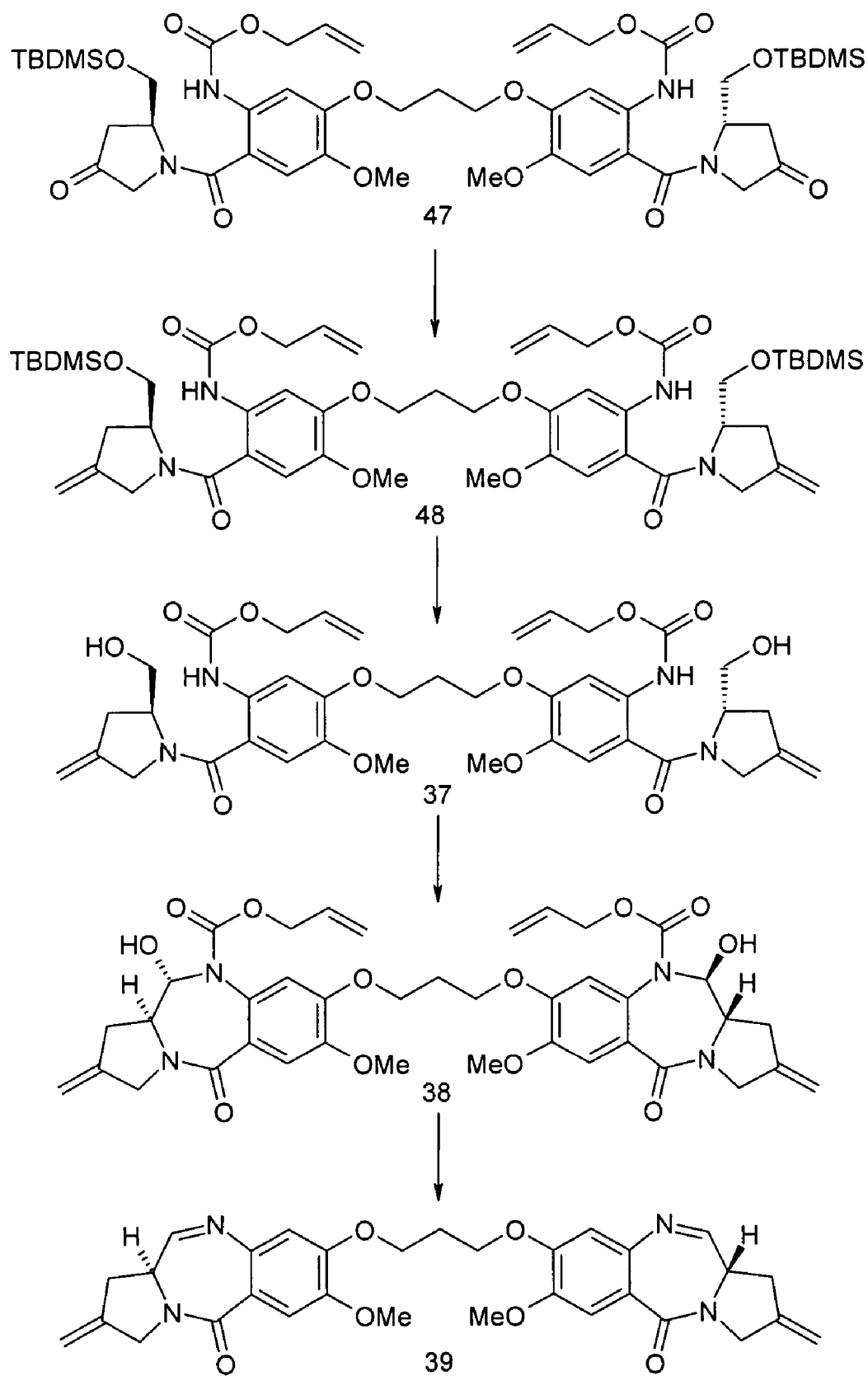

Alternative Synthesis of UP2001, SJG-136 (39) (see FIG. 5a/5b)

UP2001 was also prepared by an alternative synthesis based the bis ketone 47.

(2S,4R)-N-(Benzoxycarbonyl)-2-carboxy-4-hydroxypyrrolidine (40)

A solution of benzyl chloroformate (12.5 mL, 87.7 mL) in toluene (40 mL) was added to a solution of trans-4-hydroxy-L-proline 1 (10 g, 76.3 mmol) and NaHCO$_3$ (16 g, 190 mmol) in H$_2$O (165 mL) over a period of 15 minutes. After stirring at room temperature for 12 hours the two phases were allowed to separate. The aqueous phase was washed with diethyl ether (4×50 mL), cooled in an ice bath, and then acidified to pH 2 with conc. HCl. The resultant product was extracted with ethyl acetate (5×50 mL) and the combined organic extracts were dried (MgSO$_4$) and the excess solvent evaporated in vacuo to afford a colourless viscous oil (20.30 g, 100%). [α]$^{27}_D$=-565° (c=0.1, MeOH). $^1$H NMR (CDCl$_3$): δ 2.07-2.31 (m, 3H, H1), 3.52-3.59 (m, 2H, H3), 4.43-4.53 (m, 2H, H2,H11a), 5.8 and 5.11 (s, 2H, minor and major rotamers of H6, 1:2), 6.0 (bs, 2H, OH), 7.26-7.29 and 7.32-7.34 (m, 5H, minor and major rotamers of H arom, 1:2). IR (thin film): ν=3414 (OH), 2940 (OH), 1682 (C=O), 1495, 1429, 1359 (CO2-), 1314, 1269, 1205, 1180, 1174, 1127, 1082, 1051, 993, 914, 866, 826, 769, 741, 697 cm−1. MS (EI): m/e (relative intensity): 266 (M+, 1), 265 (6), 220 (5), 176 (15), 130 (34), 108 (2), 91 (100), 86 (4), 68 (11). HRMS calcd. for C$_{13}$H$_{15}$NO$_5$=265.0950 found 265.0976.

(2S,4R)-N-(Benzoxycarbonyl)-2-methyoxycarbonyl-4-hydroxyproline (41)

A solution of (2S,4R)-N-(benzoxycarbonyl)-2-carboxy-4-hydroxypyrrolidine (40) (20.30 g, 76.3 mmol) in dry methanol (300 mL) was heated at reflux for 18 hours in the presence of a catalytic amount of conc. $H_2SO_4$ (2.20 mL, 7.63 mmol). The reaction mixture was allowed to cool to room temperature and neutralised with $Et_3N$ (3.0 mL, 76.3 mmol). The reaction mixture was concentrated in vacuo and the residue redissolved in ethyl acetate (200 mL), washed with brine (1×50 mL), dried ($MgSO_4$) and excess solvent removed under reduced pressure to afford a colourless gum (41,17 g, 99%). $[\alpha]^{20}_D = -59.4°$ (c 0.014, $CHCl_3$). $^1H$ NMR ($CDCl_3$): δ 2.04-2.08 and 2.24-2.35(m, 1H, rotamers of H1, 1:1), 2.64 (bs, 1H, OH), 3.54 and 3.74 (s, 3H, rotamers of OMe, 1:1), 3.66-3.69 (m, 2H, H3), 4.47-4.50 (m, 2H, H2,H11a), 5.07-5.13 (m, 2H, H6), 7.26-7.35 (m, 5H, H arom). $^{13}C$ NMR ($CDCl_3$): rotamer ratio 1:1, δ 37.8 and 38.5 rotamers of (C1), 51.8 and 52.0 rotamers of (OMe), 54.1 and 54.7 rotamers of (C3), 57.4 and 57.7 rotamers of (C2), 66.9 and 67.0 rotamers of (C6), 68.6 and 69.3 rotamers of (C11a), 127.0, 127.3, 127.4, 127.7, 127.8, 128.0 and 128.1 rotamers of (C arom). IR (thin film): v=3435 (OH), 3033, 2953 (OH), 1750 (ester), 1680 (C=O), 1586, 1542, 1498, 1422, 1357 (CO2H), 1170, 1124,1084, 1052 (C—O), 1004, 963, 916, 823, 770, 750, 699, 673 cm−1. MS (FAB) m/z (relative intensity): 280 (M+., 24), 236 (20), 234 (4), 216 (8), 214 (4), 213 (2), 206 (2), 204 (7), 203 (4), 202 (10), 201 (2), 181 (5), 144 (16), 102 (23), 91 (100). HRMS calcd. for $C_{14}H_{17}NO_5 = 279.1107$. found 279.1192.

(2S,4R)-N-(Benzoxycarbonyl)-2-hydroxymethyl-4-hydroxyproline (42)

Lithium borohydride (1.57 g, 73 mmol) was added portionwise to a solution of (2S,4R)-N-(benzoxycarbonyl)-2-methyoxycarbonyl-4-hydroxyproline (41) (20.17 g, 73 mmol) in THF (350 mL) at 0° C. The reaction mixture was allowed to warm to room temperature and stir overnight. The resulting suspension was cooled to 0° C. and quenched with water (2-3 mL) until effervescence ceased, at which point 2 M HCl (15 mL) was added to dissolve the precipitate. The product was extracted with ethyl acetate (3×150 mL) and the combined organic phases washed with brine (1×100 mL) and then dried ($MgSO_4$). Concentration in vacuo afforded a white gum (18.25 g, 100%). $[\alpha]^{22.3}_D = -404°$ (C=0.043, $CHCl_3$). 1H NMR ($CDCl_3$): δ 1.24-1.26 (m, 1H, H1), 1.73-2.08 (m, 1H, H1), 3.40-4.30 (m, 6H, H2,H3,H11,H11a), 5.06 (bs, 1H, OH), 5.09 (s, 2H, H6) 7.25-7.31 (m, 5H, H arom). 13C NMR ($CDCl_3$): δ 36.7 (C1), 55.2 (C3), 58.7 (C2), 65.0 (C11), 67.0 (C6), 68.7 (C11a), 127.0 127.5 (C arom), 127.8 (C arom), 128.2 (C arom). IR (thin film): v=3390 (OH), 3065, 3033, 2953 (OH), 1681 (C=O carbamate), 1586, 1538, 1498, 1454, 1192, 1122, 978, 914, 862, 770, 698, 673 cm−1. MS (FAB) m/z (relative intensity): 252 (M+, 58), 208 (33), 176 (5), 144 (6), 118 (8), 116 (7), 92 (13), 91 (100). HRMS calcd. for $C_{13}H_{17}NO_4 = 251.1158$. found 251.1230.

(2S,4R)-N-Benzoxycarbonyl-2-t-butyidimethylsilyloxymethyl-4-hydroxypyrrolidine (43)

t-butyldimethylsilyl chloride (5.78 g, 38.3 mmol) and 1,8-diazabicyclo[5,4,0]undec-7-ene (1.44 mL, 9.6 mmol) were added to a solution of alcohol (42) (12.51 g, 49.8 mmol) and triethylamine (7.0 mL, 49.8 mmol) in dry DCM (200 mL) which had been allowed to stir for 15 minutes at room temperature. The resulting mixture was allowed to stir at room temperature for 18 hours and then diluted with ethyl acetate (300 mL). The organic phase was washed with aqueous saturated ammonium chloride (2×100 mL) and brine (1×100 mL) dried ($MgSO_4$) and the solvent removed under reduced pressure to yield a colourless viscous oil (9.84 g, 70%). $[\alpha]^{22.3}_{D=-263}°$ (c 0.70, $CHCl_3$). $^1H$ NMR ($CDCl_3$): δ −0.05 and −0.06(s, 6H, rotamers of H1=, H2=, 1:1), 0.83 and 0.85 (s, 9H, rotamers of H3=, H5=, H6=, 1:1), 1.95-2.22 (m, 2H, H1,), 2.78 (bs, 1H, OH), 3.44-3.68 (m, 3H, H3,H11), 3.99-4.10 (m, 1H, H2), 4.43-4.46 (m, 1H, H11a), 5.11-5.16 (m, 2H, H6) 7.34-7.35 (m, 5H, H arom) $^{13}C$ NMR ($CDCl_3$): rotamer ratio of 1:1, δ −5.50 (C3=, C5=, C6=), 18.15 (C4=), 25.83 (C1=, C2=), 36.55 and 37.27 rotamers of (C1), 55.2 and 55.7 rotamers of (C3), 57.3 and 57.8 rotamers of (C2), 62.8 and 63.9 rotamers of (C11), 66.6 and 67.0 rotamers of (C6), 69.7 and 70.3 rotamers of (C11a), 127.8 (C arom), 127.9 (C arom), 128.0 (C arom), 128.4 (C arom), 128.5 (C arom), 136.5 and 136.8 rotamers of (C7), 154.9 and 155.2 rotamers of (C5). IR (thin film): v=3415 (OH), 3066, 3034, 2953 (OH), 2930, 2884, 2857, 1703 (C=O carbamate), 1587, 1498, 1424, 1360 (C—CH3), 1288 (CH3Si), 1255 (t-Bu), 1220, 1195 (t-Bu), 1118 (Si—O), 1057, 1003, 917, 836, 774, 751, 698, 670 cm−1. MS (El/Cl) m/e (relative intensity): 366 (M+., 100), 308 (14), 258 (2), 91 (2).

(2S,4R)-2-t-butyldimethylsilyloxymethyl-4-hydroxypyrrolidine (23)

A slurry of 10% Pd/C (190 mg) in ethyl acetate (20 mL) was added to a solution of TBDMS ether (43) (1.90 g, 5.19 mmol) in ethanol (100 mL). The reaction mixture was hydrogenated (Parr apparatus) for 16 h. The catalyst was removed by vacuum filtration through Celite and excess solvent was evaporated under reduced pressure to give a yellow oil in quantitative yield (1.20 g, 100%). $[\alpha]^{22.2}_D = +35.6°$ (c 0.042,CHCl3). 1H NMR ($CDCl_3$): δ −(0.07-0.08) (m, 6H, H1=, H2=), 0.82 (s, 9H, H3=, H4=, H5=), 1.68-1.73 (m, 2H, H1,), 2.99-3.11 (m, 2H, H11), 3.47-3.50 (m, 3H, H11a, H3), 4.09 (bs, 1H, NH or OH), 4.32 (bs, 1H, NH or OH). 13C NMR ($CDCl_3$): δ −5.4 (C3=, C5=, C6=), 18.1 (C4=), 25.8 (C1=, C2=), 37.4 (C1), 54.6 (C11), 58.1 (C2), 64.6 (C3), 72.2 (C11a). IR (thin film): v=3330 (OH), 2928, 2857, 1557, 1421, 1331 (C—CH3), 1249 (CH3-Si), 1204 (t-Bu), 1191 (t-Bu), 1100 (Si—O), 1073, 993, 713 cm−1. MS (Cl) m/e (relative intensity): 232 (M+., 100), 230 (13), 174 (5), 133 (6), 86 (6).

1,1=-[[(Propane-1,3-diyl)dioxy]bis[2-nitro-5-methoxy-1,4-phenylene)carbonyl]]-bis[(2S,4R)-2-t-butyidimethylsilyloxymethyl-4-hydroxypyrrolidine (44)

A catalytic amount of DMF (2 drops) was added to a stirred suspension of bis-nitroacid (33) (2.00 g, 4.28 mmol) and oxalyl chloride (0.94 mL, 10.70 mmol) in dry THF (20 mL), and the reaction mixture was allowed to stir for 4 h. After evaporation of excess THF in vacuo, the resultant yellow residue was dissolved in dry THF (20 mL) and added dropwise over a period of 25 minutes to a vigorously stirred suspension of amine (23) (2.47 g, 10.70 mmol), $Et_3N$ (2.50 mL, 17.9 mmol) and ice/water (0.6 mL) cooled in an ice bath. The mixture was then allowed to warm to room temperature for a further 1.5 h. After removal of the THF by evaporation in vacuo, the residue was diluted with water (100 mL) and extracted with ethyl acetate (3×100 mL). The combined organic phase was washed with water (3×25 mL)

and brine (3×25 mL), dried (MgSO4), and the solvent removed in vacuo to afford a yellow oil which was purified by flash chromatography (3% MeOH/CHCl3) to afford the bis-amide (44) as a yellow solid (2.05 g, 54%). $[\alpha]^{23.8}_D= -993°$ (c 0.033, CHCl3). $^1$H NMR (CDCl3): δ −0.05 (s, 12H, H1=, H2=), 0.80 (s, 18H, H3=, H5=, H6=), 1.96-1.99 (m, 2H, H1), 2.14-2.16(m, 2H, H1), 2.19-2.24 (m, 2H, H13), 2.85-2.89 (m, 2H, H2) 3.16-3.19 (m, 4H, H11), 3.63-3.66 (m, 4H, H3), 3.81 (s, 6H, OMe), 3.99-4.10 (m, 2H, H3), 4.23 (t, 4H, J=5.3 Hz, H12), 4.38 (bs, 2H, OH); 5.20-5.25 (m, 2H, H11a), 6.65 (s, 2H, H6), 7.55 (s, 2H, H9). $^{13}$C-NMR (CDCl3): δ −5.35 (C1=, C2=), 18.2 (C4=), 25.8 (C3=, C5=, C6=), 28.9 (C13), 36.1 (Cl), 54.9 (CH3O), 56.6 (C4), 57.3 (C12), 65.0 (C3), 70.0 (C2), 108.0 (C6), 109.4 (C9), 128.2 (Q), 137.2 (Q), 148.1 (Q), 148.5 (Q), 154.5 (Q), 166.5 (Q). IR (thin film): v=3392 (OH), 2950, 2856, 1623 (C=O), 1577 (C arom), 1524 (NO2), 1459, 1432, 1381, 1338 (C-CH3), 1278 (CH3-Si), 1219 (t-Bu), 1184 (t-Bu), 1075 1053, 1004, 938, 914, 837, 778, 724, 668, 649, cm−1. MS (FAB) m/z (relative intensity): 894 (M+, 8), 893 (19), 878 (6), 835 (2), 779 (9), 761 (6), 517 (3), 459 (5), 258 (7), 100 (3), 86 (4), 75 (29), 73 (100), 59 (17), 58 (6).

1,1=-[[(Propane-1,3-diyl)dioxy]bis[2-amino-5-methoxy-1,4-phenylene)carbonyl]]-bis[(2S,4R)-2-t-butyidimethylsilyloxymethyl-4-hydroxypyrrolidine (45)

A slurry of 10% Pd/C (155 mg) in ethyl acetate (20 mL) was added to a solution of the bis-amide (44) (1.55 g, 1.73 mmol) in ethanol (100 mL). The reaction mixture was hydrogenated (Parr apparatus) for 16 h. The reaction mixture was filtered through Celite and the solvent was removed under reduced pressure to give a yellow oil (45) in quantitative yield (1.44 g, 100%). $^1$H NMR (CDCl3): δ 0.00 (s, 12H, H1=, H2=), 0.88 (s, 18H, H3=, H5=, H6=), 2.00-2.25 (m, 6H, H1,H13), 3.50-3.72 (m, 12H, H2,H3,H11,H11a), 3.74 (s, 6H, OMe), 4.16-4.20 (m, 4H, H3), 4.30-4.35 (m, 4H, H12), 4.49 (bs, 2H, OH); 6.23 (s, 2H, H9), 6.64 (s, 2H, H6) $^{13}$C-NMR (CDCl3): δ −5.5 (C1=, C2=), 18.1 (C4=), 25.8 (C3=, C5=, C6=), 29.6 (C13), 35.2 (C1), 56.7 (CH3O), 62.2 (C4), 64.1 (C3), 70.0 (C2), 102.2 (C9), 112.6 (C6), 140.4 (Q), 141.1 (Q), 150.6 (Q), 170.1 (Q); IR (neat): v=3359 (OH), 2929, 2856, 1621 (C=O), 1591 (C arom), 1469, 1433, 1406, 1358, 1346 (C—CH3), 1261 (CH3-Si), 1232 (t-Bu), 1175 (t-Bu), 1117, 1056, 1006, 866, 835, 776 cm−1. MS (FAB) m/z (relative intensity): 834 (M+., 13), 833 (18), 773 (9), 602 (13), 399 (7), 371 (34), 206 (22), 192 (14), 176 (13), 166 (44), 150 (8), 100 (10), 73 (100).

1,1=-[[(Propane-1,3-diyl)dioxy]bis[2-amino-N-allyloxycarbonyl-5-methoxy-1,4-phenyl-ene)-carbonyl]]-bis [(2S,4R)-2-t-butyidimethylsilyloxymethyl-4-hydroxy-pyrrolidine (46)

A solution of the bis-amide (45) (2.76 g, 3.31 mmol) and pyridine (1.10 mL, 13.60 mmol) in dried DCM (100 mL) was cooled to 0° C. Allyl chloroformate (0.80 mL, 7.53 mmol) in DCM (50 mL) was added dropwise and the resulting mixture allowed to warm to room temperature and stirred for 16 h. The reaction mixture was diluted with DCM (200 mL) and washed with 1 M CuSO4 (3×50 mL), water (1×50 mL) and brine (1×50 mL) before drying (MgSO4). Evaporation of the solvent under reduced pressure followed by flash column chromatography (2.5% MeOH/DCM) afforded (46) as a yellow solid (3.24 g, 97%). $[\alpha]^{20.1}_D= -571°$ (c 0.007, CHCl3). $^1$H NMR (CDCl3): δ 0.00 (s, 12H, H1=, H2=), 0.89 (s, 18H, H3=, H5=, H6=), 2.03-2.36 (m, 6H, Hi, H13), 3.51-3.58 (m, 6H, H2,H3), 3.77 (s, 6H, OMe), 4.20-4.26 (m, 8H, H11,H12), 4.28-4.30 (m, 2H, H11a), 4.56-4.60 (m, 6H, H8=, OH), 5.25 (dd, J1,2=1.5 Hz, J1,3=15.0 Hz, 4H, H10=), 5.90-5.95 (m, 2H, H9=), 6.73 (s, 2H, H6), 7.63 (s, 2H, H9), 8.80 (s, 2H, NH). $^{13}$C NMR (CDCl3): δ −5.42 (C1=, C2=), 25.8 (C3=, C5=, C6=), 29.2 (C13), 35.4 (C1), 56.3 (CH3O), 57.1 (C11a), 59.8 (C11), 62.2 (C3), 65.1 (C12), 65.7 (C8=), 70.5 (C2), 106.3 (C9), 111.5 (C6), 116.5 (Q), 118.1 (C10=), 131.7 (Q), 132.5 (C9=), 144.3 (Q), 150.3 (Q), 153.8 (Q), 169.5 (Q). IR (neat): v=3351 (OH), 2931, 2857, 1762 (Alloc C=O), 1722, 1603 (C=O), 1521 (C arom), 1463, 1404, 1264 (CH3-Si), 1222 (t-Bu), 1106 (t-Bu), 1053, 1015, 936, 872, 837, 775,629, cm−1.

1,1=-[[(Propane-1,3-diyl)dioxy]bis[2-amino-N-allyloxycarbonyl-5-methoxy-1,4-phenylene)-carbonyl]]-bis[(2S)-2-t-butyidimethylsilyloxymethyl-4-oxopyrrolidine (47)

A solution of dimethyl sulphoxide (2.10 mL, 28.5 mmol) in dry DCM (20 mL) was added dropwise over a 15 minutes period to a stirred, cooled (−45° C.) solution of oxalyl chloride (1.27 mL, 14.60 mmol) in DCM (30 mL). After 35 minutes, a solution of alcohol (46) (2.54 g, 2.53 mmol) in DCM (20 mL) was added dropwise over a period of 15 minutes to the reaction mixture at −45° C. After 45 minutes a solution of triethylamine (5.75 mL, 40.3 mmol) in DCM (20 mL) was added over a period of 15 minutes and the reaction mixture stirred at −45° C. for 30 minutes before warming to room temperature over 45 minutes. The mixture was then washed with 1 M CUSO4 (3×50 mL), water (2×50 mL) and brine (1×50 mL) before drying (MgSO4) and concentrating in vacuo to give (47) as a yellow solid (2.46 g, 97%). $^1$H NMR (CDCl3): δ 0.00 (s, 12H, H1=, H2=), 0.86 (s, 18H, H3=, H5=, H6=), 2.50 -2.63 (m, 6H, H1, H13), 3.63-3.70 (m, 4H, H3), 3.80 (s, 6H, OMe), 3.93-3.97 (m, 6H, H11,H11a), 4.29-4.32 (m, 4H, H12), 4.62 (d, 4H, J=5.7 Hz, H8=), 5.27-5.32 (m, 4H, H10=), 5.98-6.03 (m, 2H, H9=), 6.74 (s, 2H, H6), 7.74 (s, 2H, H9), 8.80 (s, 2H, NH). $^{13}$C NMR (CDCl3): δ −5.76 (C1=, C2=), 18.0 (C4=), 25.7 (C3=, C5=, C6=), 28.8 (C13), 39.6 (C1), 55.0 (C3), 56.4 (CH30), 65.3 (C12), 65.8 (C8=), 105.9 (C9), 110.7 (C6), 118.2 (C10=), 132.4 (C9=), 150.7 (Q), 153.5 (Q), 169.1 (Q), 210.0 (C2). IR (neat): v=3308 (OH), 2931, 2856, 1765 (Alloc C=O), 1730, 1624 (C=O), 1602 (C=O), 1522 (C arom), 1468, 1407, 1332, 1259 (CH3-Si), 1204 (t-Bu), 1105 (t-Bu), 1053, 1010, 937, 870, 837, 808, 778, 674, 657 cm−1.

1,1=-[[(Propane-1,3-diyl)dioxy]bis[2-amino-N-allyloxycarbonyl-5-methoxy-1,4-phenylene)carbonyl]]-bis[(2S)-2-t-butyidimethylsilyloxymethyl-4-methylidene-2,3-dihydropyrrole] (48)

A solution of potassium-t-butoxide in dry THF (0.5 M, 4.00 mL, 2.00 mmol) was added to as suspension of methyltriphenylphosphonium bromide (0.716 g, 2.00 mmol) in dry THF (2.00 mL). The resulting yellow ylide suspension was allowed to stir at 0° C. for 2 hours before the addition of a solution of the bis-ketone 47 (0.50 g, 0.50 mmol) in THF (10 mL) at 10° C. The reaction mixture was allowed to warm to room temperature and stirring was continued for a further hour. The reaction mixture was partitioned between ethyl acetate (15 mL) and water (15 mL) and the organic layer was washed the sat. sodium chloride (20 mL) and dried over magnesium sulphate. Removal of excess solvent gave a brown oil that was subjected to flash column chromatography (50% ethyl acetate, 50% 40-60° petroleum ether) to afford the product as a yellow glass 48 (250 mg, 51%). [α]$^{23.4}_D$=−32° (c 0.265, CHCl$_3$). $^1$H NMR (CDCl$_3$): δ 0.00 (s, 12H), 0.88 (s, 18H), 2.37-2.40 (m, 2H), 2.69-2.75 (m, 4H), 3.80-4.62 (m, 20H), 4.61-4.63 (m, 4H), 4.98 (bs, 4H), 5.30-5.38 (m, 4H), 5.94-6.00 (m, 2H), 6.81 (s, 2H), 7.84 (s, 2H), 8.80 (bs, 2H).

1,1=-[[(Propane-1,3-diyl)dioxy]bis[2-amino-N-allyloxycarbonyl-5-methoxy-1,4-phenylene)carbonyl]]-bis[(2S)-2-hydroxymethyl-4-methylidene-2,3-dihydropyrrole] (37)

An aliquot of hydrogen fluoride/pyridine complex (0.8 mL, 70% HF, 30% pyridine) was added to a solution of the bis-silyl ether 48 (285 mg, 0.287 mmol) in THF (10 mL) at 0° C. under a nitrogen atmosphere. Stirring was continued at 0° C. for 30 minutes and the reaction mixture was then allowed to rise to room temperature over a 1 hour period. The reaction mixture was neutralised with sodium bicarbonate and extracted with dichloromethane (3×30 mL). The combined organic phase was washed with brine and dried over magnesium sulphate. Removal of excess solvent under reduced pressure afforded the product 37 as a yellow gum (218 mg).

1,1=[[(Propane-1,3-diyl)dioxy]bis(11S,11aS)-10-(allyloxycarbonyl)-11-hydroxy-7-methoxy-2-methylidene-1,2,3,10,11,11a-hexahydro-5H-pyrrolo[2,1-c][1,4-benzodiazepin-5-one] (38)

A solution of dimethyl sulphoxide (0.55 mL, 7.75 mmol) in dry dichloromethane (10 mL) was added dropwise, over a 15 minute period, to a stirred solution of oxalyl chloride (0.32 mL, 3.67 mmol) in dichloromethane (10 mL) at −45° C. under a nitrogen atmosphere. The reaction mixture was allowed to stir for 35 minutes at −45° C. followed by addition of the diol 37 (1.01 g, 1.32 mmol) in dichloromethane (10 mL), at the same temperature, over 15 minutes. After a further 45 minutes a solution of triethylamine (1.50 mL, 10.76 mmol) in dichloromethane (10 mL) was added over a period of 15 minutes. The reaction mixture was allowed to stir at −45° C. for 30 minutes before being allowed to warm to room temperature over 45 minutes. The reaction mixture was diluted with water and the phases were allowed to separate. The organic phase was washed with 1M HCl (3×50 mL), sat. sodium chloride (50 mL) and dried over magnesium sulphate. Removal of excess solvent yielded the crude product, which was purified by flash column chromatography (1.5% methanol, 98.5% chloroform) to afford the product 38 (0.785 g, 77%).

1,1=[[(propane-1,3-diyl)dioxy]bis[(11aS)-7-methoxy-2-methylidene-1,2,3,11a-tetrahydro-5H-pyrrolo[2,1-c][1,4]benzodiazein-5-one] (39, SJG-136)

A catalytic amount of tetrakis(triphenylphosphine)palladium (21 mg, 0.018 mmol) was added to a stirred solution of the bis-alloc-carbinolamine 38 (250 mg, 0.33 mmol), triphenylphosphine (10 mg, 0.033 mmol) and pyrrolidine (0.05 mL, 0.66 mmol) in dry CH$_2$Cl$_2$ (30 mL) at 0° C. (ice/acetone) under a nitrogen atmosphere. The reaction mixture was allowed to stir for 2 hours before warming to room temperature over 1 hour. The solvent was evaporated under reduced pressure and the resulting residue subjected to flash chromatography (98% CHCl$_3$/MeOH) to give the bis-imine target molecule 39 (SJG-136).

Example 1(e)

Figure 6A:
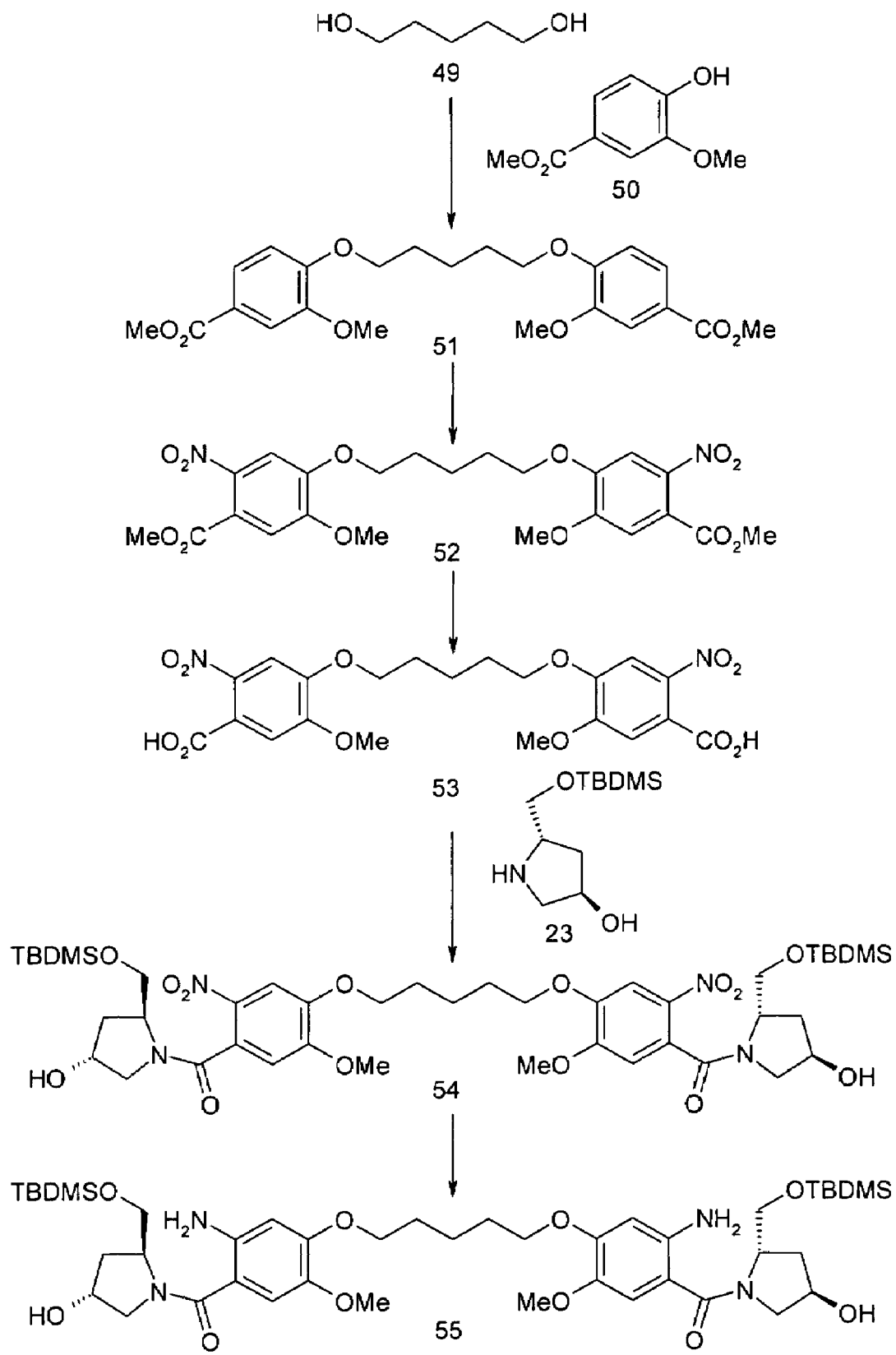
Figure 6B:
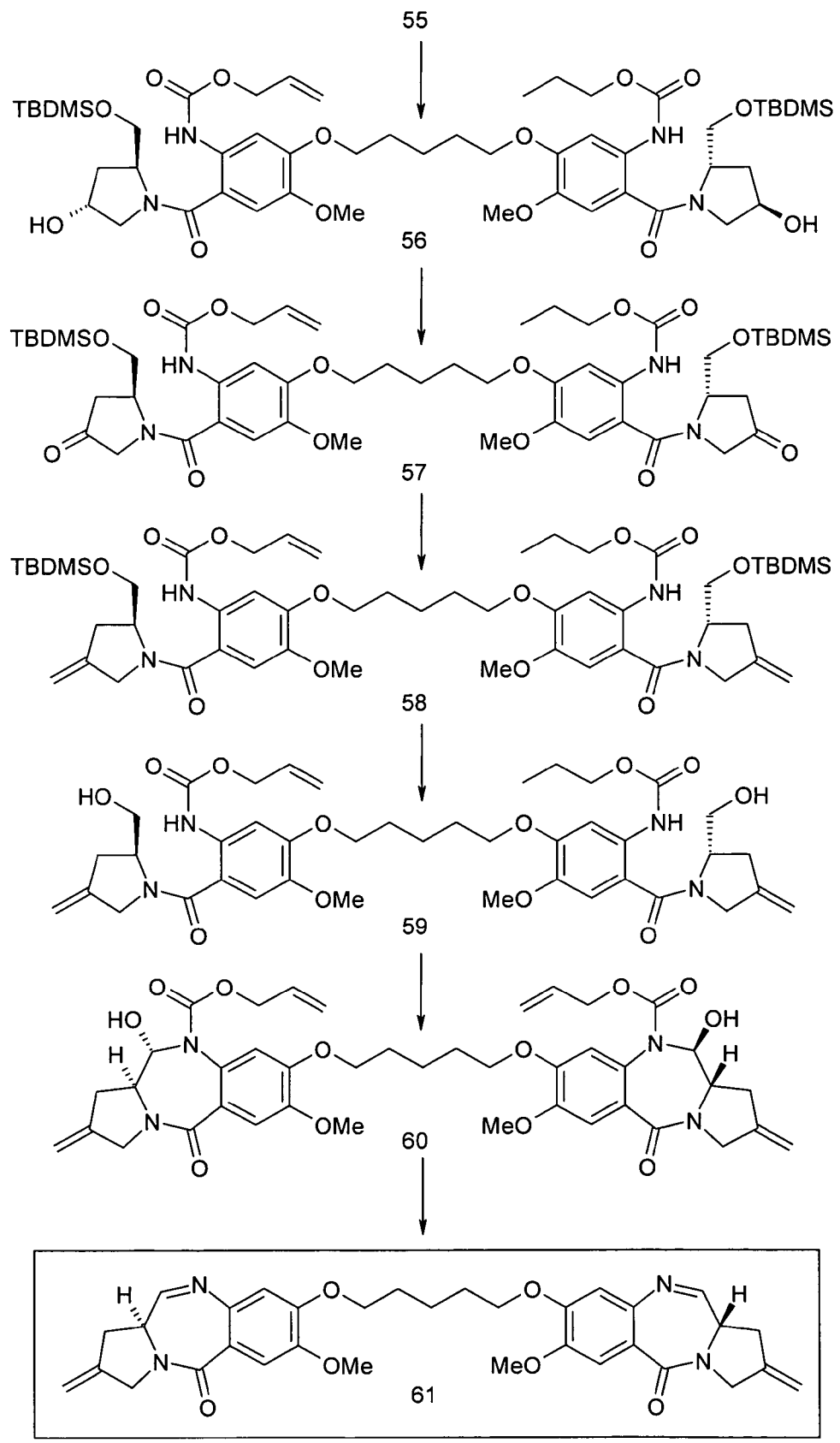

Synthesis of 1.1=[[(pentane-1,5-diyl)dioxy]bis[(11aS)-7-methoxy-2-methylidene-1,2,3,11a-tetrahydro-5H-pyrrolo[2,1-c][1,4]benzodiazepin-5-one] (61) (see FIGS. 6a/b)

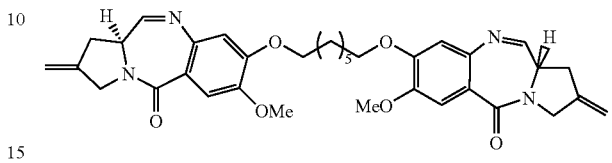

Preparation of Nitro Dimer Core

1=,5=-Bis[2-methoxy-4-(methoxycarbonyl)phenoxy]pentane (51) Neat diethyl azidodicarboxylate (19.02 mL, 21.04 g, 120.8 mmol) was added dropwise over 30 minutes to a stirred solution of methyl vanillate (50) (20 g, 109.8 mmol) and triphenylphosphine (43.2 g, 164.7 mmol) in anhydrous THF (400 mL) and the reaction mixture was allowed to stir at 0° C. for 1 h. The cold reaction mixture was treated dropwise over 20 minutes with a solution of 1,5-pentanediol (49) (3.83 mL, 4.03 g, 53.0 mmol) in THF (4 mL). The reaction mixture was allowed to stir overnight at room temperature and the precipitated product (51) was collected by vacuum filtration. Dilution of the filtrate with methanol precipitated further product (51). The combined precipitate (12.3 g, 52% based on pentanediol) was used in the next step without further purification: $^1$H NMR (270 MHz, CDCl$_3$) δ 7.65 (dd, 2H, J=2.01, 8.42 Hz), 7.54 (d, 2H, J=2.01 Hz), 6.87 (d, 2H, J=8.42 Hz), 4.10 (t, 4H, J=6.59 Hz), 3.90 (s, 6H), 3.89 (s, 6H), 2.10-1.90 (m, 4H), 1.85-1.26 (m, 2H).

1=,5=-Bis[2-methoxy-4-(methoxycarbonyl)-5-nitrophenoxy]pentane (52)

Solid copper (II) nitrate trihydrate (16.79 g, 69.5 mmol) was added slowly to a stirred solution of the bis-ester (51) (12 g, 27.8 mmol) in acetic anhydride (73 mL) at 0° C. The reaction mixture was allowed to stir for 1 hour at 0° C., the ice bath was removed and the reaction mixture was allowed to warm to room temperature a mild exotherm, c. 40° C., accompanied by the evolution of NO$_2$ occurred at this stage. After the exotherm had subsided stirring at room temperature was continued for 2 hours. The reaction mixture was poured into ice water and the aqueous suspension allowed to stir for 1 h. The resulting yellow precipitate was collected by vacuum filtration and dried in air to afford the desired bis nitro compound (52) (14.23 g, 98%): $^1$H NMR (400 MHz, CDCl$_3$+DMSO) δ 7.45 (s, 2H), 7.09 (s, 2H), 4.14 (t, 4H, J=6.31 Hz), 3.97 (s, 6H), 3.90 (s, 6H), 2.20-1.94 (m, 4H), 1.75-1.70 (m, 2H).

1=,5=-Bis(4-carboxy-2-methoxy-5-nitrophenoxy)pentane (53)

A suspension of the ester 52 (9.0 g, 17.2 mmol) in aqueous sodium hydroxide (1 M, 180 mL) and THF (180 mL) was allowed to stir until a homogenous solution was obtained (2 days). THF was evaporated under reduced pressure and the resulting aqueous suspension was filtered to remove any unreacted starting material. The filtrate was adjusted to pH 1, the precipitated product was collected by filtration and air dried to afford the desired bis-acid (53) (8.88 g). A higher than theoretical yield was obtained due to the inclusion of the sodium salt of acid. The salt may be removed by dissolving the bulk of the material in THF and removing the insoluble material by filtration: $^1$H NMR (400 MHz, CDCl$_3$) δ 7.39 (s, 2H), 7.16 (s, 2H), 4.12 (t, 4H, J=6.59 Hz), 3.95 (s, 6H), 2.00-1.85 (m, 4H), 1.75-1.67 (m, 2H).

Assembling the Bis Ketone Intermediate 1,1=-[[(Pentane-1,5-diyl)dioxy]bis[2-nitro-5-methoxy-1,4-phenylene)carbonyl]]-bis[(2S,4R)-2-t-butyidimethylsilyloxymethyl-4-hydroxypyrrolidine] (54)

A catalytic amount of DMF (5 drops) was added to as stirred suspension of the acid 53 (5.39 g, 10.9 mmol) and oxalyl chloride (3.47 g, 2.38 mL, 27.3 mmol) in anhydrous THF (50 mL). Initial effervescence was observed followed by the formation of a homogenous solution, however after stirring overnight a suspension of the newly formed acid chloride was formed. Excess THF and oxalyl chloride was removed by rotary evaporation under reduced pressure and the acid chloride was resuspended in fresh THF (49 mL). The acid chloride solution was added dropwise to a solution of the (2S, 4R)-2-t-butyidimethylsilyloxymethyl-4-hydroxypyrrolidine (23) (6.3 g, 27.3 mmol), triethylamine (4.42 g, 6.09 mL, 43.7 mmol) and water (1.47 mL) in THF (33 mL) at 0° C. under a nitrogen atmosphere. The reaction mixture was allowed to warm to room temperature and stirring was continued for 3 h. Excess THF was removed by rotary evaporation under reduced pressure and the resulting residue was partitioned between water (300 mL) and ethyl acetate (300 mL). The layers were allowed to separate and the aqueous layer was extracted with ethyl acetate (3×150 mL). The combined organic layers were then washed with ammonium chloride (150 mL), sat. sodium bicarbonate (150 mL), brine (150 mL) and dried over magnesium sulphate. Filtration followed by rotary evaporation under reduced pressure afforded the crude product as a dark oil. The crude product was subjected to flash column chromatography (3% methanol, 97% chloroform) and removal of excess eluent isolated (54) (3.70 g, 37% yield): $^1$H NMR (270 MHz, CDCl$_3$) δ 7.65 (s, 2H), 6.77 (s, 2H), 4.52 (bs, 2H), 4.40 (bs, 2H), 4.17-4.10 (m, 6H), 3.92 (s, 6H), 3.77 (d, 2H, J=10.26 Hz), 3.32 (td, 2H, J=4.40, 11.35 Hz), 3.08 (d, 2H, J=11.35 Hz), 2.37-2.27 (m, 2H), 2.10-2.00 (m, 6H), 1.75-1.60 (m, 2H), 0.91 (s, 18H), 0.10 (s, 12H).

1,1=-[[(Pentane-1,5-diyl)dioxy]bis[2-amino-5-methoxy-1,4-phenylene)carbonyl]]-bis[(2S,4R)-2-t-butyldimethylsilyloxymethyl-4-hydroxypyrrolidine] (55)

A methanolic solution of hydrazine hydrate (1.25 mL, 1.29 g, 40.2 mmol of hydrazine, 20 mL of methanol) was added dropwise to a solution of the bis-nitro compound 54 (3.6 g, 3.91 mmol) in methanol (68 mL) gently refluxing over Raney nickel (510 mg of a thick slurry). After 5 minutes at reflux TLC (10% MeOH, 90% chloroform) revealed the incomplete consumption of starting material. The reaction mixture was treated with additional Raney nickel (c 510 mg) and hydrazine (1.25 mL) in methanol (20 mL) resulting in complete consumption of starting material. Excess Raney nickel was added to the reaction mixture to decompose unreacted hydrazine hydrate and the reaction mixture was then allowed to cool. The reaction mixture was filtered through celite to remove excess Raney nickel and the filter pad washed with additional methanol (Caution! Raney nickel is pyrophoric, do not allow filter pad to dry, use conc. HCl to destroy nickel). The combined filtrate was evaporated by rotary evaporation under reduced pressure and the residue re-dissolved in dichloromethane. The dichloromethane solution was dried over magnesium sulphate (to remove water associated with the hydrazine), filtered and evaporated to afford the product (55) as a foam (3.37 g, 91%): $^1$H NMR (270 MHz, CDCl$_3$) δ 6.69 (s, 2H), 6.24 (s, 2H), 4.40-3.40 (m, 28H), 2.40-1.60 (m, 10H), 0.88 (s, 18H), 0.03 (s, 12H).

1,1=-[[(Pentane-1,5-diyl)dioxy]bis[2-amino-N-allyloxycarbonyl-5-methoxy-1,4-phenylene)carbonyl]]-bis[(2S,4R)-2-t-butyldimethylsilyloxymethyl-4-hydroxypyrrolidine] (56)

A solution of allyl chloroformate (0.806 mL, 0.916 g, 7.6 mmol) in dry dichloromethane (63 mL) was added, dropwise, to a solution of the bis-amine 55 (3.27 g, 3.8 mmol) and pyridine (1.26 g, 1.29 mL, 15.9 mmol) in dichloromethane (128 mL) at 0° C. under a nitrogen atmosphere. The reaction mixture was allowed to warm to room temperature and to stir for 16 h. At which time TLC (10% MeOH, 90% Chloroform) revealed reaction to be complete. The reaction mixture was diluted with dichloromethane (40 mL) and washed with sat. copper II sulphate (2×140 mL), water (120 mL) and sat. sodium chloride (120 mL). The organic phase was dried over magnesium sulphate, filtered and evaporated under reduced pressure to afford 56 as a foam (3.60 g, 92%): $^1$H NMR (270 MHz, CDCl$_3$) δ 8.87 (bs, 2H), 7.66 (s, 2H), 6.77 (s, 2H), 6.05-5.80 (m, 2H), 5.40-5.15 (m, 4H), 4.70-4.50 (m, 6H), 4.38 (bs, 2H), 4.20-4.00 (m, 4H), 3.78 (s, 6H), 3.70-3.40 (m, 8H), 2.40-2.20 (m, 2H), 2.10-1.80 (m, 6H), 1.75-1.55 (m, 2H), 0.89 (s, 18H), 0.04 (s, 12H).

1,1=-[[(Pentane-1,5-diyl)dioxy]bis[2-amino-N-allyloxycarbonyl-5-methoxy-1,4-phenylene)carbonyl]]-bis[(2S)-2-t-butyidimethylsilyloxymethyl-4-oxopyrrolidine] (57)

A solution of dimethyl sulphoxide (1.47 mL, 1.62 g, 20.7 mmol) in dry dichloromethane (32 mL) was added dropwise over 45 minutes to a stirred solution of oxalyl chloride (5.18 mL of a 2 M solution in dichloromethane, 10.35 mmol) at −60° C. under a nitrogen atmosphere. After stirring at −50° C. for 30 minutes, a solution of the bis-alcohol 56 (3.55 g, 3.45 mmol) in dichloromethane (53 mL) was added dropwise over a period of 50 minutes. The reaction mixture was allowed to stir at −60° C. for 30 minutes prior to the dropwise addition of a solution of triethylamine (4.75 g, 6.54 mL, 46.9 mmol) in dichloromethane (27 mL). Stirring was continued at −60° C. for 45 minutes and then allowed to warm to 0° C. The reaction mixture was diluted with dichloromethane (20 mL), washed with cold 1 M HCl (2×100 mL), sat. sodium chloride (100 mL) and dried over magnesium sulphate. Removal of excess solvent afforded the crude bis-ketone which was purified by flash column chromatography (50% ethyl acetate, 50% 40-60° petroleum ether) to yield the pure bis-ketone (57) as a pale yellow foam (2.54 g, 72%): $^1$H NMR (270 MHz, CDCl$_3$) δ 8.69 (bs, 2H), 7.78 (s, 2H), 6.75 (s, 2H), 6.05-5.80 (m, 2H), 5.40-5.20 (m, 4H), 4.65-4.60 (m, 4H), 4.20-3.60 (m, 20H), 2.74 (dd, 2H, J=9.25, 18.1 Hz), 2.51 (d, 2H, J=17.4 Hz), 2.00-1.90 (m, 4H), 1.75-1.65 (m, 2H), 0.87 (s, 18H), 0.05 (s, 12H).

Elaboration of bis Ketone and Preparation of the Target Molecule 1,1=-[[(Pentane-1,5-diyl)dioxy]bis[2-amino-N-allyloxycarbonyl-5-methoxy-1,4-phenylene)carbonyl]]-bis[(2S)-2-t-butyidimethylsilyloxymethyl-4-methylidene-2,3-dihydropyrrole] (58)

A solution of potassium-t-butoxide in dry THF (0.5 M, 25.2 mL, 12.6 mmol) was added dropwise to a suspension of methyltriphenylphosphonium bromide (4.50 g, 12.6 mmol) in dry THF (15 mL). The resulting yellow ylide suspension was allowed to stir at 0° C. for 2 hours before the addition of a solution of the bis-ketone 57 (2.48 g, 2.42 mmol) in THF (10 mL) at 10° C. The reaction mixture was allowed to warm to room temperature and stirring was continued for a further hour. The reaction mixture was partitioned between ethyl acetate (100 mL) and water (100 mL) and the organic layer was washed with sat. sodium chloride (200 mL) and dried over magnesium sulphate. Removal of excess solvent gave a brown oil that was subjected to flash column chromatography (50% ethyl acetate, 50% 40-60° petroleum ether) to afford the product (58) as a yellow glass (865 mg, 35%): $^1$H NMR (400 MHz, CDCl$_3$) δ 8.90 (bs, 2H), 7.83 (s, 2H), 6.82 (s, 2H), 6.05-5.90 (m, 2H), 5.40-5.20 (m, 4H), 4.99 (bs, 2H), 4.91 (bs, 2H), 4.65-4.60 (m, 4H), 4.20-3.60 (m, 20H), 2.70 (bs, 4H), 2.00-1.90 (m, 4H), 1.75-1.63 (m, 2H), 0.88 (s, 18H), 0.03 (s, 12H).

1,1=-[[(Pentane-1,5-diyl)dioxy]bis[2-amino-N-allyloxycarbonyl-5-methoxy-1,4-phenylene)carbonyl]]-bis[(2S)-2-hydroxymethyl-4-methylidene-2,3-dihydropyrrole] (59)

A solution of TBAF (3.02 mL of a 1 M solution in THF, 3.02 mmol) was added to the bis-silyl ether (58) (1.23 g, 1.21 mmol) in THF (30 mL) at 0° C. (ice/acetone). The reaction mixture was allowed to warm to room temperature and to stir overnight, the following day, TLC (50:50 EtOAc/Pet-Ether 40°-60°) revealed the complete disappearance of starting material. Saturated NH$_4$Cl (150 mL) was added and the reaction mixture extracted with EtOAc (3×60 mL), washed with sat. sodium chloride (150 mL), dried (MgSO$_4$), filtered and evaporated in vacuo to give a yellow oil. Purification by flash chromatography (97% CHCl$_3$/3%MeOH) provided the pure alcohol (59) (916 mg, 96%): $^1$H NMR (400 MHz, CDCl$_3$) δ 8.61 (bs, 2H), 7.58 (s, 2H), 6.79 (s, 2H), 6.05-5.90 (m, 2H), 5.40-5.20 (m, 4H), 5.01 (bs, 2H), 4.93 (bs, 2H), 4.65-4.60 (m, 4H), 4.20-3.60 (m, 20H), 2.76 (dd, 2H, , J=8.42, 15.74 Hz), 2.47 (d, 2H, J=15.93 Hz), 2.00-1.90 (m, 4H), 1.80-1.63 (m, 2H).

1,1=[[(Pentane-1,5-diyl)dioxy]bis(11S,11aS)-10-(allyloxycarbonyl)-11-hydroxy-7-methoxy-2-methylidene-1,2,3,10,11,11a-hexahydro-5H-pyrrolo[2,1-c][1,4-benzodiazepin-5-one] (60)

A solution of dimethyl sulphoxide (0.57 mL, 0.63 g, 8.07 mmol) in dry dichloromethane (17 mL) was added dropwise, over a 40 minute period, to a stirred solution of oxalyl chloride (2.02 mL, of a 2 M solution, 4.04 mmol) at −45° C. under a nitrogen atmosphere. The reaction mixture was allowed to stir for 40 minutes at −45° C. followed by addition of the diol 59 (0.89 g, 1.12 mmol) in dichloromethane (17 mL), at the same temperature, over 15 minutes. After a further 60 minutes a solution of triethylamine (1.31 mL, 9.42 mmol) in dichloromethane (9 mL) was added over a period of 40 minutes. The reaction mixture was allowed to stir at −45° C. for 40 minutes before being allowed to warm to room temperature over 45 minutes. The reaction mixture was diluted with water and the phases were allowed to separate. The organic phase was washed with 1 M HCl (2×40 mL), water (40 mL), sat. sodium chloride (40 mL) and dried over magnesium sulphate. Removal of excess solvent yielded the crude product, which was purified by flash column chromatography (1% methanol, 99% chloroform) to afford the product 60 (0.175 g, 20%): $^1$H NMR (400 MHz, CDCl$_3$) δ 7.22 (s, 2H), 6.65 (s, 2H), 5.82-5.70 (m, 2H), 5.58 (d, 2H, J=9.70 Hz), 5.25-5.00 (m, 8H), 5.75-4.35 (m, 4H), 4.30 (d, 2H, J=16.10 Hz), 4.15 (d, 2H, J=17.03 Hz), 4.01 (t, 4H, J=6.32 Hz), 3.90 (s, 6H), 3.64 (t, 2H, J=8.70 Hz), 3.00-2.85 (m, 2H), 2.71 (d, 2H, J=16.29 Hz), 2.00-1.85 (m, 4H), 1.70-1.60 (m, 2H).

1,1=[[(pentane-1,5-diyl)dioxy]bis[(11aS)-7-methoxy-2-methylidene-1,2,3,11a-tetrahydro-5H-pyrrolo[2,1-c][1,4]benzodiazepin-5-one] (61)

A catalytic amount of tetrakis(triphenylphosphine)palladium (13 mg, 11.2 μmol) was added to a stirred solution of the bis-alloc-carbinolamine (60) (170 mg, 0.22 mmol), triphenylphosphine (5.7 mg, 21.6 μmol) and pyrrolidine (31 mg, 37.3 μL 0.45 mmol) in DCM (13 mL) at 0° C. (ice/acetone) under a nitrogen atmosphere. The reaction mixture was allowed to warm to room temperature and the progress of reaction monitored by TLC (95% CHCl$_3$/MeOH). After 2 hours TLC revealed the reaction was complete to give a spot, which fluoresced brightly under UV light. The solvent was evaporated under reduced pressure and the resulting residue subjected to flash chromatography (99% to 98 CHCl$_3$/MeOH) to give the bis-imine target molecule 61 as a pale yellow glass (84.5 mg, 75%) which was repeatedly evaporated in vacuo with CHCl$_3$ to provide the imine form: $^1$H NMR (400 MHz, CDCl$_3$) δ 7.68 (d, 2H, J=4.39 Hz), 7.49 (s, 2H), 6.80 (s, 2H), 5.19 (bs, 2H), 5.16 (bs, 2H), 4.28 (bs, 4H), 4.15-4.00 (m, 4H), 3.92 (s, 6H), 3.90-3.80 (m, 2H), 3.12 (dd, 2H, , J=8.97, 15.93 Hz), 2.95 (d, 2H, J=15.93 Hz), 2.00-1.85 (m, 4H), 1.72-1.67 (m, 2H).

Example 1(f)

Figure 7:
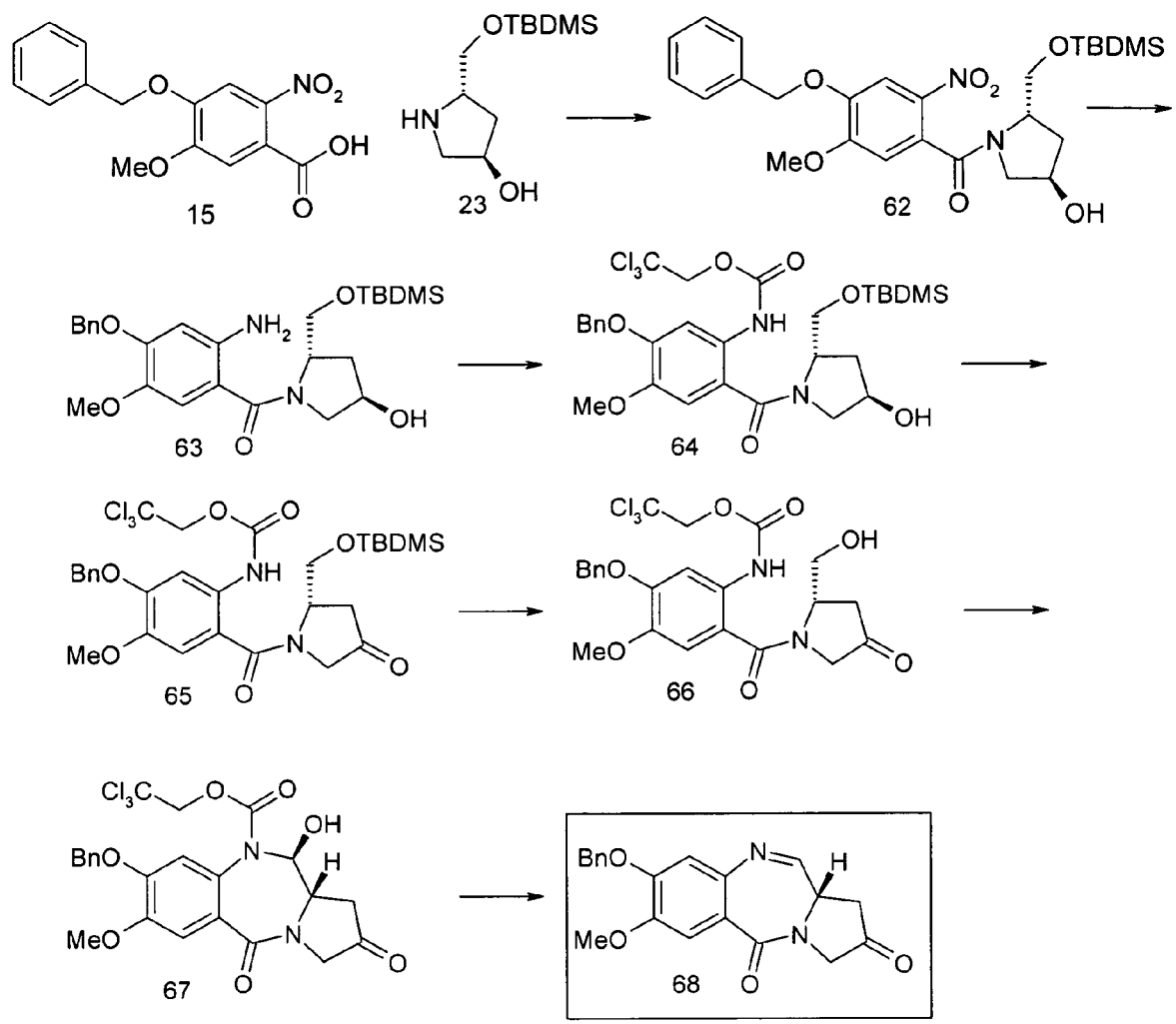

Synthesis of PBD with Ketone on C-Ring (68, UP-2067) (see FIG. 7)

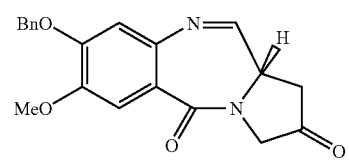

Synthesis of the Nitro Alcohol (62)

A solution of the acid 15 (3.03 g, 10 mmol, 1 equiv) in freshly distilled CH$_2$Cl$_2$ (50 mL) was treated with oxalyl chloride (1.05 mL, 12 mmol, 1.2 equiv) under a nitrogen atmosphere and stirred. DMF (0.1 mL) was added and the solution effervesced. The reaction was allowed to stir overnight at RT. The following day the acid chloride solution was added dropwise over 2 hours to a stirred mixture of the amine 23 (2.31 g, 10 mmol, 1 equiv) and TEA (3.48 mL, 25 mmol, 2.5 equiv) in freshly distilled $CH_2Cl_2$ (30 mL) while the temperature was kept under 0° C., under a nitrogen atmosphere. The reaction mixture was then allowed to warm to RT and stirred overnight. The solution was washed with $NaHCO_3$ (100 mL), saturated $NH_4Cl$ (100 mL), $H_2O$ (100 mL), brine (100 mL), dried ($MgSO_4$), filtered and evaporated in vacuo to give a brown oil which was purified by flash chromatography ($SiO_2$, EtOAc) and provided the coupled compound 62 (3.24 g, 6.28 mmol, 62.8%) as a yellow glass: $^1H$ NMR ($CDCl_3$, 270 MHz) rotamers: δ −0.10 (s, 6H, Si(CH$_3$)$_2$), 0.80 (s, 9H, SiC(CH$_3$)$_3$), 2.04-2.55 (m, 3H, 1-H, OH), 3.05-4.60 (m, 9H, 11-H, 11a-H, OMe, 3-H, 2-H), 5.20 (br s, 2H, OBn), 6.78 and 6.85 (2×s, 1H, 6-H), 7.27-7.47 (m, 5H, Ph), 7.73 and 7.76 (2×s, 1H, 9-H); $^{13}C$ NMR ($CDCl_3$, 270 MHz): δ −5.5, −5.4, 18.2, 25.7, 25.8, 36.3, 56.6, 57.2, 62.6, 70.2, 71.3, 109.0, 109.4, 127.6-128.8, 135.2, 137.3, 147.9, 154.7, 166.6; IR (neat): 3401, 3065, 3033, 2951, 2856, 2739, 2628, 1956, 1743, 1620, 1578, 1522, 1462, 1434, 1378, 1336, 1277, 1221, 1075, 1051, 1002, 914, 836, 779, 752, 697, 669, 650, 615; EIMS m/z (relative intensity) 516 ($M^+$, 0.6), 460 (29.8), 459 (92.6), 368 (7.9), 286 (49.6), 91 (100.0), 73 (9.5); FAB m/z (relative intensity) 517 ($M^+$+1, 15.1), 385 (9.2), 286 (19.3), 92 (9.3), 91 (100.0), 75 (14.0), 73 (42.2).

Reduction to the Amino Alcohol (63)

A solution of hydrazine (3.11 mL, 100 mmol, 5 equiv) in MeOH (50 mL) was added dropwise to a refluxing solution of the nitro compound 62 (10.32 g, 20 mmol, 1 equiv), antibumping granules and Raney Ni (3.5 g) in MeOH (150 mL). After 1 hour at reflux TLC ($SiO_2$, 5% MeOH—$CHCl_3$) revealed total consumption of starting material. The mixture was then treated with sufficient Raney Ni to decompose any unreacted hydrazine. After cooling to RT the mixture was filtered through Celite and the filtrate evaporated in vacuo. The resulting residue was dissolved in $CH_2Cl_2$ (300 mL), dried ($MgSO_4$), filtered and evaporated in vacuo to provide 63 (6.80 g, 14 mmol, 70%) as a pink oil which was carried through to the next stage without purification: $^1H$ NMR ($CDCl_3$, 270 MHz) rotamers: δ −0.001 (s, 6H, Si(CH$_3$)$_2$), 0.88 (br s, 9H, SiC(CH$_3$)$_3$), 1.96-2.23 (m, 2H, 1-H), 3.44-4.48 (m, 12H, 11-H, 3-H, OMe, NH$_2$, OH, 2-H, 11a-H), 5.09 (br s, 2H, OBn), 6.25 and 6.27 (2×s, 1H, 6-H), 6.68 and 6.73 (2×s, 1H, 9-H), 7.26-7.42 (m, 5H, Ph); $^{13}C$ NMR ($CDCl_3$, 270 MHz): δ −5.4, 18.2, 25.9, 35.7, 56.9, 57.2, 70.4, 70.7, 103.2, 112.9, 113.4, 127.2, 127.4, 127.9, 128.6, 128.6, 136.7, 141.6; IR (neat): 3356.80, 2930.13, 2857.36, 2247.82, 1622.19, 1514.60, 1463.60, 1408.95, 1261.43, 1176.55, 1118.48, 1003.88, 911.00, 836.61, 778.15, 733.59, 697.72, 646.32.

(2S)(4R)-N-[4-benzyloxy-5-methoxy-2-(2',2',2'-trichloroethoxy)carbonyl]-2-(tert-butyidimethylsilyloxymethyl)-4-hydroxypyrrolidine (64)

A solution of 2,2,2-trichloroethylchloroformate (8.74 g, 5.68 mL, 41.2 mmol) in dichloromethane (50 mL) was added to a solution of 4 (18.2 g, 37.5 mmol) and pyridine (5.92 g, 6.1 mL, 75.0 mmol) in dry dichloromethane (200 mL) at 0° C. under a nitrogen atmosphere.

The reaction mixture was allowed to stir overnight at room temperature and was then washed with saturated copper sulphate solution (100 mL), water (100 mL) and brine (100 mL).

The organic phase was dried over magnesium sulphate, filtered and excess solvent removed by rotary evaporation to afford the product 64 (22.01 g, 33.2 mmol, 89%) which was used in the subsequent reaction without further purification. $^1H$ NMR (270 MHz, $CDCl_3$) δ 9.31 (bs, 1H); 7.48 (s, 1H); 7.45-7.28 (m, 5H); 6.82 (s, 1H); 5.17 (bs, 2H); 4.89 (d, J=11.9 Hz, 1H); 4.70 (d, J=11.9 Hz, 1H); 4.56 (bs, 1H); 4.40 (bs, 1H); 4.20-4.00 (m, 1H); 3.95-3.40 (m, 7H); 2.40-2.00 (m, 2H); 0.09 (s,9H); 0.04 (s, 6H). $^{13}C$ NMR (67.8 MHz, $CDCl_3$) δ 169.2, 152.1, 150.2, 136.1, 128.6, 128.1, 127.7, 111.6, 106.2, 95.2, 74.4, 70.7, 70.5, 62.1, 57.2, 56.4, 35.4, 25.8, 18.1, −5.46.

(2S)-N-[4-benzyloxy-5-methoxy-2-(2',2',2'-trichloroethoxy)carbonyl amino]-2-(tert-butyidimethylsilyloxymethyl)-4-oxopyrrolidine (65)

A solution of DMSO (7.80 g, 99.8 mmol) in dry dichloromethane (18 mL) was added dropwise, over 30 minutes, to a solution of oxalyl chloride (6.34 g, 49.9 mmol) in dry dichloromethane (25 mL) at −45° C. under a nitrogen atmosphere and the reaction mixture allowed to stir for a further 15 minutes. A solution of the substrate 64 (22.01 g, 33.3 mmol) in dichloromethane (50 mL) was added dropwise over 40 minutes to the reaction mixture, which was then allowed to stir for 45 minutes at −45° C. Finally, neat triethylamine (23.52 g, 232.9 mmol) was added dropwise over 30 minutes and the reaction mixture allowed to stir at −45° C. for 15 minutes. The reaction mixture was allowed to warm to room temperature, diluted with water (150 mL) and the organic phase washed with dilute HCl (1N, 100 mL), water (100 mL) and brine (100 mL). The organic phase was dried over magnesium sulphate, filtered and concentrated in vacuo to afford the crude product which was subjected to column chromatography (ethyl acetate/40-60 petroleum ether, 50:50). Removal of excess eluant afforded the product (20.15 g, 92% yield). $^1H$ NMR (270 MHz, CDCl3) δ 7.88 (bs, 1H); 7.49-7.28 (m, 5H); 6.80 (s, 1H); 5.22 (d, J=12.1 Hz, 1H); 5.17 (d, J=12.1 Hz, 1H); 4.80 (bs, 2H); 4.10-3.60 (m, 8H); 2.75 (dd, J=18.0, 9.5 Hz, 1H); 2.52 (d, J=18.0 Hz, 1H); 0.87 (s, 9H); 0.06 (s, 3H); 0.05 (s, 3H). $^{13}C$ NMR (67.8 MHz) δ 208.7, 168.8, 151.8, 150.6, 144.7, 136.0, 128.5, 128.1, 127.7, 110.9, 106.4, 95.2, 74.4, 70.7, 66.0, 56.8, 56.4, 39.4, 25.8, 18.0, −5.7.

(2S)-N-[4-benzyloxy-5-methoxy-2-(2',2',2'-trichloroethoxy)carbonyl amino]-2-(hydroxymethyl)-4-oxopyrrolidine (66)

Glacial acetic acid (60 mL) and water (20 mL) were added to a solution of ketone 65 (9.44 g, 14.3 mmol) in THF (20 mL) and the reaction mixture allowed to stir for 3 hr. (reaction complete by TLC). The reaction mixture was diluted with dichloromethane (200 mL) and neutralized dropwise with sat. sodium bicarbonate (1.5 L) in a 5 L flask (effervescence!). The phases were allowed to separate and the aqueous layer extracted with dichloromethane (2×100 mL). The combined organic layers were washed with brine and dried over magnesium sulphate. Removal of excess solvent afforded the crude product which was subjected to column chromatography on silica (ethyl acetate/40-60 petroleum ether, 50:50) to give the pure product (6.44 g, 83%). $^1H$ NMR (270 MHz, $CDCl_3$) δ 8.77 (bs, 1H); 7.57 (s, 1H);

7.46-7.28 (m, 5H); 6.83 (s,1H); 5.13 (s, 2H); 4.85-4.70 (m, 3H); 4.07-3.60 (m, 7H); 2.77 (dd, J=18.5, 9.5 Hz, 1H); 2.54 (d, J=18.5 Hz, 1H). $^{13}$C NMR (67.8 MHz, CDCl$_3$) δ 209.0, 169.4, 152.3, 150.6, 145.5, 136.0, 130.0, 128.6, 128.3, 127.6, 110.9, 107.4, 95.2, 74.5, 70.8, 64.4, 60.4, 56.6, 55.9, 39.5.

(11s,11aS)-4-benzyloxy-11-hydroxy-5-methoxy-4-oxo-10-(2',2',2'-trichloroethoxy)carbonyl-amino 1,10,11,11a-tetrahydro-5H-pyrrolo-[2,1-c][1,4]benzodiazepin-5-one (67)

A solution of DMSO (4.45 g, 4.04 mL, 56.9 mmol) in dry dichloromethane (25 mL) was added dropwise, over 5 minutes, to a solution of oxalyl chloride (3.58 g, 49.9 mmol) in dry dichloromethane (14 mL) at −60° C. under a nitrogen atmosphere and the reaction mixture allowed to stir for a further 15 minutes. A solution of the substrate 66 (10.93 g, 20.0 mmol) in dichloromethane (25 mL) was added dropwise over 30 minutes to the reaction mixture, which was then allowed to stir for 30 minutes at −60° C. Finally, neat triethylamine (11.15 g, 232.9 mmol) was added dropwise over 30 minutes and the reaction mixture allowed to stir at −60° C. for 15 minutes. The reaction mixture was allowed to warm to room temperature, diluted with water (150 mL) and the organic phase washed with dilute HCl (1N, 100 mL), water (100 mL) and brine (100 mL). The organic phase was dried over magnesium sulphate, filtered and concentrated in vacuo to afford the crude product which was subjected to column chromatography (ethyl acetate/40-60 petroleum ether, 50:50). Removal of excess eluent afforded the product 67 (9.66 g, 89% yield). $^1$H NMR (270 MHz, CDCl$_3$) δ 7.45-7.33 (m, 5H); 7.27 (s, 1H); 6.95 (s, 1H); 5.76 (d, J=9.9 Hz, 1H); 5.52-5.00 (m, 3H), 4.33 (d, J=6.8 Hz, 1H); 4.30 (d, J=19.2 Hz, 1H); 4.00-3.70 (m, 5H); 2.98 (dd, J=20.0, 10.4 Hz, 1H); 2.94 (d, J=20.0 Hz, 1H). $^{13}$C NMR (67.8 MHz) δ 207.7, 167.5, 154.5, 152.6, 150.8, 149.6, 135.8, 128.9-127.3, 124.0, 114.5, 110.8, 95.0, 86.6, 75.0, 71.1, 56.8, 56.2, 52.6, 40.2.

(11aS)-4-benzyloxy-5-methoxy-4-oxo-1,10,11,11a-tetrahydro-5H-pyrrolo[2,1-c][1,4]benzodiazepin-5-one (68)

Cadmium/lead couple (1.15 g) was added to a solution of cyclized ketone (67, 1 g, 1.84 mmol) in THF (5 mL) and aqueous ammonium acetate (1N, 15 mL). The reaction mixture was allowed to stir for 90 minutes and then filtered through celite. The celite pad was washed with ethyl acetate (2×25 mL) and the organic layer separated. The organic layer was washed with brine (50 mL) and dried over magnesium sulphate. Removal of excess solvent followed by column chromatography afforded the pyrrolobenzodiazepine 68 (0.324 g, 0.93 mmol). $^1$H NMR (270 MHz, CDCl$_3$) δ 7.75 (d, J=4.4 Hz, 1H); 7.51 (s, 1H); 7.46-7.27 (m, 5H); 5.23 (d, J=12.3 Hz, 1H); 5.17 (d, J=12.3 Hz, 1H), 4.24-4.40 (m, 3H), 3.96 (s, 3H), 3.12 (dd, J=19.6, 8.8 Hz, 1H); 2.99 (dd, J=5.0 Hz, 1H). $^{13}$C NMR (67.8 MHz) δ 206.7, 165.5, 161.4, 151.1, 148.5, 140.5, 136.0, 128.7-127.1, 118.9, 111.7, 111.3, 70.9, 56.4, 53.4, 51.0, 40.0.

Example 1(g)

Figure 8:
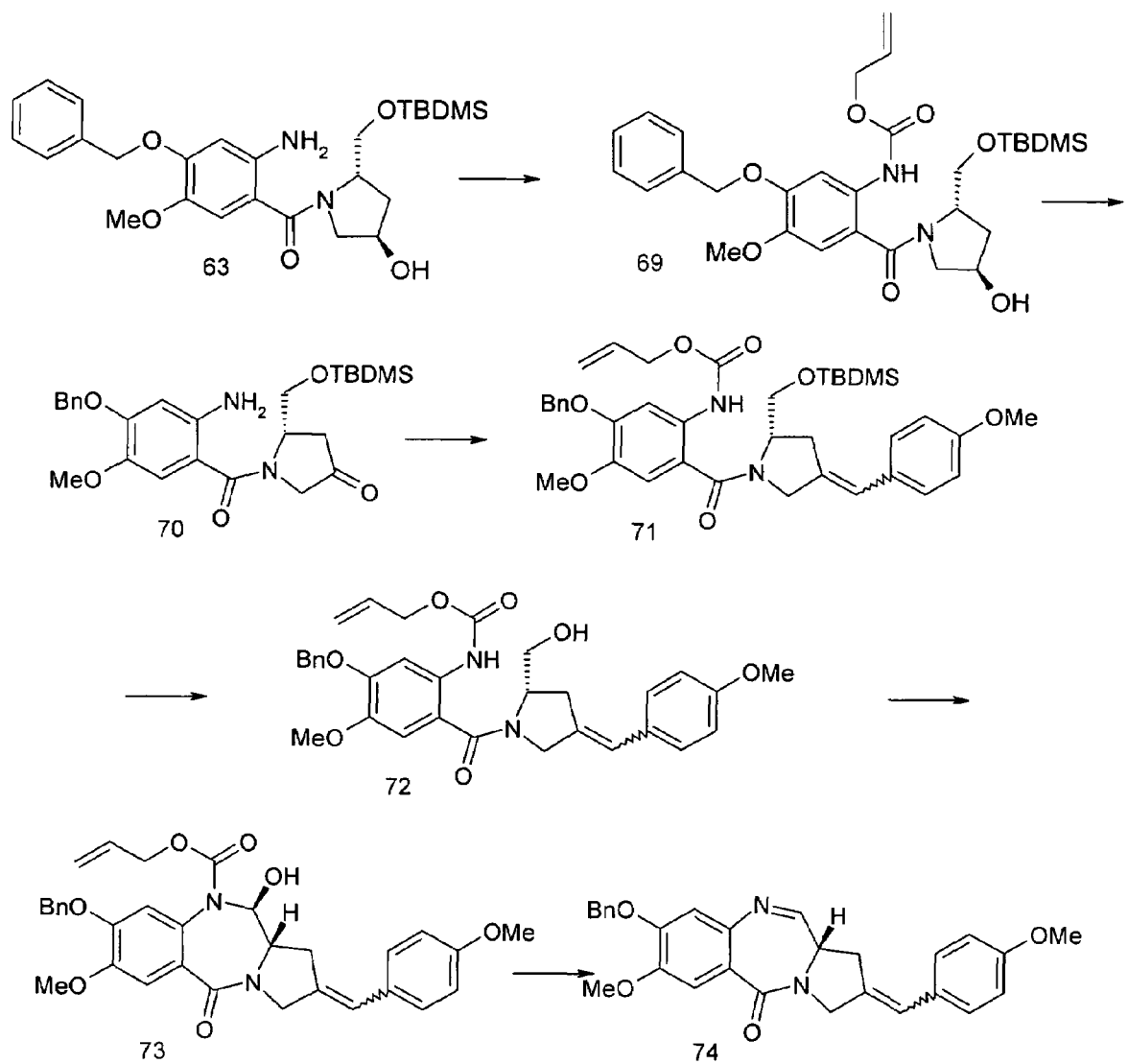

Synthesis of (11aS)-8-Benzyloxy-7-methoxy-2-(4-methoxybenzylidene-1,2,3,11a,-tetrahydro-5H-pyrrolo[2,1-c][1,4]benzodiazepine-5-one (74) (see FIG. 8)

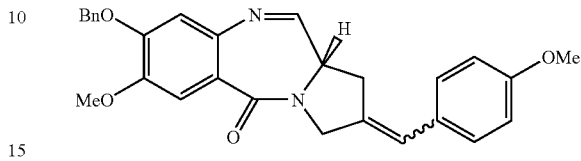

Synthesis of the Alloc Pro-N10-Protected C2-Alcohol (69)

A solution of allyl chloroformate (1.54 mL, 14.48 mmol, 1.05 equiv) in freshly distilled CH$_2$Cl$_2$ (30 mL) was added dropwise to a stirred mixture of the amine 63 (6.70 g, 13.79 mmol, 1 equiv), pyridine (2.45 mL, 30.34 mmol, 2.2 equiv) in freshly distilled CH$_2$Cl$_2$ (200 mL), at 0° C. under a nitrogen atmosphere. The mixture was allowed to warm at RT and stirred overnight. The following day TLC (SiO$_2$, 5% MeOH—CHCl$_3$) revealed reaction completion. The mixture was washed with saturated CuSO$_4$ (100 mL), H$_2$O (100 mL), brine (100 mL), dried (MgSO$_4$), filtered and evaporated in vacuo to give a dark yellow oil. Flash chromatography (SiO$_2$, 30% EtOAc-petroleum ether) afforded the pure Alloc-compound 69 (6.70 g, 11.75 mmol, 85.2%) as a yellow oil: $^1$H NMR (CDCl$_3$, 270 MHz) rotamers: δ 0.03 and 0.04 (2×s, 6H, Si(CH$_3$)$_2$), 0.89 (br s, 9H, SiC(CH$_3$)$_3$), 1.99-2.40 (m, 2H, 1-H), 3.56 (br s, 4H, 11-H, 3-H), 3.79 (s, 3H, OMe), 4.05-4.20 (m, 1H, 11a-H), 4.38 (s, 1H, 2-H), 4.58-4.62 (m, 3H, OH, Alloc), 5.16-5.37 (m, 4H, OBn, Alloc), 5.86-6.00 (m, 1H, Alloc), 6.80 (s, 1H, 6-H), 7.30-7.48 (m, 5H, Ph), 7.80 (s, 1H, 9-H), 8.86 (br s, 1H, NH); $^{13}$C NMR (CDCl$_3$, 270 MHz): δ −5.5, 5.4, 18.1, 25.8, 35.6, 56.4, 57.2, 60.4, 65.8, 70.5, 70.7, 106.4, 111.7, 116.4, 118.0, 127.7-128.6, 132.5, 136.3, 144.3, 150.2, 153.8, 169.4; IR (neat): 3336, 3067, 2953, 2931, 2858, 1732, 1600, 1525, 1464, 1408, 1327, 1225, 1175, 1121, 1048, 1028, 1002, 937, 837, 812, 778, 744, 698, 671, 636, 608, 562; EIMS m/z (relative intensity) 570 (M$^+$, 35.0), 513 (27.2), 340 (19.3), 149 (24.3), 91 (24.1), 77 (16.4), 58 (33.0), 57 (100.0), 44 (27.2), 39 (39.8); [α]$^{23}_D$=−55.94° (c=1.010, CHCl$_3$).

Oxidation to the C2-Ketone (70)

A solution of DMSO (2.50 mL, 35.25 mmol, 3 equiv) in freshly distilled CH$_2$Cl$_2$ (200 mL) was added dropwise over 1.5 hours to a stirred solution of oxalyl chloride (8.81 mL of a 2M solution in CH$_2$Cl$_2$, 17.62 mmol, 1.5 equiv) at −55/−60° C. (liquid nitrogen/CHCl$_3$) under a nitrogen atmosphere. After 30 minutes stirring at −55° C., a solution of the secondary alcohol 69 (6.70 g, 11.75 mmol, 1 equiv) in CH$_2$Cl$_2$ (150 mL) was added dropwise to the reaction mixture over 1.5 h. Following stirring at −55/−60° C. for 45 minutes the reaction was treated dropwise with a solution of TEA (11.14 mL, 79.90 mmol, 6.8 equiv) in CH$_2$Cl$_2$ (50 mL) over a period of 40 minutes. The mixture was stirred for a further 45 minutes at −30□C and was then allowed to warm to RT. The reaction was then treated with brine (150 mL), cooled to 0° C. and acidified to pH=2 with concentrated HCl. The organic phase was washed with H$_2$O (150 mL), brine (150 mL), dried (MgSO$_4$), filtered and evaporated in vacuo to give the ketone 70 as a dark orange oil (6.18 g, 10.88 mmol, 93%), sufficiently pure by TLC (SiO$_2$, 40%

EtOAc-petroleum ether) to be carried through to the next stage without further purification: $^1$H NMR (CDCl$_3$, 270 MHz) rotamers: δ 0.04 and 0.05 (2×s, 6H, Si(CH$_3$)$_2$), 0.87 (s, 9H, SiC(CH$_3$)$_3$), 2.47-2.78 (m, 2H, 1-H), 3.66-4.10 (m, 8H, 3-H, OMe, 11-H, 11a-H), 4.62-4.65 (m, 2H, Alloc), 4.80-5.40 (m, 4H, OBn, Alloc), 5.88-6.03 (m, 1H, Alloc), 6.76 (s, 1H, 6-H), 7.27-7.49 (m, 5H, Ph), 7.90 (s, 1H, 9-H), 8.62 (br s, 1H, NH); $^{13}$C NMR (CDCl$_3$, 270 MHz): δ −5.8, −5.7, 18.0, 25.6, 25.7, 56.5, 65.8, 68.0, 70.7, 106.4, 111.0, 118.2, 127.7-128.6, 132.4, 136.1, 150.6, 153.4, 208.9; IR (neat): 3510, 3332, 2957, 2870, 2740, 1959, 1771, 1738, 1633, 1537, 1428, 1274, 1233, 1120, 1029, 844, 785, 700; EIMS m/z (relative intensity) 568 (M$^+$, 90.6), 512 (28.7), 511 (79.8), 453 (12.1), 340 (38.6), 298 (12.7), 282 (16.9), 172 (23.9), 91 (100.0), 41 (15.1); [α]$^{23}_D$=−1.98° (c=1.010, CHCl$_3$).

(2S)-N-[(2-allyloxycarbanylamino)-4-benzyloxy-5-methoxy]-2-(tert butyidimethylsilyloxymethyl)-4-methylidenepyrrolidine (72)

The Wittig reagent, 4-methoxybenzylphosphonium bromide (3.686 g, 0.88 mmol) was added portionwise to a suspension of sodium hydride (352 mg of a 60% dispersion, 8.80 mmol) in anhydrous toluene (25 mL) under a nitrogen atmosphere at 0° C. The mixture was allowed to warm to room temperature and then heated at reflux for 30 minutes. The colour of the reaction mixture darkened progressively from yellow through to orange. At this stage a solution of the ketone (70) (0.5 g, 0.88 mmol) in dry toluene (25 mL) was added dropwise to the reaction mixture at reflux. After 10 minutes TLC (50% ethyl acetate, 50% 40-60° petroleum ether) revealed the complete consumption of ketone. Excess toluene was removed by rotary evaporation under reduced pressure to yield a brown residue, which was partitioned between ethyl acetate (100 mL) and saturated sodium hydrogen carbonate (100 mL). The organic layer was washed with brine (100 mL) and dried over magnesium sulphate) removal of excess solvent by rotary evaporation under reduced pressure gave a dark oil, which was subjected to flash chromatography on silica gel (20% ethyl acetate, 70% 40-60° petroleum ether). Removal of excess eluent afforded the product (71) as an oil which solidified on standing (420 mg, 0.62 mmol, 71%). [α]$^{21}_D$−7.480 (c=1.002 CHCl$_3$). $^1$H NMR (270 MHz, CDCl$_3$) cis/trans mixture, rotamers δ 8.90 (bs, 1H), 7.95 (s, 1H), 7.76-7.65 (m, 2H), 7.55 (m, 7H), 6.9 (s, 1H), 6.4) and 6.30 (2×bs, 1H), 6.02-5.88 (m, 1H), 5.40-5.17 (s, 4H), 4.64-4.59 (m, 2H), 3.91-3.70 (m, 9H), 3.00-2.95 (m, 2H). HRMS (FAB) 673 (M+1). Anal. Calcd for C$_{38}$H$_{48}$N$_2$O$_7$Si: C, 67.83; H, 7.19; N, 4.16. Found C, 67.64; H, 7.33; N, 4.03.

(2S)-N-[(2-allyloxycarnoylamino)-4-benzyloxy-5-methoxy]-2-(hydroxymethyl)-4-(4-methoxybenzylidene)pyrrolidine (72)

A solution of TBAF in THF (1.21 mL, 1 M solution, 1.21 mmol) was added to a solution of 71 (0.65 g, 0.97 mmol) in THF (15 mL) at 0° C. The reaction mixture was allowed to warm to room temperature and stir overnight. Excess THF was removed by rotary evaporation under reduced pressure and the residue was partitioned between ethyl acetate (100 mL) and saturated ammonium chloride (1 mL). The organic phase was washed with brine (100 mL) and dried over magnesium sulphate. Excess solvent was evaporated under reduced pressure and the resulting residue was subjected to flash column chromatography (silica gel, 50% ethyl acetate and 50% 40-60° petroleum ether). Removal of excess eluent by rotary evaporation under reduced pressure afforded the compound 72 (0.9 g, 1.61 mmol, 65%). $^1$H NMR (270 MHz, CDCl$_3$) cis/trans mixture δ 8.55 (bs, 1H), 7.50-7.10 (m, 8H), 6.80-6.90 (m, 3H), 6.40 and 6.29 (2×bs, 1H), 6.02-5.88 (m, 1H), 5.40-5.10 (m, 4H), 4.55-4.70 (m, 2H),4.50-4.30 (m, 1), 3.95-3.80 (m, 8H), 3.10-3.90 (m, 1H), 3.50-3.70 (m, 1H). HRMS (FAB) Calcd for C$_{32}$H$_{35}$N$_2$O$_7$ (M+H) 559.2444. Found 559.2462.

(11S,11aS)-10-allyloxycarbonyl-8-benzyloxy-11-hydroxy-7-methoxy-2-(4-methoxybenzylidene)-1,2,3,10,11,11a-hexahydro-5H-pyrrolo[2,1-c][1,4]benzodiazepine-5-one (73)

A solution of DMSO (0.41 mL, 5.80 mmol) in dry DCM (50 mL) was added dropwise to a stirred solution of oxalyl chloride (1.45 ml of a 2M solution, 2.90 mmol)at −40° C. under a nitrogen atmosphere. After 45 minutes stirring at −45° C., a solution of 72 (0.9 g, 1.61 mmol) in DCM (50 mL) was added dropwise to the mixture over 45 minutes. After stirring at −45° C. for 45 minutes the reaction mixture was treated dropwise with a solution of TEA (0.94 mL, 6.76 mmol) in DCM (20 mL) over 30 minutes. After a stirring at −45° C. for a further 40 minutes the reaction mixture was allowed to warm to room temperature and then diluted with DCM (30 mL). The diluted reaction mixture was washed with dilute hydrochloric acid (1 N, 300 mL), water (150 mL), brine (150 mL) and dried over magnesium sulphate. Removal of excess solvent afforded the crude product, which was subjected to column chromatography (silica gel, 50% ethyl acetate and 50% 40-60° petroleum ether). Removal of excess eluent afforded the product 73 as an oil (0.62 g, 1.11 mmol, 69%). $^1$H NMR (270 MHz, CDCl$_3$) cis/trans mix δ 7.50-7.10 (m, 8H), 6.90-6.85 (m, 2H), 6.74 (s, 1H), 6.50 and 6.45 (2×bs, 1H), 6.70-5.00 (m, 6H), 4.70-4.20 (m, 4H), 3.98 (s, 3H), 3.90-3.70 (m, 4H), 3.10-2.80 (m, 2H). HRMS (FAB) Calcd for C$_{32}$H$_{33}$N$_2$O$_7$ (M+H) 557.2288. Found 559.2277.

(11aS)-8-Benzyloxy-7-methoxy-2-(4-methoxybenzylidene-1,2,3,11a,-tetrahydro-5H-pyrrolo[2,1-c][1,4]benzodiazepine-5-one (74)

Triphenylphosphine, pyrrolidine and palladium tetrakistriphenylphosphine were addaed sequentially to a stirred solution of substrate 73 in dry DCM. The reaction mixture was allowed to stir at room temperature under a nitrogen atmosphere for 2 h, at which time TLC (50% ethyl acetate and 50% 40-60° petroleum ether) revealed the complete consumption of starting material. The reaction mixture was evaporated to dryness and the resulting residue subjected to gravity column chromatography (silica gel, gradient elution: 30% ethyl acetate, 70% 40-60° petroleum ether to 70% ethyl acetate, 30% 40-60° petroleum ether). Removal of excess eluent afforded the PBD (74) as a yellow glass that was reprecipitated from ethyl acetate with 40-60° petroleum ether.

$^1$H NMR (270 MHz, CDCl$_3$) cis/trans mix δ 7.69 (d, 1H, J=4.39 Hz), 7.52 (s,1 H), 7.46-7.30 (m, 5H), 7.20-7.16 (m, 2H), 6.92-6.88 (m, 2H), 6.84 (s, 1H), 6.53 (bs, 1H), 5.20-5.17 (m, 2H), 4.52 (m, 2H), 3.96 (s, 3H), 3.90-3.75 (m, 4H), 3.34-3.26 (m, 1H), 3.12-3.00 (m, 1H).

Example 2

Cytotoxicity Data

NCI In Vitro Cytotoxicity Studies

The National Cancer Institute (NCI), Bethesda, Md., USA has available an in vitro cytotoxicity screen which consists of approximately 60 human tumour cell lines against which compounds are tested at a minimum of five concentrations each differing 10-fold. A 48 hour continuous exposure protocol is used, where cell viability or growth is estimated with an SRB protein assay.

Method

The test compounds were evaluated against approximately 60 human tumour cell lines. The NCI screening procedures were described in detail by Monks and co-workers (Monks, A et al., Journal of the National Cancer Institute, 1991, 83, 757). Briefly, cell suspensions were diluted according to the particular cell type and the expected target cell density (5000-40,000 cells per well based on cell growth characteristics), and added by pipette (100 µL) into 96-well microtitre plates. The cells were allowed a preincubation period of 24 hours at 37° C. for stabilisation. Dilutions at twice the intended test concentration were added at time zero in 100 µL aliquots to the wells. The test compounds were evaluated at five 10-fold dilutions ($10^{-4}$, $10^{-5}$, $10^{-6}$, $10^{-7}$ and $10^{-8}$ µM). The test compounds were incubated for 48 hours in 5% $CO_2$ atmosphere and 100% humidity. The cells were then assayed using the sulphorhodamine B assay. A plate reader was used to read the optical densities and a microcomputer processed the readings into $LC_{50}$ values, which is the dosage required to kill half of the cells.

The results presented are $LC_{50}$ values which are below 10 µM, which is taken to be the dividing line between cytotoxicity and non-cytotoxicity.

NCI Hollow Fibre Assay for Preliminary In Vivo Testing

The Biological testing Branch of the Developmental Therapeutics Program of the NCI has adopted a preliminary in vivo screening tool for assessing the potential anticancer activity of compounds identified by the large scale in vitro cell screen. For these assays, human tumour cells are cultivated in polyvinylidene (PVDF) hollow fibres, and a sample of each cell line is implanted into each of two physiologic compartments (intraperitoneal and subcutaneaous) in mice. Each test mouse received a total of 6 fibres (3 intraperitoneally and 3 subcutaneously) representing 3 distinct cancer cell lines. These mice are treated with potential antitumour compounds at each of 2 test doses by the intraperitoneal route using a QD×4 treatment schedule. Vehicle controls consist of 6 mice receiving the compound diluent only. The fibre cultures are collected on the day following the last day of treatment. To assess anticancer effects, the viable cell mass is determined for each of the cell lines using a formazyn dye (MTT) conversion assay. From this, the %T/C can be calculated using the average optical density of compound treated samples divided by the average optical; density of the vehicle controls. In addition, the net increase in cell mass can be determined for each sample, as a sample of fibre cultures are assessed for viable cell mass on the day of implantation into mice. Thus, the cytostatic and cytocidal capacities of the test compound can be assessed.

Generally, each compound is tested against a minimum of 12 human cancer cell lines. This represents a total of 4 experiments since each experiment contains 3 cell lines. The data are reported as %T/C for each of the 2 compound doses against each of the cell lines with separate values calculated for the intraperitoneal and subcutaneous samples.

Compounds are selected for further in vivo testing in standard subcutaneous xenograft models on the basis of several hollow fibre assay criteria. These include: (1) a % T/C of 50 or less in 10 of the 48 possible test combinations (12 cell lines×2 sites×2 compound doses); (2) activity at a distance (intraperitoneal drug/subcutaneous culture) in a minimum of 4 of the 24 possible combinations; and/or (3) a net cell kill of 1 or more of the cell lines in either implant site. To simplify evaluation, a points system has been adopted which allows rapid evaluation of the activity of a given compound. For this, a value of 2 is assigned for each compound dose which results in a 50% or greater reduction in viable cell mass. The intraperitoneal and subcutaneous samples are scored separately so that criteria (1) and (2) can be evaluated. Compounds with a combined IP+SC score of 20, a SC score of 8 or a net cell kill of one or more cell lines are referred for xenograft testing. This comparison indicated that there was a very low probability of missing an active compound if the hollow fibre assay was used as the initial in vivo screening tool. In addition to these criteria, other factors (e.g. unique structure, mechanism of action) may result in referral of a compound for xenograft testing without the compound meeting these criteria.

NCI Human Xenograft Studies

These are carried out on nude athymic mice with a disabled immune system. The human tumour tissue to be tested is implanted in their flanks, and whilst the control mouse receives no treatment, the others are subjected to varying doses of the test compound, which is administered intraperitoneally. The results are expressed as the toxicity of the compound, the amount of tumour growth, and the inhibition of growth.

Example 2(a)

In Vitro Cytotoxicity of compounds of Formula II

Figure 9:
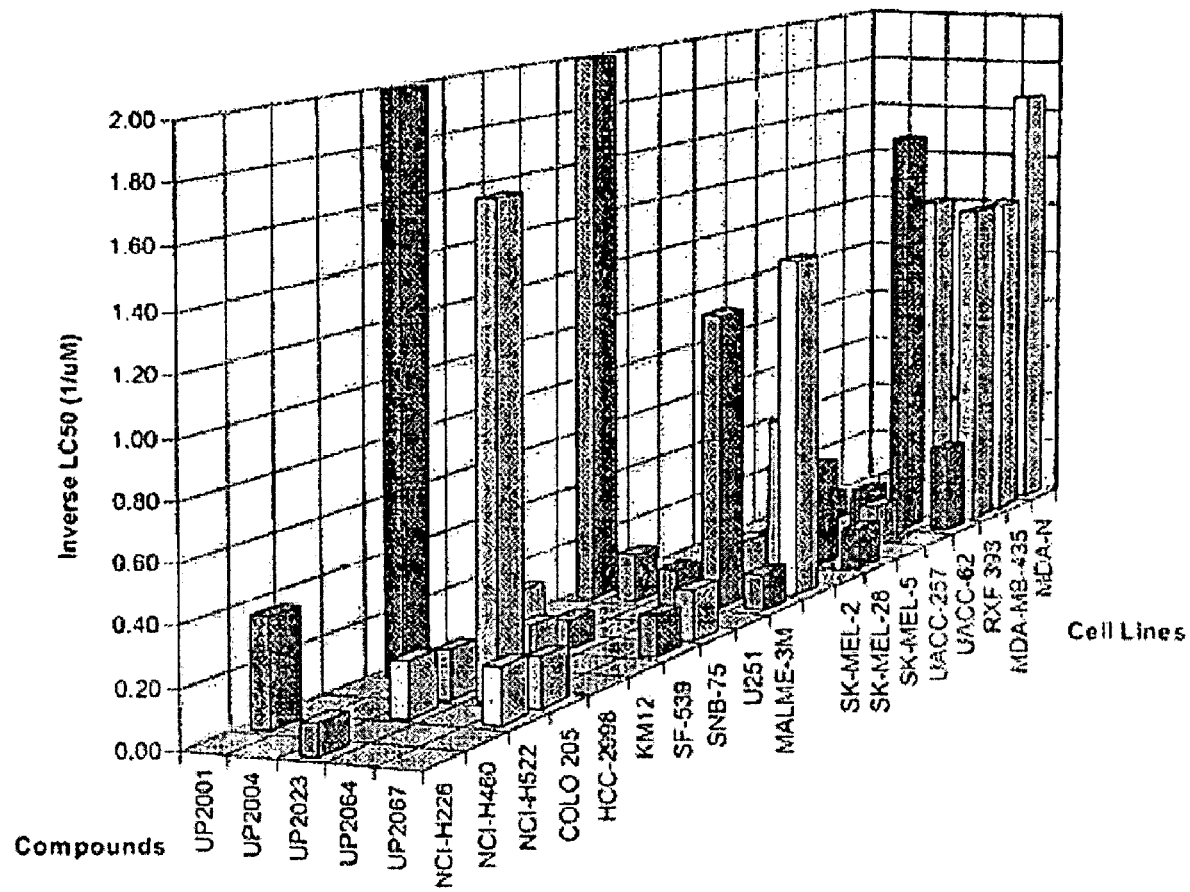
FIG. 9 is a graph illustrating the cytotoxicity results of example 2.

Some of the compounds synthesised in example 1, were subjected to the NCI In Vitro Cytotoxicity study. The results ($LC_{50}$; µM) are set out below, and are illustrated in FIG. 9.

| TU-MOUR TYPE | CELL-LINE DESIG-NATION | UP2064 (31) | UP2001 (39) | UP2004 (21) $LC_{50}(µM)$ | UP2023 (14) | UP2067 (68) |
|---|---|---|---|---|---|---|
| Lung | NCI-H23 | | | 7.6 | | |
| | NCI-H226 | | | | 9.1 | |
| | NCI-H460 | | 2.7 | | | |
| | NCI-H522 | | | | 5.2 | 5.0 |
| Colon | COLO 205 | 0.6 | | 3.9 | 5.8 | 5.8 |
| | HCC-2998 | | 0.099 | 5.5 | 7.0 | |
| | KM12 | | | | 7.1 | |
| CMS | SF-539 | | | | 9.4 | 6.8 |
| | SNB-75 | | 7.5 | | | 5.4 |
| Mela-noma | MALME-3M | 0.9 | 0.073 | | 7.8 | 7.4 |
| | M14 | | | | | 0.8 |
| | SK-MEL-2 | 1.7 | | | 7.4 | |
| | SK-MEL-28 | 2.6 | | | 8.4 | 6.6 |
| | SK-MEL-5 | | | 7.8 | 6.0 | |
| | UACC-257 | 7.4 | | 7.3 | | |
| | UACC-62 | 0.6 | 0.077 | 5.3 | 7.2 | 3.0 |

-continued

| TU-MOUR TYPE | CELL-LINE DESIG-NATION | UP2064 (31) | UP2001 (39) | UP2004 (21) LC$_{50}$(μM) | UP2023 (14) | UP2067 (68) |
|---|---|---|---|---|---|---|
| Renal | RXF 393 | 0.8 | | | 6.1 | 0.8 |
| Breast | MDA-MB-435 | 2.3 | | | 7.6 | 0.8 |
| | MDA-N | | | 9.0 | 6.6 | 0.6 |

Of the compounds tested, the above listed exert their cytotoxic effect (LC$_{50}$) most strongly in the Lung, Colon, CNS. Melanoma, Renal and Breast cell line panels. Within the group, it is apparent that exchanging a C-8 benzyloxy substituent (UP2004, 21) for a methoxy group (UP2064, 31) results in increased activity in the Melanoma panel. The methoxy analogue is more potent and acts against a greater number of cell lines. The methoxy analogue also exhibits improved activity against the colon cancer cell line Colo 205 and, in addition, the methoxy analogue exhibits activity against the renal cell line RXF-393 which is not observed with the benzyloxy compound. Replacing the electron rich dimethoxy A-ring with an iodo substituted aromatic ring (UP2023, 14) resulted in slight attenuation of activity in some cell lines, but the analogue showed activity against a wider spread of cell lines (i.e. 5 melanoma cell lines against only 3 for the benzyloxy analogue). Changing the nature of the C-ring ex-unsaturation from an alkene to a ketone (UP2067, 68) lead to additional activity against the breast cancer cell line MDA-MB-435, renal cell line RXF-393, the melanomas MALME-3M, M14, SKMEL-28, the CNS cancers SF-539 and SNB-75 and against the lung cell line NCI-H522.

The PBD dimer UP2001 (39) exhibited potent and selective cytoxicity activity against the lung cancer cell line NCl-H460, the colon cell line HCC-2998, the CNS cancer cell line SNB-75 and the melanoma cell lines MALME-3M (very potent, 0.08 μM) and UACC-62 (very potent, 0.07 μM), which may be attributable to its ability to cross link DNA.

Example 2(b)

Hollow Fibre Assay on Compounds of Formula II

Two of the compounds tested underwent the NCl Hollow Fibre Assay, and the results are presented below.

| | UP2001 (39) | UP2004 (21) |
|---|---|---|
| IP score | 40 | 8 |
| SC score | 14 | 10 |
| Total score | 54 | 18 |
| Cell Kill | Y | N |

UP2001 (39) and UP2004 (21) were subjected to the NCI Hollow Fibre assay described above. UP2001 has been selected for xenograft studies based on its combined IP+SC score (54) which was greatly in excess of 20, and its SC score which was higher than 8. UP2004 has been selected on the basis of its SC score, it being higher than 8.

Example 2(c)

Human Xenograft Studies on Compound 39 (UP 2001)

Human tumour xenograft studies on UP2001 were performed by the Biological Testing Branch of the NCI as described above.

Athymic nude mice bearing MDA-MB-435 xenografts (human mammary tumour), Ovcar-3 (human ovarian tumour), UACC-62 (human melanoma) or OVCAR-5 (human ovarian tumour) were treated at doses of 0.67 (high), 0.45 (middle) and 0.3 (low) mg/kg/injection given once every 4th day for a total of 3 doses (6 mice per dose level with 20 controls).

UP2001 (39) was evaluated by measuring the toxicity of the drug and its ability to retard tumour growth.

| Tumour | Toxicity | | | % T/C | | | % Growth Delay | | |
|---|---|---|---|---|---|---|---|---|---|
| | High | Mid | Low | High | Mid | Low | High | Mid | Low |
| MDA-MB-435 | 3/6 | 1/6 | 2/6 | toxic | 3 | 3 | 41 | 41 | 41 |
| OVCAR-3 | 0/6 | 0/6 | 0/6 | 7 | 20 | 46 | 73 | 73 | 9 |
| UACC-62 | 0/6 | 0/6 | 0/6 | 22 | 28 | 67 | 43 | 43 | 43 |
| OVCAR-5 | 0 | 0/6 | 0/6 | 52 | 45 | 38 | 16 | 28 | 32 |

Toxicity represents the number of mice which died as a result of treatment. % T/C represents the width of the tumours in the "test" mice (T) (as measured with calipers) compared to control untreated mice (C) and presented as a percentage. % Growth Delay represents the increase in the amount of time taken for the tumors to reach an arbitrary size of 250 mg.

In the MDA-MB-435 xenografts UP2001 restricted tumour growth in treated mice to only 3% of the tumour growth observed in the control population. In addition, a 41% delay in the time taken to reach tumour mass of 250 mg was also observed. Some toxicity towards the hosts was observed even at low dose.

A good dose response was observed for UP2001 (39) in the Ovcar-3 xenografts. At the high dose, tumour growth in treated subjects was only 7% of that observed in the control population. At the medium dose the value was 20% and at the low dose the tumours in the treated mice were 46% of the size of the control tumours. At the high dose a 73% growth delay in reaching a tumour mass of 250 mg was observed. No mice died as a result of exposure to UP2001 (39).

A similar dose response for tumour growth was observed in the UACC-62 xenografts for UP2001 (39). At the high dose treated tumours were 22% of the size of the control tumours. At the medium dose treated tumours were 28% of the size of the control tumours and at the low dose treated tumours were 67% of the size of the control tumours. Again no mice died as a result of exposure to UP2001 (39).

Results for the human ovarian tumour OVCAR-5 were less clear cut; approximately 50% tumour size reduction was observed and some growth delay was observed but activity appeared to be higher at lower concentrations. However, again, no mice died as a result of exposure to UP2001 (39).

UP2001 (39) was also evaluated against the human CNS tumour SF-295. Athymic nude mice bearing SF-295 were treated at doses of 0.40, 0.27 and 0.18 mg/Kg by injection given intravenously once daily for a total of 5 doses.

| Toxicity | | | % T/C | | | Tumour Free | | |
|---|---|---|---|---|---|---|---|---|
| High | Med | Low | High | Med | Low | High | Med | Low |
| 2/6 | 1/6 | 2/6 | 0% | 0% | 0% | 4/4 | 5/5 | 3/4 |

UP2001 (39) displayed curative properties against SF-295 xenografts. At high and medium doses all the surviving mice were tumour free on day 27 of the experiment. At the lower dose 3 out of 4 mice were tumour free on day 27. Some toxicity was associated with the treatment, 2 mice dying at the high dose, 1 at the medium dose and two at the low dose. The higher intensities of the injection schedule may be reflected in the higher mortality observed.

Example 3

Ovarian Carcinoma Cytotoxicity Assay

Compounds of the invention (and Anthramycin as a comparison) were evaluated for their cytotoxic activity in ovarian cell lines by Dr Lloyd R. Kelland's group at The Institute of Cancer Research, Sutton, UK. The five cell lines investigated were SKOV-3, A2780/A2780cisR and CH1/CH1cisR (cisR denotes that the cell line is resistant to cisplatin).

Single viable cells were seeded in growth medium (160 μL) in 96-well microtitre plates and allowed to attach overnight. The PBDs were then dissolved in DMSO (to give 20 mM drug concentrations) immediately prior to adding to the cells in quadruplicate wells. The final drug concentrations in the wells ranged from 100 μM to 2.5 nM as follows: 100, 25,10, 2.5,1 μM, 250, 100, 25, 10, 2.5 nM (drugs were diluted in growth medium and then 40 μL added to the existing well volume of 160 μL to give final concentrations as above). After 96 hours, the medium was removed and the remaining cells fixed by exposure to 10% trichloroacetic acid on ice for 30 minutes. The wells were then washed 3-4 times with tap water, air dried overnight and treated with 100 μL of sulphorhodamine B (0.4%) dissolved in 1% acetic acid. Staining was allowed to continue for 10-15 minutes, then the wells were washed 3-4 times with 1% acetic acid, air dried and then added to Tris base (100 μL of 10 mM). Plates were then shaken and absorbance readings at 540 nm were determined using a plate reader. By using the Quattro-Pro software package, the $IC_{50}$ values were calculated from plots of concentration versus percentage absorbance (compared with 8 untreated wells).

(b) Compounds of Formula II

| UP No. | $IC_{50}/\mu M$ | | | | |
|---|---|---|---|---|---|
| | A2780 | A2780cisR | CH1 | CH1cisR | Skov3 |
| Anthramycin | 0.155 | 0.16 | 0.062 | 0.05 | 0.16 |
| UP2001 (39) | 0.000023 | 0.000024 | 0.00012 | 0.0006 | 0.0091 |
| UP2004 (21) | 0.029 | 0.2 | 0.017 | 0.082 | 0.35 |
| UP2023 (14) | 0.49 | 1.45 | 0.37 | 0.43 | 16 |
| UP2064 (31) | 0.15 | 0.36 | 0.066 | 0.084 | 0.39 |
| UP2067 (68) | 0.115 | 0.39 | 0.165 | 0.18 | 0.54 |
| UP2100 (207) | <0.05 | 0.066 | <0.05 | <0.05 | 0.081 |

Compound UP2100 (207) has the structural; formula:

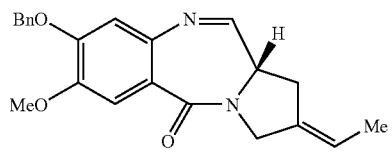

207 and was synthesised by the same route as compound 21.

UP2001 (39) exhibits cytotoxicity at picomolar/sub nanomolar levels across the ovarian tumour cell line panel. The potency of the molecule is probably due to its cross-linking properties coupled with the effect of exo saturation. UP2001 is markedly more potent than UP2053.

The monomers UP2004 (21) and UP2100 (207) exhibit good activity against the ovarian tumour cell lines comparable to that for anthramycin. UP2023 (14), which possesses a 7-iodo substituent is significantly less active than UP2004 (21), which contains two alkoxy groups at the 7 and 8 positions.

What is claimed is:

1. A compound of the formula:

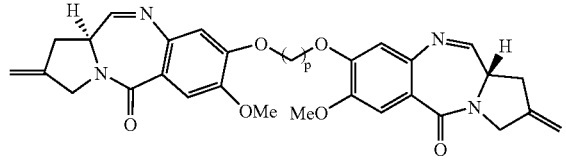

wherein p is 5.

2. A method of treating cancer of the human or animal body comprising administering to such a subject a therapeutically effective amount of a compound according to claim 1, wherein the cancer is selected from the group consisting of lung cancer, colon cancer, ONS cancer, melanoma, breast cancer, and ovarian cancer.

3. A method of treatment of a bacterial infection of the human or animal body comprising administering to such a subject a therapeutically effective amount of a compound according to claim 1.

* * * * *